(12) United States Patent
Chen et al.

US008299236B2

(10) Patent No.: US 8,299,236 B2
(45) Date of Patent: *Oct. 30, 2012

(54) COMPOSITIONS AND METHODS FOR ENHANCING DELIVERY OF NUCLEIC ACIDS INTO CELLS AND FOR MODIFYING EXPRESSION OF TARGET GENES IN CELLS

(75) Inventors: Lishan Chen, Bellevue, WA (US); Kunyuan Cui, Bothell, WA (US); Yuching Chen, Bellevue, WA (US); Sasha J. Mayer, Snohomish, WA (US); Michael E. Houston, Jr., Sammamish, WA (US)

(73) Assignee: Marina Biotech, Inc., Bothell, WA (US)

( * ) Notice: Subject to any disclaimer, the term of this patent is extended or adjusted under 35 U.S.C. 154(b) by 139 days.

This patent is subject to a terminal disclaimer.

(21) Appl. No.: 12/206,165

(22) Filed: Sep. 8, 2008

(65) Prior Publication Data
US 2009/0042298 A1 Feb. 12, 2009

Related U.S. Application Data

(63) Continuation of application No. 11/121,566, filed on May 4, 2005, now abandoned.

(60) Provisional application No. 60/568,027, filed on May 4, 2004, provisional application No. 60/570,512, filed on May 12, 2004, provisional application No. 60/570,513, filed on May 12, 2004, provisional application No. 60/613,416, filed on Sep. 27, 2004, provisional application No. 60/656,572, filed on Feb. 25, 2005, provisional application No. 60/667,833, filed on Apr. 1, 2005.

(51) Int. Cl.
*C07H 21/04* (2006.01)

(52) U.S. Cl. ............... 536/24.5; 536/24.31; 536/24.1; 514/44; 435/6; 435/325; 435/375

(58) Field of Classification Search .................. None
See application file for complete search history.

(56) References Cited

U.S. PATENT DOCUMENTS

| | | | |
|---|---|---|---|
| 5,334,711 A | 8/1994 | Sproat et al. | |
| 5,679,559 A | 10/1997 | Kim et al. | |
| 6,001,311 A | 12/1999 | Brennan | |
| 6,228,642 B1 | 5/2001 | Barker et al. | |
| 6,300,074 B1 | 10/2001 | Gold et al. | |
| 6,376,248 B1 * | 4/2002 | Hawley-Nelson et al. | ... 435/458 |
| 6,447,796 B1 | 9/2002 | Vook et al. | |
| 6,506,559 B1 | 1/2003 | Fire et al. | |
| 6,841,535 B2 * | 1/2005 | Divita et al. | ........ 514/13 |
| 2002/0130430 A1 | 9/2002 | Castor | |
| 2003/0018002 A1 * | 1/2003 | Sagara | ............. 514/44 |
| 2003/0130186 A1 * | 7/2003 | Vargeese et al. | ........ 514/12 |
| 2004/0019008 A1 | 1/2004 | Lewis et al. | |
| 2004/0110296 A1 | 6/2004 | Vargeese et al. | |
| 2005/0064595 A1 | 3/2005 | MacLachlan et al. | |
| 2005/0147993 A1 | 7/2005 | Khan | |
| 2005/0153913 A1 | 7/2005 | Kosak | |
| 2006/0014289 A1 | 1/2006 | Ahmadian et al. | |
| 2007/0020632 A1 * | 1/2007 | Tonelli et al. | .............. 435/6 |

FOREIGN PATENT DOCUMENTS

| | | |
|---|---|---|
| JP | 1121255 | 1/1999 |
| WO | 8902439 A1 | 3/1989 |
| WO | 9207065 A1 | 4/1992 |
| WO | 9315187 A1 | 8/1993 |
| WO | 9402595 A1 | 2/1994 |
| WO | 9404661 A1 | 3/1994 |
| WO | 9506731 A2 | 3/1995 |
| WO | 9511910 A1 | 5/1995 |
| WO | 9931262 A2 | 6/1999 |
| WO | 9932619 A1 | 7/1999 |
| WO | 9954459 A2 | 10/1999 |
| WO | 0053722 A2 | 9/2000 |
| WO | 0181370 A2 | 11/2001 |
| WO | 03046185 A1 | 6/2003 |
| WO | 03047518 A2 | 6/2003 |
| WO | 03070897 A2 | 8/2003 |
| WO | 03106491 A3 | 12/2003 |
| WO | 2004007721 A1 | 1/2004 |
| WO | 2004048545 A2 | 6/2004 |
| WO | 2004087931 | 10/2004 |
| WO | 2005021044 A2 | 3/2005 |
| WO | 2005117991 A2 | 12/2005 |

OTHER PUBLICATIONS

Simeoni et al. (2003) "Insight into the mechanism of the peptide-based gene delivery system MPG: implications for delivery of siRNA into mammalian cells" Nucleic Acids Res. 31(11):2717-2724.*
Chen, J. et al., "Galactosylated Histone-Mediated Gene Transfer and Expression," Human Gene Therapy, Mary Ann Lieber, Inc., Publishers, New Rochelle, NY, 1994, v.5, pp. 429-435.
Fernandez-Carneado, J. et al., "Amphipathic Peptides and Drug Delivery," Biopolymers (Peptide Science), Wiley Periodicals, Inc., 2004, v. 76: pp. 196-203.
Hebert, E., "Improvement of Exogenous DNA Nuclear Importation by Nuclear Localization Signal-Bearing Vectors: A Promising Way for Non-Viral Gene Therapy?" Biology of the Cell, Elsevier S.A.S., Paris, 2003, v. 95 (2), pp. 59-68.
Muratovska, A. et al., "Conjugate for Efficient Delivery of Short Interfering RNA (siRNA) into Mammalian Cells," FEBS Letters, Elsevier Science Publishers B.V., Amsterdam, 2003, v.558, pp. 63-68.

(Continued)

*Primary Examiner* — Kimberly Chong
(74) *Attorney, Agent, or Firm* — Merchant & Gould

(57) ABSTRACT

Polynucleotide delivery-enhancing polypeptides are admixed or complexed with, or conjugated to, nucleic acids for enhancing delivery the nucleic acids into cells. The transported nucleic acids are active in target cells as small inhibitory nucleic acids (siNAs) that modulate expression of target genes, mediated at least in part by RNA interference (RNAi). The siNA/polypeptide compositions and methods of the invention provide effective tools to modulate gene expression and alter phenotype in mammalian cells, including by altering phenotype in a manner that eliminates disease symptoms or alters disease potential in targeted cells or subject individuals to which the siNA/polypeptide compositions are administered.

13 Claims, 2 Drawing Sheets

OTHER PUBLICATIONS

Puebla, I. et al., "A Recombinant H1 Histone-Based System for Efficient Delivery of Nucleic Acids," Journal of Biotechnology, Elsevier Science Publishers B.V., Amsterdam, 2003, v. 105 (3), pp. 215-226.

Simeoni, F. et al., "Insight into the Mechanism of the Peptide-based Gene Delivery System MPG: Implications for Delivery of siRNA into Mammalian Cells," Nucleic Acids Research, Oxford University Press, 2003, v. 31 (11): pp. 2717-2724.

Sorensen, D. et al., "Gene Silencing by Systemic Delivery of Synthetic siRNAs in Adult Mice," Journal of Molecular Biology, Elsevier Science Ltd., London, 2003, v. 327, pp. 761-766.

Witkowska, R. et al., "Systematic analysis of cell penetrating peptides to deliver siRNA molecules," 3rd International and 28th European Peptide Symposium, Sep. 2004, Prague, CZ.

Ahktar, S. and Juliano, R. L., "Cellular uptake and intracellular fate of antisense oligonucleotides," Trends in Cell Biology, v. 2: pp. 139-144, Elsevier Science Publishers Ltd., 1992.

Aigner, A., "Delivery systems for the direct application of siRNAs to induce RNA interference (RNAi) in vivo," Journal of Biomedicine and Biotechnology, v. 2006: pp. 1-15, Hindawi Publishing Corporation, 2006.

Aldrian-Herrada, G., et al., "A peptide nucleic acid (PNA) is more rapidly internalized in cultured neurons when coupled to a retro-inverso delivery peptide," Nucleic Acids Research, v. 26 (21): pp. 4910-4916, Oxford University Press, 1998.

Boado, R. J., et al., "Drug delivery of antisense molecules to the brain for treatment of Alzheimer's Disease and cerebral AIDS," Journal of Pharmaceutical Sciences, v. 87 (11): pp. 1308-1315, American chemical Society and American Pharmaceutical Association, Nov. 1998.

Brennan, T., et al., "Two-dimensional parallel array technology as a new approach to automated combinatorial solid-phase organic synthesis," Biotechnology and Bioengineering, v. 61: pp. 33-45, John Wiley & Sons, 1998.

Brody, E. N. and Gold, L., "Aptamers as therapeutic and diagnostic agents," Reviews in Molecular Biotechnology, v. 74: pp. 5-13, Elsevier Science, 2000.

Burgin, A. B., et al., "Chemically modified hammerhead ribozymes with improved catalytic rates," Biochemistry, v. 35: pp. 14090-14097, American Chemical Society, 1996.

Caruthers, M. H., et al., "Chemical synthesis of deoxyoligonucleotides and deoxyoligonucleotide analogs," Methods in Enzymology, v. 211: pp. 3-21, Academic Press, 1992.

Cload, S. T. and Schepartz, A., "Polyether tethered oligonucleotide probes," Journal of the American Chemical Society, v. 113: pp. 6324-6326, American Chemical Society, 1991.

Conry, R. M., et al., "Phase I trial of a recombinant vaccinia virus encoding carcinoembryonic antigen in metastatic adenocarcinoma: comparison of intradermal versus subcutaneous administration," Clinical Cancer Research, v. 5: pp. 2330-2337, American Association for Cancer Research, 1999.

Durand, M., et al., "Circular dichroism studies of an oligodeoxyribonucleotide containing a hairpin loop made of a hexaethylene glycol chain: conformation and stability," Nucleic Acids, Research, v. 18 (21): pp. 6353-6359, Oxford University Press, 1990.

Ferentz, A. E. and Verdine, G. L., "Disulfide cross-linked oligonucleotides," Journal of the American Chemical Society, v. 113: pp. 4000-4002, american Chemical Society, 1991.

Flynn, M.A., et al., "Efficient delivery of small interfering RNA for inhibition of IL-12p40 expression in vivo," Journal of Inflammation, v. 1 (4): pp. 1-12, Biomed Central, 2004.

Funhoff, A. M. et al., "Endosomal escape of polymeric gene delivery complexes is not always enhanced by polymers buffering at low pH," Biomacromolecules, v. 5: pp. 32-39, American Chemical Society, 2004.

Gilmore, I.R. et al., "Delivery strategies for siRNA-mediated gene silencing," Current Drug Delivery, v. 3: pp. 147-155, Bentham Science Publishers Ltd., 2006.

Gilmore, I.R., et al., "The design and exogenous delivery of siRNA for post-transcriptional gene silencing," Journal of Drug Targeting, v. 12 (6): pp. 315-340, Taylor & Francis, 2004.

Gold, L., et al., "Diversity of oligonucleotide functions," Annual Review of Biochemistry, v. 64: pp. 763-797, Annual Reviews, 1995.

Gonzalez, H. et al., "New class of polymers for the delivery of macromolecular therapeutics," Bioconjugate Chemistry, v. 10: pp. 1068-1074, American Chemical Society, 1999.

Grayson, A.C.R., et al., "Biophysical and structural characterization of polyethyenimine-mediated siRNA delivery in vitro," Pharmaceutical Research, v. 23 (8): pp. 1868-1876, Springer Science & Business Media, 2006.

Guo, S., et al., "Construction of folate-conjugated pRNA of bacteriophage phi29 DNA packaging motor for delivery of chimeric siRNA to nasopharyngeal carcinoma cells," Gene Therapy: pp. 1-7, Nature Publishing Group, 2006.

Hassani, Z., et al., "Lipid-mediated siRNA delivery down regulates exogenous gene expression in the mouse brain at picomolar levels," Journal of Gene Medicine, Early View, published online, pp. 1-11, 2004.

Hermann, T. and Patel, D. J., "Adaptive recognition by nucleic acid aptamers," Science, v. 287: pp. 820-825, American Association for the Advancement of Science, 2000.

Hogrefe, R.I. et al., "Chemically modified short interfering hybrids (siHYBRIDS): nanoimmunoliposome delivery in vitro and in vivo for RNAi of HER-2," Nucleosides, Nucleotides and Nucleic Acids, v. 25: pp. 889-907, Taylor & Francis, 2006.

Ikeda, Y., and Kazunari, T., "Ligand-targeted delivery of therapeutic siRNA," Pharmaceutical Research: pp. 1-10, Springer Science & Business Media, 2006.

Jayasena, S. D., "Aptamers: an emerging class of molecules that rival antibodies in diagnostics," Clinical Chemistry, v. 45 (9): pp. 1628-1650, American Association for Clinical Chemistry, 1999.

Johnson, P. H., "Development of therapeutic siRNAs against TNF-alpha and novel peptide delivery agents for the treatment of rheumatoid arthritis," Beyond Genome 2005: RNA Interference Conference, Jun. 13, 2005. XP-002431337.

Juliano, R. L., "Peptide-oligonucleotide conjugates for the delivery of antisense and siRNA," current Opinion in Molecular Therapeutics, v. 7 (2): pp. 132-136, the Thomson Corporation, 2005.

Kataoka, K., et al., "Smart polymeric micelles as nanocarriers for oligonucleotides and siRNA delivery," Nucleic Acids Symposium Series No. 49: pp. 17-18, Oxford University Press, 2005.

Khan, A., et al., "Sustained polymeric delivery of gene silencing antisense ODNs, siRNA, DNAzymes and Ribozymes: in vitro and in vivo studies," Journal of Drug Targeting, v. 12 (6): pp. 393-404, Taylor & Francis, 2004.

Kusser, W., "Chemically modified nucleic acid aptamers for in vitro selections: evolving evolution," Reviews in Molecular Biology, v. 74 (1): pp. 27-38, Elsevier Science Publishers, 2000.

Landen, C. N., et al., "Therapeutic EphA2 gene targeting in vivo using neutral liposomal small interfering RNA delivery," Cancer Research, v. 65 (15): pp. 6910-6918, American Association for Cancer Research, 2005.

Lewis, D. L., "Efficient delivery of siRNA for inhibition of gene expression in postnatal mice," Nature Genetics, v. 32: pp. 107-108, Nature Publishing Group, 2002.

Lewis, D., L. "Delivery of siRNA and siRNA expression constructs to adult mammals by hydrodynamic intravascular injection," Methods in Enzymology, v. 392: pp. 336-350, Elsevier, 2005.

Limbach, P. A., et al., "Summary: the modified nucleosides of RNA," Nucleic Acids Research, v. 22 (12): pp. 2183-2196, Oxford University Press, 1994.

Loakes, D., "The applications of universal DNA base analogues," Nucleic Acids Research, v. 29 (12): pp. 2437-2447, Oxford University Press, 2001.

Ma, M Y-X., et al., "Design and synthesis of RNA miniduplexes via a synthetic linker approach," Biochemistry, v. 32: pp. 1751-1758, American Chemical Society, 1993.

Ma, M Y-X., et al., "Design and synthesis of RNA miniduplexes via a synthetic linker approach. 2. Generation of covalently closed, double-stranded cyclic HIV-2 TAR RNA analogs with high Tat-binding affinity," Nucleic Acids Research, v. 21 (11): pp. 2585-2589, Oxford University Press, 1993.

Martinez, J., et al., "Single-stranded antisense siRNAs guide target RNA cleavage in RNAi," Cell, v. 110: pp. 563-574, Cell Press, 2002.

Massaro, D., "Noninvasive delivery of small inhibitory RNA and other reagents to pulmonary alveoli in mice," American Journal of Physiology and Lung Cell Molecular Physiology, v. 287: L1066-L1070, the American Physiological Society, 2004.

Maurer, N., et al., "Lipid-based systems for the intracellular delivery of genetic drugs," Molecular Membrane Biology, v. 16: pp. 129-140, Taylor & Francis Ltd, 1999.

Meyer, et al. "Combinatorial Recombination of Gene Fragments to Construct a Library of Chimeras," Current Protocols in Protein Science, 26.2.1-26.2.17, 2006.

Moriguchi, R, et al., "A multifunctional envelope-type nano device for novel gene delivery of siRNA plasmids," International Journal of Pharmaceutics, v. 30: pp. 1-9, Elsevier, B.V., 2005.

Oliveira, S., et al., "Targeted delivery of siRNA," Journal of Biomedicine and Biotechnology, v. 2006: pp. 1-9, Hindawi Publishing Corporation, 2006.

Parker, M. D., et al., "Nanoparticle delivery of siRNa gene knockdown to reduce pro-inflammatory gene expression in the donor kidney," World Transplant Congress 2006 oral Abstract, Concurrent Session 76, Intradigm Corporation, 2006.

Prechtel, A. T., et al., "Small interfering RNA (siRNA) delivery into monocyte-derived dendritic cells by electroporation," Journal of Immunological Methods, v. 311: pp. 139-152, Elsevier B.V., 2006.

Richardson, P.L. and Schepartz, A., "Tethered oligonucleotide probes: a strategy for the recognition of structured RNA," Journal of the American Chemical Society, v. 113: pp. 5109-5111, American Chemical Society, 1991.

Scaringe, S.A., et al., "Chemical synthesis of biologically active oligoribonucleotides using beta-cyanoethyl protected ribonucleoside phosphoramidites," Nucleic Acids Research, v. 18 (18): pp. 5433-5441, Oxford University Press, 1990.

Schiffelers, R. M., et al., "Cancer siRNA therapy by tumor selective delivery with ligand-targeted sterically stabilized nanoparticle," Nucleic Acids Research, v. 32 (19): pp. (e149) 1-10, Oxford University Prress, 2004.

Schwarz, D.S., et al., "Evidence that siRNAs function as guides, not primers, in the *Drosophila* and human RNAi pathways," Molecular Cell, v. 10: pp. 537-548, Cell Press, 2002.

Seela, F. and Kaiser, K., "Oligodeoxyribonucleotides containing 1,3-propanediol as nucleoside substitute," Nucleic Acids Research, v. 15 (7): pp. 3113-3129, IRL Press Limited, 1987.

Simeoni, F., et al., "Peptide-based strategy for siRNA delivery into mammalian cells," Methods in Molecular Biology, v. 309: RNA Silencing: Methods and Protocols, pp. 251-260, Humana Press, 2005.

Simpson, R. J. Y., et al., CCHX Zinc finger derivatives retain the ability to bind Zn(II) and mediate protein-DNA interactions, the Journal of Biological Chemistry, v. 278 (30): pp. 28011-28018, American Society for Biochemistry and Molecular Biology, Inc., 2003.

Sioud, M. and Sorensen, D. R., "Cationic liposome-mediated delivery of siRNAs in adult mice," Biochemical and Biophysical Research Communications, v 312: pp. 1220-1225, Elsevier Inc., 2003.

Spagnou, S., et al., "Lipidic carriers of siRNA: differences in the formulation, cellular uptake and delivery with plasmid DNA," Biochemistry, v. 43: pp. 13348-13356, American Chemical Society, 2004.

Sun, S., "Technology evaluation: SELEX, Gilead Sciences Inc.," Current Opinion in Molecular Therapeutics, v. 2 (1): pp. 100-105, Thomson Scientific, 2000.

Thomas, M. et al., "Polycation-mediated delivery of siRNAs for prophylaxis and treatment of influenza virus infection," Expert Opinion, pp. 495-505, Ashley Publications, 2005.

Usman, N., et al., "Automated chemical synthesis of long oligoribonucleotides using 2'-o-silylated ribonucleoside 3'-O-phosphoramidites on a controlled-pore glass support," Journal of the American Chemical Society, v. 109: pp. 7845-7854, American Chemical Society, 1987.

Vornlocher, H-P., "Antibody-directed cell-type-specific delivery of siRNA," Trends in Molecular Medicine, v. 12 (1): pp. 1-3, Elsevier, 2005.

Wincott, F., "A practical method for the production of RNA and ribozymes," Methods in Molecular Biology, v. 74: pp. 59-68, Humana Press, 1997.

Wincott, F., et al., "Synthesis, deprotection, analysis and purification of RNA and ribozymes," Nucleic Acids Research, v. 23 (14): 2677-2684, Oxford University Press, 1995.

Witkowska, R., et al., Peptide-mediated delivery of siRNA via noncovalent complexes and covalent conjugates, 19th American Peptide Symposium, Jun. 18-23, 2005, held in San Diego, CA.

Non Final Rejection for US Patent No. 6,841,535, Mailed, Mar. 10, 2004 (8 pp.).

Non Final Rejection for US Patent No. 7,112,442, Mailed Feb. 5, 2004 (12 pp.).

Non Final Rejection for US Patent No. 7,112,442, Mailed Jul. 9, 2004 (8 pp.).

Final Rejection for US Patent No. 7,112,442, Mailed Mar. 8, 2005 (6 pp.).

Non Final Rejection in U.S. Appl. No. 11/223,699, Mailed Jun. 13, 2008 (17 pp.).

Final Rejection in U.S. Appl. No. 11/223,699, Mailed Dec. 13, 2007 (23 pp.).

Non Final Rejection in U.S. Appl. No. 11/223,699, Mailed Jun. 19, 2008 (15 pp.).

Final Rejection in U.S. Appl. No. 11/223,699, Mailed Mar. 9, 2009 (9 pp.).

Non Final Rejection in U.S. Appl. No. 11/743,480, Mailed Sep. 17, 2008 (10 pp.).

Final Rejection in U.S. Appl. No. 11/743,480, Mailed Apr. 24, 2009 (14 pp.).

Non Final Rejection in U.S. Appl. No. 11/837,432, Mailed Jun. 13, 2008 (9 pp.).

Final Rejection in U.S. Appl. No. 11/837,432, Mailed Apr. 1, 2009 (10 pp.).

International Search Report Mailed Oct. 20, 2006; International Application No. PCT/US2005/015574; International Filing Date: May 4, 2005; Applicant: Nastech Pharmaceutical Company, Inc.; Title: Compositions and Methods for Enhancing Delivery of Nucleic Acids Into Cells and for Modifying Expression of Target Genes in Cells; 22 pp.

Partial International Search Report Mailed May 15, 2007; International Application No. PCT/US2006/034859; International Filing Date: Sep. 8, 2006; Applicant: Nastech Pharmaceutical Company, Inc.; Title: Pharmaceutical Compositions for Delivery of Ribonucleic Acid to a Cell; 11 pp.

International Search Report Mailed Jul. 16, 2007; International Application No. PCT/US2006/042978; International Filing Date: Nov. 3, 2006; Applicant: Nastech Pharmaceutical Company, Inc.; Title: Peptide-Dicer Substrate RNA Conjugates As Delivery Vehicles for siRNA; 7 pp.

International Search Report Mailed Feb. 26, 2008; International Application No. PCT/US2007/075744; International Filing Date: Aug. 10, 2007; Applicant: Nastech Pharmaceutical Company, Inc.; Title: Dicer Substrate RNA Peptide Conjugates and Methods for RNA Therapeutics; 8 pp.

Partial International Search Report Mailed Jul. 20, 2007; International Application No. PCT/US2006/040174; International Filing Date: Oct. 13, 2006; Applicant: Nastech Pharmaceutical Company, Inc.; Title: Compounds and Methods for Peptide Ribonucleic Acid Condensate Particles for RNA Therapeutics; 4 pp.

\* cited by examiner

COMPOSITIONS AND METHODS FOR ENHANCING DELIVERY OF NUCLEIC ACIDS INTO CELLS AND FOR MODIFYING EXPRESSION OF TARGET GENES IN CELLS

CROSS-REFERENCES TO RELATED APPLICATIONS

This application is a continuation claiming the benefit under 35 U.S.C. §120 of co-pending U.S. patent application Ser. No. 11/121,566, filed May 4, 2005, which claimed the priority benefit of U.S. Provisional Patent Application No. 60/568,027, filed May 4, 2004, U.S. Provisional Patent Application No. 60/570,512, filed May 12, 2004, U.S. Provisional Patent Application No. 60/570,513, filed May 12, 2004, U.S. Provisional Patent Application No. 60/613,416, filed Sep. 27, 2004, U.S. Provisional Patent Application No. 60/656,572 filed Feb. 25, 2005, and U.S. Provisional Patent Application No. 60/667,833, filed Apr. 1, 2005, the disclosures of which are incorporated herein by reference in their entirety.

TECHNICAL FIELD

The invention relates to methods and compositions for delivering nucleic acids into cells. More specifically, the invention relates to procedures and preparations for delivering double-stranded polynucleotides into cells to modify expression of target genes to alter a phenotype, such as a disease state or potential, of the cells.

BACKGROUND OF THE INVENTION

Delivering nucleic acids into animal and plant cells has long been an important object of molecular biology research and development. Recent developments in the areas of gene therapy, antisense therapy and RNA interference (RNAi) therapy have created a need to develop more efficient means for introducing nucleic acids into cells.

A diverse array of plasmids and other nucleic acid "vectors" have been developed for delivering large polynucleotide molecules into cells. Typically these vectors incorporate large DNA molecules comprising intact genes for the purpose of transforming target cells to express a gene of scientific or therapeutic interest.

The process by which exogenous nucleic acids are delivered artificially into cells is generally referred to as transfection. Cells can be transfected to uptake a functional nucleic acid from an exogenous source using a variety of techniques and materials. The most commonly used transfection methods are calcium phosphate transfection, and electroporation. A variety of other methods for transducing cells to deliver exogenous DNA or RNA molecules have been developed, including viral-mediated transduction, cationic lipid or liposomal delivery, and numerous methods that target mechanical or biochemical membrane disruption/penetration (e.g., using detergents, microinjection, or particle guns).

RNA interference is a process of sequence-specific post transcriptional gene silencing in cells initiated by a double-stranded (ds) polynucleotide, usually a dsRNA, that is homologous in sequence to a portion of a targeted messenger RNA (mRNA). Introduction of a suitable dsRNA into cells leads to destruction of endogenous, cognate mRNAs (i.e., mRNAs that share substantial sequence identity with the introduced dsRNA). The dsRNA molecules are cleaved by an RNase III family nuclease called dicer into short-interfering RNAs (siRNAs), which are 19-23 nucleotides (nt) in length. The siRNAs are then incorporated into a multicomponent nuclease complex known as the RNA-induced silencing complex or "RISC". The RISC identifies mRNA substrates through their homology to the siRNA, and effectuates silencing of gene expression by binding to and destroying the targeted mRNA.

RNA interference is emerging a promising technology for modifying expression of specific genes in plant and animal cells, and is therefore expected to provide useful tools to treat a wide range of diseases and disorders amenable to treatment by modification of endogenous gene expression.

There remains a long-standing need in the art for better tools and methods to deliver siRNAs and other small inhibitory nucleic acids (siNAs) into cells, particularly in view of the fact that existing techniques for delivering nucleic acids to cells are limited by poor efficiency and/or high toxicity of the delivery reagents. Related needs exist for improved methods and formulations to deliver siNAs in an effective amount, in an active and enduring state, and using non-toxic delivery vehicles, to selected cells, tissues, or compartments to mediate regulation of gene expression in a manner that will alter a phenotype or disease state of the targeted cells.

DESCRIPTION OF EXEMPLARY EMBODIMENTS OF THE INVENTION

Figure 1:
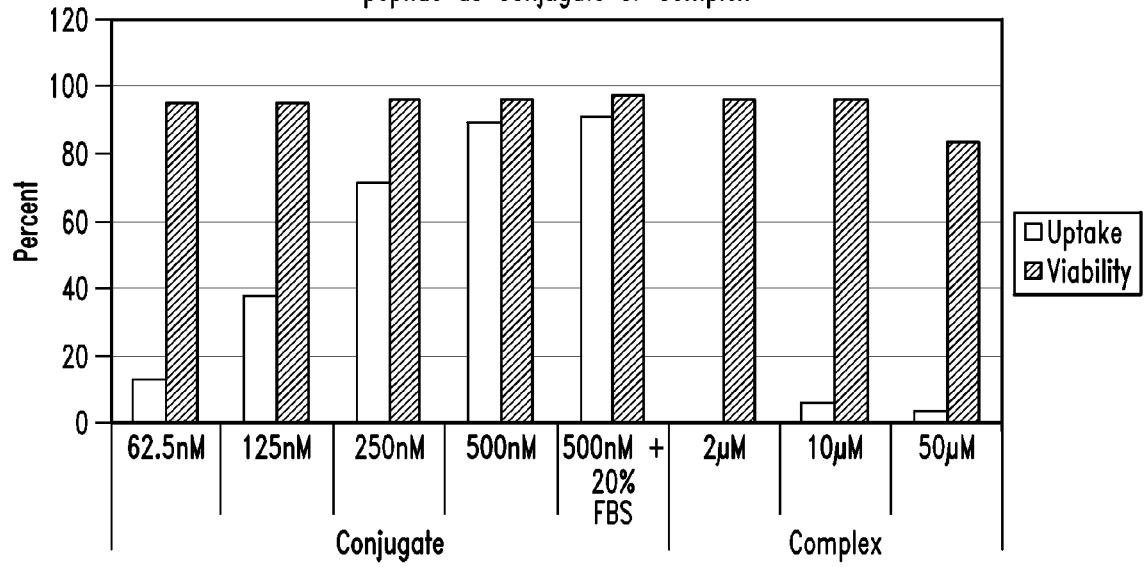
FIG. 1 illustrates peptide-mediated uptake of siNAs complexed or conjugated to a polynucleotide delivery-enhancing polypeptide of the invention (SEQ ID NO: 35).

The present invention satisfies these needs and fulfills additional objects and advantages by providing novel compositions and methods that employ a short interfering nucleic acid (siNA), or a precursor thereof, in combination with a polynucleotide delivery-enhancing polypeptide. The polynucleotide delivery-enhancing polypeptide is a natural or artificial polypeptide selected for its ability to enhance intracellular delivery or uptake of polynucleotides, including siNAs and their precursors.

Within the novel compositions of the invention, the siNA may be admixed or complexed with, or conjugated to, the polynucleotide delivery-enhancing polypeptide to form a composition that enhances intracellular delivery of the siNA as compared to delivery resulting from contacting the target cells with a naked siNA (i.e., siNA without the delivery-enhancing polypeptide present).

In certain embodiments of the invention, the polynucleotide delivery-enhancing polypeptide is a histone protein, or a polypeptide or peptide fragment, derivative, analog, or conjugate thereof. Within these embodiments, the siNA is admixed, complexed or conjugated with one or more full length histone proteins or polypeptides corresponding at least in part to a partial sequence of a histone protein, for example of one or more of the following histones: histone H1, histone H2A, histone H2B, histone H3 or histone H4, or one or more polypeptide fragments or derivatives thereof comprising at least a partial sequence of a histone protein, typically at least 5-10 or 10-20 contiguous residues of a native histone protein. In more detailed embodiments, the siRNA/histone mixture, complex or conjugate is substantially free of amphipathic compounds. In other detailed embodiments, the siNA that is admixed, complexed, or conjugated with the histone protein or polypeptide will comprise a double-stranded double-stranded RNA, for example a double-stranded RNA that has 30 or fewer nucleotides, and is a short interfering RNA (siRNA). In exemplary embodiments, the histone polynucleotide delivery-enhancing polypeptide comprises a fragment of histone H2B, as exemplified by the polynucleotide delivery-enhancing polypeptide designated PN73 described herein below. In yet additional detailed embodiments, the polynucleotide delivery-enhancing polypeptide may be pegylated to improve stability and/or efficacy, particularly in the context of in vivo administration.

Within additional embodiments of the invention, the polynucleotide delivery-enhancing polypeptide is selected or rationally designed to comprise an amphipathic amino acid sequence. For example, useful polynucleotide delivery-enhancing polypeptides may be selected which comprise a plurality of non-polar or hydrophobic amino acid residues that that is able to insert into and preferably transit through the membrane of cells. A fusogenic peptide is a peptide that is able destabilize a lipid membrane, for example a plasma membrane or membrane surrounding an endosome, which may be enhanced at low pH. Exemplary fusogenic domains or motifs are found in a broad diversity of viral fusion proteins and in other proteins, for example fibroblast growth factor 4 (FGF4).

To rationally design polynucleotide delivery-enhancing polypeptides of the invention, a protein transduction domain is employed as a motif that will facilitate entry of the nucleic acid into a cell through the plasma membrane. In certain embodiments, the transported nucleic acid will be encapsulated in an endosome. The interior of endosomes has a low pH resulting in the fusogenic peptide motif destabilizing the membrane of the endosome. The destabilization and breakdown of the endosome membrane allows for the release of the siNA into the cytoplasm where the siNA can associate with a RISC complex and be directed to its target mRNA.

Examples of protein transduction domains for optional incorporation into polynucleotide delivery-enhancing polypeptides of the invention include:

```
 1. TAT protein transduction domain (PTD) (SEQ ID NO: 1)    KRRQRRR;

2. Penetratin PTD (SEQ ID NO: 2)                            RQIKIWFQNRRMKWKK;

3. VP22 PTD (SEQ ID NO: 3)                                  DAATATRGRSAASRPTERPRAPARSASRPRRPVD;

4. Kaposi FGF signal sequences (SEQ ID NO: 4)               AAVALLPAVLLALLAP,
 and (SEQ ID NO: 5)                                              AAVLLPVLLPVLLAAP;

5. Human β integrin signal sequence (SEQ ID NO: 6)          VTVLALGALAGVGVG;

6. gp41 fusion sequence (SEQ ID NO: 7)                      GALFLGWLGAAGSTMGA;

7. Caiman crocodylus Ig(v) light chain (SEQ ID NO: 8)       MGLGLHLLVLAAALQGA;

8. hCT-derived peptide (SEQ ID NO: 9)                       LGTYTQDFNKFHTFPQTAIGVGAP;

9. Transportan (SEQ ID NO: 10)                              GWTLNSAGYLLKINLKALAALAKKIL;

10. Loligomer (SEQ ID NO: 11)                                TPPKKKRKVEDPKKKK;

11. Arginine peptide (SEQ ID NO: 12)                         RRRRRRR;
 and

12. Amphiphilic model peptide (SEQ ID NO: 13)                KLALKALKALKAALKIA.
``` form a hydrophobic sequence domain or motif, linked to a plurality of charged amino acid residues that form a charged sequence domain or motif, yielding an amphipathic peptide.

Examples of viral fusion peptides fusogenic domains for optional incorporation into polynucleotide delivery-enhancing polypeptides of the invention include:

```
1. Influenza HA2 (SEQ ID NO: 14)                         GLFGAIAGFIENGWEG;

2. Sendai F1 (SEQ ID NO: 15)                             FFGAVIGTIALGVATA;

3. Respiratory Syncytial virus F1 (SEQ ID NO: 16)        FLGFLLGVGSAIASGV;

4. HIV gp41 (SEQ ID NO: 17)                              GVFVLGFLGFLATAGS;
 and

5. Ebola GP2 (SEQ ID NO: 14)                             GAAIGLAWIPYFGPAA.
```

In other embodiments, the polynucleotide delivery-enhancing polypeptide is selected to comprise a protein transduction domain or motif, and a fusogenic peptide domain or motif. A protein transduction domain is a peptide sequence Within yet additional embodiments of the invention, polynucleotide delivery-enhancing polypeptides are provided that incorporate a DNA-binding domain or motif which facilitates polypeptide-siNA complex formation and/or enhances delivery of siNAs within the methods and compositions of the invention. Exemplary DNA binding domains in this context include various "zinc finger" domains as described for DNA-binding regulatory proteins and other proteins identified in Table 1, below (see, e.g., Simpson et al., J. Biol. Chem. 278:28011-28018, 2003).

TABLE 1

Exemplary Zinc Finger Motifs of Different DNA-binding Proteins
C$_2$H$_2$ Zinc finger motif

```
            ....|....|    ....|....|    ....|....|    ....|....|    ....|....|    ....|....|
                665           675           685           695           705           715
Sp1         ACTCPYCKDS    EGRGSG----    DPGKKKQHIC    HIQGCGKVYG    KTSHLRAHLR    WHTGERPFMC    (SEQ ID NO: 19)
Sp2         ACTCPNCKDG    EKRS------    GEQGKKKHVC    HIPDCGKTFR    KTSLLRAHVR    LHTGERPFVC    (SEQ ID NO: 20)
Sp3         ACTCPNCKEG    GGRGTN----    -LGKKKQHIC    HIPGCGKVYG    KTSHLRAHLR    WHSGERPFVC    (SEQ ID NO: 21)
Sp4         ACSCPNCREG    EGRGSN----    EPGKKKQHIC    HIEGCGKVYG    KTSHLRAHLR    WHTGERPFIC    (SEQ ID NO: 22)
DrosBtd     RCTCPNCTNE    MSGLPPIVGP    DERGRKQHIC    HIPGCERLYG    KASHLKTHLR    WHTGERPFLC    (SEQ ID NO: 23)
DrosSp      TCDCPNCQEA    ERLGPAGV--    HLRKKNIHSC    HVPGCGKVYG    KTSHLKAHLR    WHTGERPFVC    (SEQ ID NO: 24)
CeT22C8.5   RCTCPNCKAI    KHG-------    DRGSQHTHLC    SVPGCGKTYK    KTSHLRAHLR    KHTGDRPFVC    (SEQ ID NO: 25)
Y40B1A.4    PQISLKKKTF    FFIFSNFR--    GDGKSRIHIC    HL--CNKTYG    KTSHLRAHLR    GHAGNKPFAC    (SEQ ID NO: 26)
```

*The table demonstrates a conservative zinc fingerer motif for double strand DNA binding which itself can be used to select and design additional polynucleotide delivery-enhancing polypeptides according to the invention.

Alternative DNA binding domains useful for constructing polynucleotide delivery-enhancing polypeptides of the invention include, for example, portions of the HIV Tat protein sequence (see, Examples, below).

Within exemplary embodiments of the invention described herein below, polynucleotide delivery-enhancing polypeptides may be rationally designed and constructed by combining any of the foregoing structural elements, domains or motifs into a single polypeptide effective to mediate enhanced delivery of siNAs into target cells. For example, a protein transduction domain of the TAT polypeptide was fused to the N-terminal 20 amino acids of the influenza virus hemagglutinin protein, termed HA2, to yield one exemplary polynucleotide delivery-enhancing polypeptide herein. Various other polynucleotide delivery-enhancing polypeptide constructs are provided in the instant disclosure, evincing that the concepts of the invention are broadly applicable to create and use a diverse assemblage of effective polynucleotide delivery-enhancing polypeptides for enhancing siNA delivery.

Yet additional exemplary polynucleotide delivery-enhancing polypeptides within the invention may be selected from the following peptides:

```
                                        (SEQ ID NO: 27)
WWETWKPFQCRICMRNFSTRQARRNHRRRHR;

(SEQ ID NO: 28)
GKINLKALAALAKKIL, (SEQ ID NO: 29)
RVIRVWFQNKRCKDKK, (SEQ ID NO: 30)
GRKKRRQRRRPPQGRKKRRQRRRPPQGRKKRRQRRRPPQ, (SEQ ID NO: 31)
GEQIAQLIAGYIDIILKKKKSK,
```

Poly Lys-Trp, 4:1, MW 20,000-50,000; and Poly Orn-Trp, 4:1, MW 20,000-50,000. Additional polynucleotide delivery-enhancing polypeptides that are useful within the compositions and methods herein comprise all or part of the mellitin protein sequence.

Still other exemplary polynucleotide delivery-enhancing polypeptides are identified in the examples below. Any one or combination of these peptides may be selected or combined to yield effective polynucleotide delivery-enhancing polypeptide reagents to induce or facilitate intracellular delivery of siNAs within the methods and compositions of the invention.

In more detailed aspects of the invention, the mixture, complex or conjugate comprising a siRNA and a polynucleotide delivery-enhancing polypeptide can be optionally combined with (e.g., admixed or complexed with) a cationic lipid, such as LIPOFECTIN®. In this context it is unexpectedly disclosed herein that polynucleotide delivery-enhancing polypeptides complexed or conjugated to a siRNA alone will effectuate delivery of the siNA sufficient to mediate gene silencing by RNAi. However, it is further unexpectedly disclosed herein that a siRNA/polynucleotide delivery-enhancing polypeptide complex or conjugate will exhibit even greater activity for mediating siNA delivery and gene silencing when admixed or complexed with a cationic lipid, such as lipofectin. To produce these compositions comprised of a polynucleotide delivery-enhancing polypeptide, siRNA and a cationic lipid, the siRNA and peptide may be mixed together first in a suitable medium such as a cell culture medium, after which the cationic lipid is added to the mixture to form a siRNA/delivery peptide/cationic lipid composition. Optionally, the peptide and cationic lipid can be mixed together first in a suitable medium such as a cell culture medium, whereafter the siRNA can be added to form the siRNA/delivery peptide/cationic lipid composition.

Examples of useful cationic lipids within these aspects of the invention include N-[1-(2,3-dioleoyloxy)propyl]-N,N,N-trimethylammonium chloride, 1,2-bis(oleoyloxy)-3-3-(trimethylammonium)propane, 1,2-dimyristyloxypropyl-3-dimethylhydroxyethylammonium bromide, and dimethyldioctadecylammonium bromide, 2,3-dioleyloxy-N-[2(sperminecarboxamido)ethyl]-N,N-dimethyl-1-propanaminium trifluoracetate, 1,3-dioleoyloxy-2-(6-carboxyspermyl)-propylamid, 5-carboxyspermylglycine dioctadecylamide, tetramethyltetrapalmitoyl spermine, tetramethyltetraoleyl spermine, tetramethyltetralauryl spermine, tetramethyltetramyristyl spermine and tetramethyldioleyl spermine. DOTMA (N-[1-(2,3-dioleoyloxy)propyl]-N,N,N-trimethyl ammonium chloride), DOTAP (1,2-bis(oleoyloxy)-3,3-(trimethylammonium)propane), DMRIE (1,2-dimyristyloxypropyl-3-dimethyl-hydroxy ethyl ammonium bromide) or DDAB (dimethyl dioctadecyl ammonium bromide). Polyvalent cationic lipids include lipospermines, specifically DOSPA (2,3-dioleyloxy-N-[2(sperminecarboxamido)ethyl]-N,N-dimethyl-1-propanaminium trifluoro-acetate) and DOSPER (1,3-dioleoyloxy-2-(6-carboxy spermyl)-propyl-amid, and the di- and tetra-alkyl-tetra-methyl spermines, including but not limited to TMTPS (tetramethyltetrapalmitoyl spermine), TMTOS (tetramethyltetraoleyl spermine), TMTLS (tetramethlytetralauryl spermine), TMTMS (tetramethyltetramyristyl spermine) and TMDOS (tetramethyldioleyl spermine) DOGS (dioctadecyl-amidoglycylspermine (TRANSFECTA®). Other useful cationic lipids are described, for example, in U.S. Pat. No. 6,733,777; U.S. Pat. No. 6,376,248; U.S. Pat. No. 5,736,392; U.S. Pat. No. 5,686,958; U.S. Pat. No. 5,334,761 and U.S. Pat. No. 5,459,127.

Cationic lipids are optionally combined with non-cationic lipids, particularly neutral lipids, for example lipids such as DOPE (dioleoylphosphatidylethanolamine), DPhPE (diphytanoylphosphatidylethanolamine) or cholesterol. A cationic lipid composition composed of a 3:1 (w/w) mixture of DOSPA and DOPE or a 1:1 (w/w) mixture of DOTMA and DOPE (LIPOFECTIN®, Invitrogen) are generally useful in transfecting compositions of this invention. Preferred transfection compositions are those which induce substantial transfection of a higher eukaryotic cell line.

In exemplary embodiments, the instant invention features compositions comprising a small nucleic acid molecule, such as short interfering nucleic acid (siNA), a short interfering RNA (siRNA), a double-stranded RNA (dsRNA), microRNA (mRNA), or a short hairpin RNA (shRNA), admixed or complexed with, or conjugated to, a polynucleotide delivery-enhancing polypeptide.

As used herein, the term "short interfering nucleic acid", "siNA", "short interfering RNA", "siRNA", "short interfering nucleic acid molecule", "short interfering oligonucleotide molecule", or "chemically-modified short interfering nucleic acid molecule", refers to any nucleic acid molecule capable of inhibiting or down regulating gene expression or viral replication, for example by mediating RNA interference "RNAi" or gene silencing in a sequence-specific manner. Within exemplary embodiments, the siNA is a double-stranded polynucleotide molecule comprising self-complementary sense and antisense regions, wherein the antisense region comprises a nucleotide sequence that is complementary to a nucleotide sequence in a target nucleic acid molecule for downregulating expression, or a portion thereof, and the sense region comprises a nucleotide sequence corresponding to (i.e., which is substantially identical in sequence to) the target nucleic acid sequence or portion thereof.

"siNA" means a small interfering nucleic acid, for example a siRNA, that is a short-length double-stranded nucleic acid (or optionally a longer precursor thereof), and which is not unacceptably toxic in target cells. The length of useful siNAs within the invention will in certain embodiments be optimized at a length of approximately 21 to 23 bp long. However, there is no particular limitation in the length of useful siNAs, including siRNAs. For example, siNAs can initially be presented to cells in a precursor form that is substantially different than a final or processed form of the siNA that will exist and exert gene silencing activity upon delivery, or after delivery, to the target cell. Precursor forms of siNAs may, for example, include precursor sequence elements that are processed, degraded, altered, or cleaved at or following the time of delivery to yield a siNA that is active within the cell to mediate gene silencing. Thus, in certain embodiments, useful siNAs within the invention will have a precursor length, for example, of approximately 100-200 base pairs, 50-100 base pairs, or less than about 50 base pairs, which will yield an active, processed siNA within the target cell. In other embodiments, a useful siNA or siNA precursor will be approximately 10 to 49 bp, 15 to 35 bp, or about 21 to 30 bp in length.

In certain embodiments of the invention, as noted above, polynucleotide delivery-enhancing polypeptides are used to facilitate delivery of larger nucleic acid molecules than conventional siNAs, including large nucleic acid precursors of siNAs. For example, the methods and compositions herein may be employed for enhancing delivery of larger nucleic acids that represent "precursors" to desired siNAs, wherein the precursor amino acids may be cleaved or otherwise processed before, during or after delivery to a target cell to form an active siNA for modulating gene expression within the target cell. For example, a siNA precursor polynucleotide may be selected as a circular, single-stranded polynucleotide, having two or more loop structures and a stem comprising self-complementary sense and antisense regions, wherein the antisense region comprises a nucleotide sequence that is complementary to a nucleotide sequence in a target nucleic acid molecule or a portion thereof, and the sense region having nucleotide sequence corresponding to the target nucleic acid sequence or a portion thereof, and wherein the circular polynucleotide can be processed either in vivo or in vitro to generate an active siNA molecule capable of mediating RNAi.

In mammalian cells, dsRNAs longer than 30 base pairs can activate the dsRNA-dependent kinase PKR and 2'-5'-oligoadenylate synthetase, normally induced by interferon. The activated PKR inhibits general translation by phosphorylation of the translation factor eukaryotic initiation factor $2\alpha$ (eIF$2\alpha$), while 2'-5'-oligoadenylate synthetase causes nonspecific mRNA degradation via activation of RNase L. By virtue of their small size (referring particularly to non-precursor forms), usually less than 30 base pairs, and most commonly between about 17-19, 19-21, or 21-23 base pairs, the siNAs of the present invention avoid activation of the interferon response.

In contrast to the nonspecific effect of long dsRNA, siRNA can mediate selective gene silencing in the mammalian system. Hairpin RNAs, with a short loop and 19 to 27 base pairs in the stem, also selectively silence expression of genes that are homologous to the sequence in the double-stranded stem. Mammalian cells can convert short hairpin RNA into siRNA to mediate selective gene silencing.

RISC mediates cleavage of single stranded RNA having sequence complementary to the antisense strand of the siRNA duplex. Cleavage of the target RNA takes place in the middle of the region complementary to the antisense strand of the siRNA duplex. Studies have shown that 21 nucleotide siRNA duplexes are most active when containing two nucleotide 3'-overhangs. Furthermore, complete substitution of one or both siRNA strands with 2'-deoxy (2'-H) or 2'-O-methyl nucleotides abolishes RNAi activity, whereas substitution of the 3'-terminal siRNA overhang nucleotides with deoxy nucleotides (2'-H) has been reported to be tolerated.

Studies have shown that replacing the 3'-overhanging segments of a 21-mer siRNA duplex having 2 nucleotide 3' overhangs with deoxyribonucleotides does not have an adverse effect on RNAi activity. Replacing up to 4 nucleotides on each end of the siRNA with deoxyribonucleotides has been reported to be well tolerated whereas complete substitution with deoxyribonucleotides results in no RNAi activity.

Alternatively, the siNAs can be delivered as single or multiple transcription products expressed by a polynucleotide vector encoding the single or multiple siNAs and directing their expression within target cells. In these embodiments the double-stranded portion of a final transcription product of the siRNAs to be expressed within the target cell can be, for example, 15 to 49 bp, 15 to 35 bp, or about 21 to 30 bp long. Within exemplary embodiments, double-stranded portions of siNAs, in which two strands pair up, are not limited to completely paired nucleotide segments, and may contain nonpairing portions due to mismatch (the corresponding nucleotides are not complementary), bulge (lacking in the corresponding complementary nucleotide on one strand), overhang, and the like. Nonpairing portions can be contained to the extent that they do not interfere with siNA formation. In more detailed embodiments, a "bulge" may comprise 1 to 2 nonpairing nucleotides, and the double-stranded region of siNAs in which two strands pair up may contain from about 1 to 7, or about 1 to 5 bulges. In addition, "mismatch" portions contained in the double-stranded region of siNAs may be present in numbers from about 1 to 7, or about 1 to 5. Most often in the case of mismatches, one of the nucleotides is guanine, and the other is uracil. Such mismatching may be attributable, for example, to a mutation from C to T, G to A, or mixtures thereof, in a corresponding DNA coding for sense RNA, but other cause are also contemplated. Furthermore, in the present invention the double-stranded region of siNAs in which two strands pair up may contain both bulge and mismatched portions in the approximate numerical ranges specified.

The terminal structure of siNAs of the invention may be either blunt or cohesive (overhanging) as long as the siNA retains its activity to silence expression of target genes. The cohesive (overhanging) end structure is not limited only to the 3' overhang as reported by others. On the contrary, the 5' overhanging structure may be included as long as it is capable of inducing a gene silencing effect such as by RNAi. In addition, the number of overhanging nucleotides is not limited to reported limits of 2 or 3 nucleotides, but can be any number as long as the overhang does not impair gene silencing activity of the siNA. For example, overhangs may comprise from about 1 to 8 nucleotides, more often from about 2 to 4 nucleotides. The total length of siNAs having cohesive end structure is expressed as the sum of the length of the paired double-stranded portion and that of a pair comprising overhanging single-strands at both ends. For example, in the exemplary case of a 19 bp double-stranded RNA with 4 nucleotide overhangs at both ends, the total length is expressed as 23 bp. Furthermore, since the overhanging sequence may have low specificity to a target gene, it is not necessarily complementary (antisense) or identical (sense) to the target gene sequence. Furthermore, as long as the siNA is able to maintain its gene silencing effect on the target gene, it may contain low molecular weight structure (for example a natural RNA molecule such as tRNA, rRNA or viral RNA, or an artificial RNA molecule), for example, in the overhanging portion at one end.

In addition, the terminal structure of the siNAs may have a stem-loop structure in which ends of one side of the double-stranded nucleic acid are connected by a linker nucleic acid, e.g., a linker RNA. The length of the double-stranded region (stem-loop portion) can be, for example, 15 to 49 bp, often 15 to 35 bp, and more commonly about 21 to 30 bp long. Alternatively, the length of the double-stranded region that is a final transcription product of siNAs to be expressed in a target cell may be, for example, approximately 15 to 49 bp, 15 to 35 bp, or about 21 to 30 bp long. When linker segments are employed, there is no particular limitation in the length of the linker as long as it does not hinder pairing of the stem portion. For example, for stable pairing of the stem portion and suppression of recombination between DNAs coding for this portion, the linker portion may have a clover-leaf tRNA structure. Even if the linker has a length that would hinder pairing of the stem portion, it is possible, for example, to construct the linker portion to include introns so that the introns are excised during processing of a precursor RNA into mature RNA, thereby allowing pairing of the stem portion. In the case of a stem-loop siRNA, either end (head or tail) of RNA with no loop structure may have a low molecular weight RNA. As described above, these low molecular weight RNAs may include a natural RNA molecule, such as tRNA, rRNA or viral RNA, or an artificial RNA molecule.

The siNA can also comprise a single stranded polynucleotide having nucleotide sequence complementary to nucleotide sequence in a target nucleic acid molecule or a portion thereof (for example, where such siNA molecule does not require the presence within the siNA molecule of nucleotide sequence corresponding to the target nucleic acid sequence or a portion thereof), wherein the single stranded polynucleotide can further comprise a terminal phosphate group, such as a 5'-phosphate (see for example Martinez et al., *Cell.*, 110: 563-574 (2002) and Schwarz et al., *Molecular Cell,* 10: 537-568 (2002), or 5',3'-diphosphate.

As used herein, the term siNA molecule is not limited to molecules containing only naturally-occurring RNA or DNA, but also encompasses chemically-modified nucleotides and non-nucleotides. In certain embodiments, the short interfering nucleic acid molecules of the invention lack 2'-hydroxy (2'-OH) containing nucleotides. In certain embodiments short interfering nucleic acids do not require the presence of nucleotides having a 2'-hydroxy group for mediating RNAi and as such, short interfering nucleic acid molecules of the invention optionally do not include any ribonucleotides (e.g., nucleotides having a 2'-OH group). Such siNA molecules that do not require the presence of ribonucleotides within the siNA molecule to support RNAi can however have an attached linker or linkers or other attached or associated groups, moieties, or chains containing one or more nucleotides with 2'-OH groups. Optionally, siNA molecules can comprise ribonucleotides at about 5, 10, 20, 30, 40, or 50% of the nucleotide positions.

As used herein, the term siNA is meant to be equivalent to other terms used to describe nucleic acid molecules that are capable of mediating sequence specific RNAi, for example short interfering RNA (siRNA), double-stranded RNA (dsRNA), micro-RNA (mRNA), short hairpin RNA (shRNA), short interfering oligonucleotide, short interfering nucleic acid, short interfering modified oligonucleotide, chemically-modified siRNA, post-transcriptional gene silencing RNA (ptgsRNA), and others.

In other embodiments, siNA molecules for use within the invention may comprise separate sense and antisense sequences or regions, wherein the sense and antisense regions are covalently linked by nucleotide or non-nucleotide linker molecules, or are alternately non-covalently linked by ionic interactions, hydrogen bonding, van der waals interactions, hydrophobic intercations, and/or stacking interactions.

"Antisense RNA" is an RNA strand having a sequence complementary to a target gene mRNA, and thought to induce RNAi by binding to the target gene mRNA. "Sense RNA" has a sequence complementary to the antisense RNA, and annealed to its complementary antisense RNA to form siRNA. These antisense and sense RNAs have been conventionally synthesized with an RNA synthesizer.

As used herein, the term "RNAi construct" is a generic term used throughout the specification to include small interfering RNAs (siRNAs), hairpin RNAs, and other RNA species which can be cleaved in vivo to form siRNAs. RNAi constructs herein also include expression vectors (also referred to as RNAi expression vectors) capable of giving rise to transcripts which form dsRNAs or hairpin RNAs in cells, and/or transcripts which can produce siRNAs in vivo. Optionally, the siRNA include single strands or double strands of siRNA.

An siHybrid molecule is a double-stranded nucleic acid that has a similar function to siRNA. Instead of a double-stranded RNA molecule, an siHybrid is comprised of an RNA strand and a DNA strand. Preferably, the RNA strand is the antisense strand as that is the strand that binds to the target mRNA. The siHybrid created by the hybridization of the DNA and RNA strands have a hybridized complementary portion and preferably at least one 3'overhanging end.

siNAs for use within the invention can be assembled from two separate oligonucleotides, where one strand is the sense strand and the other is the antisense strand, wherein the antisense and sense strands are self-complementary (i.e. each strand comprises nucleotide sequence that is complementary to nucleotide sequence in the other strand; such as where the antisense strand and sense strand form a duplex or double stranded structure, for example wherein the double stranded region is about 19 base pairs). The antisense strand may comprise a nucleotide sequence that is complementary to a nucleotide sequence in a target nucleic acid molecule or a portion thereof, and the sense strand may comprise a nucleotide sequence corresponding to the target nucleic acid sequence or a portion thereof. Alternatively, the siNA can be assembled from a single oligonucleotide, where the self-complementary sense and antisense regions of the siNA are linked by means of a nucleic acid-based or non-nucleic acid-based linker(s).

Within additional embodiments, siNAs for intracellular delivery according to the methods and compositions of the invention can be a polynucleotide with a duplex, asymmetric duplex, hairpin or asymmetric hairpin secondary structure, having self-complementary sense and antisense regions, wherein the antisense region comprises a nucleotide sequence that is complementary to a nucleotide sequence in a separate target nucleic acid molecule or a portion thereof, and the sense region comprises a nucleotide sequence corresponding to the target nucleic acid sequence or a portion thereof.

Non-limiting examples of chemical modifications that can be made in an siNA include without limitation phosphorothioate internucleotide linkages, 2'-deoxyribonucleotides, 2'-O-methyl ribonucleotides, 2'-deoxy-2'-fluoro ribonucleotides, "universal base" nucleotides, "acyclic" nucleotides, 5-C-methyl nucleotides, and terminal glyceryl and/or inverted deoxy abasic residue incorporation. These chemical modifications, when used in various siNA constructs, are shown to preserve RNAi activity in cells while at the same time, dramatically increasing the serum stability of these compounds.

In a non-limiting example, the introduction of chemically-modified nucleotides into nucleic acid molecules provides a powerful tool in overcoming potential limitations of in vivo stability and bioavailability inherent to native RNA molecules that are delivered exogenously. For example, the use of chemically-modified nucleic acid molecules can enable a lower dose of a particular nucleic acid molecule for a given therapeutic effect since chemically-modified nucleic acid molecules tend to have a longer half-life in serum. Furthermore, certain chemical modifications can improve the bioavailability of nucleic acid molecules by targeting particular cells or tissues and/or improving cellular uptake of the nucleic acid molecule. Therefore, even if the activity of a chemically-modified nucleic acid molecule is reduced as compared to a native nucleic acid molecule, for example, when compared to an all-RNA nucleic acid molecule, the overall activity of the modified nucleic acid molecule can be greater than that of the native molecule due to improved stability and/or delivery of the molecule. Unlike native unmodified siNA, chemically-modified siNA can also minimize the possibility of activating interferon activity in humans.

The siNA molecules described herein, the antisense region of a siNA molecule of the invention can comprise a phosphorothioate internucleotide linkage at the 3'-end of said antisense region. In any of the embodiments of siNA molecules described herein, the antisense region can comprise about one to about five phosphorothioate internucleotide linkages at the 5'-end of said antisense region. In any of the embodiments of siNA molecules described herein, the 3'-terminal nucleotide overhangs of a siNA molecule of the invention can comprise ribonucleotides or deoxyribonucleotides that are chemically-modified at a nucleic acid sugar, base, or backbone. In any of the embodiments of siNA molecules described herein, the 3'-terminal nucleotide overhangs can comprise one or more universal base ribonucleotides. In any of the embodiments of siNA molecules described herein, the 3'-terminal nucleotide overhangs can comprise one or more acyclic nucleotides.

For example, in a non-limiting example, the invention features a chemically-modified short interfering nucleic acid (siNA) having about 1, 2, 3, 4, 5, 6, 7, 8 or more phosphorothioate internucleotide linkages in one siNA strand. In yet another embodiment, the invention features a chemically-modified short interfering nucleic acid (siNA) individually having about 1, 2, 3, 4, 5, 6, 7, 8 or more phosphorothioate internucleotide linkages in both siNA strands. The phosphorothioate internucleotide linkages can be present in one or both oligonucleotide strands of the siNA duplex, for example in the sense strand, the antisense strand, or both strands. The siNA molecules of the invention can comprise one or more phosphorothioate internucleotide linkages at the 3'-end, the 5'-end, or both of the 3'- and 5'-ends of the sense strand, the antisense strand, or both strands. For example, an exemplary siNA molecule of the invention can comprise about 1 to about 5 or more (e.g., about 1, 2, 3, 4, 5, or more) consecutive phosphorothioate internucleotide linkages at the 5'-end of the sense strand, the antisense strand, or both strands. In another non-limiting example, an exemplary siNA molecule of the invention can comprise one or more (e.g., about 1, 2, 3, 4, 5, 6, 7, 8, 9, 10, or more) pyrimidine phosphorothioate internucleotide linkages in the sense strand, the antisense strand, or both strands. In yet another non-limiting example, an exemplary siNA molecule of the invention can comprise one or more (e.g., about 1, 2, 3, 4, 5, 6, 7, 8, 9, 10, or more) purine phosphorothioate internucleotide linkages in the sense strand, the antisense strand, or both strands.

An siNA molecule may be comprised of a circular nucleic acid molecule, wherein the siNA is about 38 to about 70 (e.g., about 38, 40, 45, 50, 55, 60, 65, or 70) nucleotides in length having about 18 to about 23 (e.g., about 18, 19, 20, 21, 22, or 23) base pairs wherein the circular oligonucleotide forms a dumbbell shaped structure having about 19 base pairs and 2 loops.

A circular siNA molecule contains two loop motifs, wherein one or both loop portions of the siNA molecule is biodegradable. For example, a circular siNA molecule of the invention is designed such that degradation of the loop portions of the siNA molecule in vivo can generate a double-stranded siNA molecule with 3'-terminal overhangs, such as 3'-terminal nucleotide overhangs comprising about 2 nucleotides.

Modified nucleotides present in siNA molecules, preferably in the antisense strand of the siNA molecules, but also optionally in the sense and/or both antisense and sense strands, comprise modified nucleotides having properties or characteristics similar to naturally occurring ribonucleotides. For example, the invention features siNA molecules including modified nucleotides having a Northern conformation (e.g., Northern pseudorotation cycle, see for example Saenger, Principles of Nucleic Acid Structure, Springer-Verlag ed., 1984). As such, chemically modified nucleotides present in the siNA molecules of the invention, preferably in the antisense strand of the siNA molecules of the invention, but also optionally in the sense and/or both antisense and sense strands, are resistant to nuclease degradation while at the same time maintaining the capacity to mediate RNAi. Non-limiting examples of nucleotides having a northern configuration include locked nucleic acid (LNA) nucleotides (e.g., 2'-O, 4'-C-methylene-(D-ribofuranosyl) nucleotides); 2'-methoxyethoxy (MOE) nucleotides; 2'-methyl-thio-ethyl, 2'-deoxy-2'-fluoro nucleotides. 2'-deoxy-2'-chloro nucleotides, 2'-azido nucleotides, and 2'-O-methyl nucleotides.

The sense strand of a double stranded siNA molecule may have a terminal cap moiety such as an inverted deoxyabasic moiety, at the 3'-end, 5'-end, or both 3' and 5'-ends of the sense strand.

Non-limiting examples of conjugates include conjugates and ligands described in Vargeese et al., U.S. application Ser. No. 10/427,160, filed Apr. 30, 2003, incorporated by reference herein in its entirety, including the drawings. In another embodiment, the conjugate is covalently attached to the chemically-modified siNA molecule via a biodegradable linker. In one embodiment, the conjugate molecule is attached at the 3'-end of either the sense strand, the antisense strand, or both strands of the chemically-modified siNA molecule. In another embodiment, the conjugate molecule is attached at the 5'-end of either the sense strand, the antisense strand, or both strands of the chemically-modified siNA molecule. In yet another embodiment, the conjugate molecule is attached both the 3'-end and 5'-end of either the sense strand, the antisense strand, or both strands of the chemically-modified siNA molecule, or any combination thereof. In one embodiment, a conjugate molecule of the invention comprises a molecule that facilitates delivery of a chemically-modified siNA molecule into a biological system, such as a cell. In another embodiment, the conjugate molecule attached to the chemically-modified siNA molecule is a poly ethylene glycol, human serum albumin, or a ligand for a cellular receptor that can mediate cellular uptake. Examples of specific conjugate molecules contemplated by the instant invention that can be attached to chemically-modified siNA molecules are described in Vargeese et al., U.S. Patent Application Publication No. 20030130186, published Jul. 10, 2003, and U.S. Patent Application Publication No. 20040110296, published Jun. 10, 2004. The type of conjugates used and the extent of conjugation of siNA molecules of the invention can be evaluated for improved pharmacokinetic profiles, bioavailability, and/or stability of siNA constructs while at the same time maintaining the ability of the siNA to mediate RNAi activity. As such, one skilled in the art can screen siNA constructs that are modified with various conjugates to determine whether the siNA conjugate complex possesses improved properties while maintaining the ability to mediate RNAi, for example in animal models as are generally known in the art.

A siNA further may be further comprised of a nucleotide, non-nucleotide, or mixed nucleotide/non-nucleotide linker that joins the sense region of the siNA to the antisense region of the siNA. In one embodiment, a nucleotide linker can be a linker of >2 nucleotides in length, for example about 3, 4, 5, 6, 7, 8, 9, or 10 nucleotides in length. In another embodiment, the nucleotide linker can be a nucleic acid aptamer. By "aptamer" or "nucleic acid aptamer" as used herein is meant a nucleic acid molecule that binds specifically to a target molecule wherein the nucleic acid molecule has sequence that comprises a sequence recognized by the target molecule in its natural setting. Alternately, an aptamer can be a nucleic acid molecule that binds to a target molecule where the target molecule does not naturally bind to a nucleic acid. The target molecule can be any molecule of interest. For example, the aptamer can be used to bind to a ligand-binding domain of a protein, thereby preventing interaction of the naturally occurring ligand with the protein. This is a non-limiting example and those in the art will recognize that other embodiments can be readily generated using techniques generally known in the art. [See, for example, Gold et al, *Annu. Rev. Biochem.*, 64: 763 (1995); Brody and Gold, *J. Biotechnol.*, 74: 5 (2000); Sun, *Curr. Opin. Mol. Ther.*, 2:100 (2000); Kusser, *J. Biotechnol.*, 74: 27 (2000); Hermann and Patel, *Science* 287: 820 (2000); and Jayasena, *Clinical Chemistry*, 45: 1628. (1999)

A non-nucleotide linker may be comprised of an abasic nucleotide, polyether, polyamine, polyamide, peptide, carbohydrate, lipid, polyhydrocarbon, or other polymeric compounds (e.g. polyethylene glycols such as those having between 2 and 100 ethylene glycol units). Specific examples include those described by Seela and Kaiser, *Nucleic Acids Res.*, 18:6353 (1990) and *Nucleic Acids Res.*, 15:3113 (1987); Cload and Schepartz, *J. Am. Chem. Soc.*, 113:6324 (1991); Richardson and Schepartz, *J. Am. Chem. Soc.*, 113:5109 (1991); Ma et al., *Nucleic Acids Res.*, 21:2585 (1993) and *Biochemistry* 32:1751 (1993); Durand et al., *Nucleic Acids Res.*, 18:6353 (1990); McCurdy et al., *Nucleosides & Nucleotides*, 10:287 (1991); Jschke et al., Tetrahedron Lett., 34:301 (1993); Ono et al., *Biochemistry*, 30:9914 (1991); Arnold et al., International Publication No. WO 89/02439; Usman et al., International Publication No. WO 95/06731; Dudycz et al., International Publication No. WO 95/11910 and Ferentz and Verdine, *J. Am. Chem. Soc.*, 113:4000 (1991). A "non-nucleotide" further means any group or compound that can be incorporated into a nucleic acid chain in the place of one or more nucleotide units, including either sugar and/or phosphate substitutions, and allows the remaining bases to exhibit their enzymatic activity. The group or compound can be abasic in that it does not contain a commonly recognized nucleotide base, such as adenosine, guanine, cytosine, uracil or thymine, for example at the C1 position of the sugar.

The synthesis of a siNA molecule of the invention, which can be chemically-modified, comprises: (a) synthesis of two complementary strands of the siNA molecule; (b) annealing the two complementary strands together under conditions suitable to obtain a double-stranded siNA molecule. In another embodiment, synthesis of the two complementary strands of the siNA molecule is by solid phase oligonucleotide synthesis. In yet another embodiment, synthesis of the two complementary strands of the siNA molecule is by solid phase tandem oligonucleotide synthesis.

Oligonucleotides (e.g., certain modified oligonucleotides or portions of oligonucleotides lacking ribonucleotides) are synthesized using protocols known in the art, for example as described in Caruthers et al., 1992, Methods in Enzymology 211, 3-19, Thompson et al., International PCT Publication No. WO 99/54459, Wincott et al., 1995, Nucleic Acids Res. 23, 2677-2684, Wincott et al., 1997, Methods Mol. Bio., 74, 59, Brennan et al., 1998, Biotechnol Bioeng., 61, 33-45, and Brennan, U.S. Pat. No. 6,001,311. Synthesis of RNA, including certain siNA molecules of the invention, follows general procedures as described, for example, in Usman et al., 1987, J. Am. Chem. Soc., 109, 7845; Scaringe et al., 1990, Nucleic Acids Res., 18, 5433; and Wincott et al., 1995, Nucleic Acids Res. 23, 2677-2684 Wincott et al., 1997, Methods Mol. Bio., 74, 59.

Supplemental or complementary methods for delivery of nucleic acid molecules for use within then invention are described, for example, in Akhtar et al., *Trends Cell Bio.*, 2, 139 (1992); Delivery Strategies for Antisense Oligonucleotide Therapeutics, ed. Akhtar, 1995, Maurer et al., *Mol. Membr. Biol.*, 16: 129-140 (1999); Hofland and Huang, *Handb. Exp. Pharmacol.*, 137: 165-192 (1999); and Lee et al., *ACS Symp. Ser.*, 752: 184-192 (2000). Sullivan et al., International PCT Publication No WO 94/02595, further describes general methods for delivery of enzymatic nucleic acid molecules. These protocols can be utilized to supplement or complement delivery of virtually any nucleic acid molecule contemplated within the invention.

Nucleic acid molecules and polynucleotide delivery-enhancing polypeptides can be administered to cells by a variety of methods known to those of skill in the art, including, but not restricted to, administration within formulations that comprise the siNA and polynucleotide delivery-enhancing polypeptide alone, or that further comprise one or more additional components, such as a pharmaceutically acceptable carrier, diluent, excipient, adjuvant, emulsifier, buffer, stabilizer, preservative, and the like. In certain embodiments, the siNA and/or the polynucleotide delivery-enhancing polypeptide can be encapsulated in liposomes, administered by iontophoresis, or incorporated into other vehicles, such as hydrogels, cyclodextrins, biodegradable nanocapsules, bioadhesive microspheres, or proteinaceous vectors (see e.g., O'Hare and Normand, International PCT Publication No. WO 00/53722). Alternatively, a nucleic acid/peptide/vehicle combination can be locally delivered by direct injection or by use of an infusion pump. Direct injection of the nucleic acid molecules of the invention, whether subcutaneous, intramuscular, or intradermal, can take place using standard needle and syringe methodologies, or by needle-free technologies such as those described in Conry et al., *Clin. Cancer Res.*, 5: 2330-2337 (1999) and Barry et al., International PCT Publication No. WO 99/31262.

The compositions of the instant invention can be effectively employed as pharmaceutical agents. Pharmaceutical agents prevent, modulate the occurrence or severity of, or treat (alleviate one or more symptom(s) to a detectable or measurable extent) of a disease state or other adverse condition in a patient.

Thus within additional embodiments the invention provides pharmaceutical compositions and methods featuring the presence or administration of one or more polynucleic acid(s), typically one or more siNAs, combined, complexed, or conjugated with a polynucleotide delivery-enhancing polypeptide, optionally formulated with a pharmaceutically-acceptable carrier, such as a diluent, stabilizer, buffer, and the like.

The present invention satisfies additional objects and advantages by providing short interfering nucleic acid (siNA) molecules that modulate expression of genes associated with a particular disease state or other adverse condition in a subject. Typically, the siNA will target a gene that is expressed at an elevated level as a causal or contributing factor associated with the subject disease state or adverse condition. In this context, the siNA will effectively downregulate expression of the gene to levels that prevent, alleviate, or reduce the severity or recurrence of one or more associated disease symptoms. Alternatively, for various distinct disease models where expression of the target gene is not necessarily elevated as a consequence or sequel of disease or other adverse condition, down regulation of the target gene will nonetheless result in a therapeutic result by lowering gene expression (i.e., to reduce levels of a selected mRNA and/or protein product of the target gene). Alternatively, siNAs of the invention may be targeted to lower expression of one gene, which can result in upregulation of a "downstream" gene whose expression is negatively regulated by a product or activity of the target gene.

Within exemplary embodiments, the compositions and methods of the invention are useful as therapeutic tools to regulate expression of tumor necrosis factor-α (TNF-α) to treat or prevent symptoms of rheumatoid arthritis (RA). In this context the invention further provides compounds, compositions, and methods useful for modulating expression and activity of TNF-α by RNA interference (RNAi) using small nucleic acid molecules. In more detailed embodiments, the invention provides small nucleic acid molecules, such as short interfering nucleic acid (siNA), short interfering RNA (siRNA), double-stranded RNA (dsRNA), micro-RNA (mRNA), and short hairpin RNA (shRNA) molecules, and related methods, that are effective for modulating expression of TNF-α and/or TNF-α genes to prevent or alleviate symptoms of RA in mammalian subjects. Within these and related therapeutic compositions and methods, the use of chemically-modified siNAs will often improve properties of the modified siNAs in comparison to properties of native siNA molecules, for example by providing increased resistance to nuclease degradation in vivo, and/or through improved cellular uptake. As can be readily determined according to the disclosure herein, useful siNAs having multiple chemical modifications will retain their RNAi activity. The siNA molecules of the instant invention thus provide useful reagents and methods for a variety of therapeutic, diagnostic, target validation, genomic discovery, genetic engineering, and pharmacogenomic applications.

This siNAs of the present invention may be administered in any form, for example transdermally or by local injection (e.g., local injection at sites of psoriatic plaques to treat psoriasis, or into the joints of patients afflicted with psoriatic arthritis or RA). In more detailed embodiments, the invention provides formulations and methods to administer therapeutically effective amounts of siNAs directed against of a mRNA of TNF-α, which effectively down-regulate the TNF-α RNA and thereby reduce or prevent one or more TNF-α-associated inflammatory condition(s). Comparable methods and compositions are provided that target expression of one or more different genes associated with a selected disease condition in animal subjects, including any of a large number of genes whose expression is known to be aberrantly increased as a causal or contributing factor associated with the selected disease condition.

The siNA/polynucleotide delivery-enhancing polypeptide mixtures of the invention can be administered in conjunction with other standard treatments for a targeted disease condition, for example in conjunction with therapeutic agents effective against inflammatory diseases, such as RA or psoriasis. Examples of combinatorially useful and effective agents in this context include non-steroidal antiinflammatory drugs (NSAIDs), methotrexate, gold compounds, D-penicillamine, the antimalarials, sulfasalazine, glucocorticoids, and other TNF-α neutralizing agents such as infliximab and entracept.

Negatively charged polynucleotides of the invention (e.g., RNA or DNA) can be administered to a patient by any standard means, with or without stabilizers, buffers, and the like, to form a pharmaceutical composition. When it is desired to use a liposome delivery mechanism, standard protocols for formation of liposomes can be followed. The compositions of the present invention may also be formulated and used as tablets, capsules or elixirs for oral administration, suppositories for rectal administration, sterile solutions, suspensions for injectable administration, and the other compositions known in the art.

The present invention also includes pharmaceutically acceptable formulations of the compositions described herein. These formulations include salts of the above compounds, e.g., acid addition salts, for example, salts of hydrochloric, hydrobromic, acetic acid, and benzene sulfonic acid.

A pharmacological composition or formulation refers to a composition or formulation in a form suitable for administration, e.g., systemic administration, into a cell or patient, including for example a human. Suitable forms, in part, depend upon the use or the route of entry, for example oral, transdermal, or by injection. Such forms should not prevent the composition or formulation from reaching a target cell (i.e., a cell to which the negatively charged nucleic acid is desirable for delivery). For example, pharmacological compositions injected into the blood stream should be soluble. Other factors are known in the art, and include considerations such as toxicity.

By "systemic administration" is meant in vivo systemic absorption or accumulation of drugs in the blood stream followed by distribution throughout the entire body. Administration routes which lead to systemic absorption include, without limitation: intravenous, subcutaneous, intraperitoneal, inhalation, oral, intrapulmonary and intramuscular. Each of these administration routes expose the desired negatively charged polymers, e.g., nucleic acids, to an accessible diseased tissue. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation that can facilitate the association of drug with the surface of cells, such as, lymphocytes and macrophages is also useful. This approach may provide enhanced delivery of the drug to target cells by taking advantage of the specificity of macrophage and lymphocyte immune recognition of abnormal cells, such as cancer cells.

By "pharmaceutically acceptable formulation" is meant, a composition or formulation that allows for the effective distribution of the nucleic acid molecules of the instant invention in the physical location most suitable for their desired activity. Nonlimiting examples of agents suitable for formulation with the nucleic acid molecules of the instant invention include: P-glycoprotein inhibitors (such as Pluronic P85), which can enhance entry of drugs into the CNS [Jolliet-Riant and Tillement, *Fundam. Clin. Pharmacol.*, 13:16-26 (1999)]; biodegradable polymers, such as poly (DL-lactide-coglycolide) microspheres for sustained release delivery after intracerebral implantation (Emerich, D F et al., *Cell Transplant*, 8: 47-58 (1999)] (Alkermes, Inc. Cambridge, Mass.); and loaded nanoparticles, such as those made of polybutylcyanoacrylate, which can deliver drugs across the blood brain barrier and can alter neuronal uptake mechanisms (*Prog Neuropsychopharmacol Biol Psychiatry*, 23: 941-949, (1999)]. Other non-limiting examples of delivery strategies for the nucleic acid molecules of the instant invention include material described in Boado et al., *J. Pharm. Sci.*, 87:1308-1315 (1998); Tyler et al., *FEBS Lett.*, 421: 280-284 (1999); Parridge et al., *PNAS USA.*, 92: 5592-5596 (1995); Boado, *Adv. Drug Delivery Rev.*, 15: 73-107 (1995); Aldrian-Herrada et al., *Nucleic Acids Res.*, 26: 4910-4916 (1998); and Tyler et al, *PNAS USA.*, 96: 7053-7058 (1999).

The present invention also includes compositions prepared for storage or administration, which include a pharmaceutically effective amount of the desired compounds in a pharmaceutically acceptable carrier or diluent. Acceptable carriers or diluents for therapeutic use are well known in the pharmaceutical art, and are described, for example, in Remington's Pharmaceutical Sciences, Mack Publishing Co. (A. R. Gennaro edit. 1985). For example, preservatives, stabilizers, dyes and flavoring agents may be provided. These include sodium benzoate, sorbic acid and esters of p-hydroxybenzoic acid. In addition, antioxidants and suspending agents may be used.

A pharmaceutically effective dose is that dose required to prevent, inhibit the occurrence of, or treat (alleviate a symptom to some extent, preferably all of the symptoms) a disease state. The pharmaceutically effective dose depends on the type of disease, the composition used, the route of administration, the type of mammal being treated, the physical characteristics of the specific mammal under consideration, concurrent medication, and other factors that those skilled in the medical arts will recognize. Generally, an amount between 0.1 mg/kg and 100 mg/kg body weight/day of active ingredients is administered dependent upon potency of the negatively charged polymer.

Aqueous suspensions contain the active materials in admixture with excipients suitable for the manufacture of aqueous suspensions. Such excipients are suspending agents, for example sodium carboxymethylcellulose, methylcellulose, hydropropyl-methylcellulose, sodium alginate, polyvinylpyrrolidone, gum tragacanth and gum acacia; dispersing or wetting agents can be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions can also contain one or more preservatives, for example ethyl, or n-propyl p-hydroxybenzoate, one or more coloring agents, one or more flavoring agents, and one or more sweetening agents, such as sucrose or saccharin.

Oily suspensions can be formulated by suspending the active ingredients in a vegetable oil, for example arachis oil, olive oil, sesame oil or coconut oil, or in a mineral oil such as liquid paraffin. The oily suspensions can contain a thickening agent, for example beeswax, hard paraffin or cetyl alcohol. Sweetening agents and flavoring agents can be added to provide palatable oral preparations. These compositions can be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents or suspending agents are exemplified by those already mentioned above. Additional excipients, for example sweetening, flavoring and coloring agents, can also be present.

Pharmaceutical compositions of the invention can also be in the form of oil-in-water emulsions. The oily phase can be a vegetable oil or a mineral oil or mixtures of these. Suitable emulsifying agents can be naturally-occurring gums, for example gum acacia or gum tragacanth, naturally-occurring phosphatides, for example soy bean, lecithin, and esters or partial esters derived from fatty acids and hexitol, anhydrides, for example sorbitan monooleate, and condensation products of the said partial esters with ethylene oxide, for example polyoxyethylene sorbitan monooleate. The emulsions can also contain sweetening and flavoring agents.

The pharmaceutical compositions can be in the form of a sterile injectable aqueous or oleaginous suspension. This suspension can be formulated according to the known art using those suitable dispersing or wetting agents and suspending agents that have been mentioned above. The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid find use in the preparation of injectables.

The siNAs can also be administered in the form of suppositories, e.g., for rectal administration of the drug. These compositions can be prepared by mixing the drug with a suitable non-irritating excipient that is solid at ordinary temperatures but liquid at the rectal temperature and will therefore melt in the rectum to release the drug. Such materials include cocoa butter and polyethylene glycols.

The siNAs can be modified extensively to enhance stability by modification with nuclease resistant groups, for example, 2'-amino, 2'-C-allyl, 2'-fluoro, 2'-O-methyl, 2'-H. [For a review see Usman and Cedergren, *TIBS* 17: 34 (1992); Usman et al, *Nucleic Acids Symp. Ser.* 31: 163 (1994)]. SiNA constructs can be purified by gel electrophoresis using general methods or can be purified by high pressure liquid chromatography and re-suspended in water.

Chemically synthesizing nucleic acid molecules with modifications (base, sugar and/or phosphate) can prevent their degradation by serum ribonucleases, which can increase their potency. See e.g., Eckstein et al., International Publication No. WO 92/07065; Perrault et al., *Nature* 344: 565 (1990); Pieken et al., *Science* 253, 314 (1991); Usman and Cedergren, *Trends in Biochem. Sci.* 17: 334 (1992); Usman et al., International Publication No. WO 93/15187; and Rossi et al., International Publication No. WO 91/03162; Sproat, U.S. Pat. No. 5,334,711; Gold et al., U.S. Pat. No. 6,300,074. All of the above references describe various chemical modifications that can be made to the base, phosphate and/or sugar moieties of the nucleic acid molecules described herein.

There are several examples in the art describing sugar, base and phosphate modifications that can be introduced into nucleic acid molecules with significant enhancement in their nuclease stability and efficacy. For example, oligonucleotides are modified to enhance stability and/or enhance biological activity by modification with nuclease resistant groups, for example, 2'-amino, 2'-C-allyl, 2'-fluoro, 2'-O-methyl, 2'-O-allyl, 2'-H, nucleotide base modifications. For a review see Usman and Cedergren, *TIBS.* 17: 34 (1992); Usman et al., *Nucleic Acids Symp. Ser.* 31:163 (1994); Burgin et al., *Biochemistry,* 35: 14090 (1996). Sugar modification of nucleic acid molecules have been extensively described in the art. See Eckstein et al., International Publication PCT No. WO 92/07065; Perrault et al. *Nature,* 344, 565-568 (1990); Pieken et al. *Science,* 253: 314-317 (1991); Usman and Cedergren, *Trends in Biochem. Sci.,* 17: 334-339 (1992); Usman et al. International Publication PCT No. WO 93/15187; Sproat, U.S. Pat. No. 5,334,711 and Beigelman et al., 1995, *J. Biol. Chem.,* 270, 25702; Beigelman et al., International PCT publication No. WO 97/26270; Beigelman et al., U.S. Pat. No. 5,716,824; Usman et al., U.S. Pat. No. 5,627,053; Woolf et al., International PCT Publication No. WO 98/13526; Thompson et al., Karpeisky et al., *Tetrahedron Lett.,* 39: 1131 (1998); Earnshaw and Gait, *Biopolymers (Nucleic Acid Sciences),* 48: 39-55 (1998); Verma and Eckstein, *Annu. Rev. Biochem.,* 67: 99-134 (1998); and Burlina et al., *Bioorg. Med. Chem.,* 5: 1999-2010 (1997). Such publications describe general methods and strategies to determine the location of incorporation of sugar, base and/or phosphate modifications and the like into nucleic acid molecules without modulating catalysis. In view of such teachings, similar modifications can be used as described herein to modify the siNA nucleic acid molecules of the instant invention so long as the ability of siNA to promote RNAi in cells is not significantly inhibited.

While chemical modification of oligonucleotide internucleotide linkages with phosphorothioate, phosphorodithioate, and/or 5'-methylphosphonate linkages improves stability, excessive modifications can cause some toxicity or decreased activity. Therefore, when designing nucleic acid molecules, the amount of these internucleotide linkages should be minimized. The reduction in the concentration of these linkages should lower toxicity, resulting in increased efficacy and higher specificity of these molecules.

In one embodiment, the invention features modified siNA molecules, with phosphate backbone modifications comprising one or more phosphorothioate, phosphorodithioate, methylphosphonate, phosphotriester, morpholino, amidate carbamate, carboxymethyl, acetamidate, polyamide, sulfonate, sulfonamide, sulfamate, formacetal, thioformacetal, and/or alkylsilyl, substitutions. For a review of oligonucleotide backbone modifications, see Hunziker and Leumann, *Nucleic Acid Analogues: Synthesis and Properties, in Modern Synthetic Methods, VCH,* 331-417 (1995), and Mesmaeker et al., *Novel Backbone Replacements for Oligonucleotides, in Carbohydrate Modifications in Antisense Research, ACS,* 24-39 (1994).

Methods for the delivery of nucleic acid molecules are described in Akhtar et al., *Trends Cell Bio.,* 2: 139 (1992); *Delivery Strategies for Antisense Oligonucleotide Therapeutics,* ed. Akhtar, (1995), Maurer et al., *Mol. Membr. Biol.,* 16: 129-140 (1999); Hofland and Huang, *Handb. Exp. Pharmacol.,* 137: 165-192 (1999); and Lee et al., *ACS Symp. Ser.,* 752: 184-192 (2000). Beigelman et al., U.S. Pat. No. 6,395,713 and Sullivan et al., PCT WO 94/02595 further describe the general methods for delivery of nucleic acid molecules. These protocols can be utilized for the delivery of virtually any nucleic acid molecule. Nucleic acid molecules can be administered to cells by a variety of methods known to those of skill in the art, including, but not restricted to, encapsulation in liposomes, by iontophoresis, or by incorporation into other vehicles, such as biodegradable polymers, hydrogels, cyclodextrins (see for example Gonzalez et al., *Bioconjugate Chem.,* 10: 1068-1074 (1999); Wang et al., International PCT publication Nos. WO 03/47518 and WO 03/46185), poly (lactic-co-glycolic)ac-id (PLGA) and PLCA microspheres (see for example U.S. Pat. No. 6,447,796 and US Patent Application Publication No. US 2002130430), biodegradable nanocapsules, and bioadhesive microspheres, or by proteinaceous vectors (O'Hare and Normand, International PCT Publication No. WO 00/53722). Alternatively, the nucleic acid/vehicle combination is locally delivered by direct injection or by use of an infusion pump. Direct injection of the nucleic acid molecules of the invention, whether subcutaneous, intramuscular, or intradermal, can take place using standard needle and syringe methodologies, or by needle-free technologies such as those described in Conry et al., Clin. Cancer Res., 5: 2330-2337 (1999) and Barry et al., International PCT Publication No. WO 99/31262. The molecules of the instant invention can be used as pharmaceutical agents. Pharmaceutical agents prevent, modulate the occurrence, or treat (alleviate a symptom to some extent, preferably all of the symptoms) of a disease state in a subject.

The term "ligand" refers to any compound or molecule, such as a drug, peptide, hormone, or neurotransmitter, that is capable of interacting with another compound, such as a receptor, either directly or indirectly. The receptor that interacts with a ligand can be present on the surface of a cell or can alternately be an intercellular receptor. Interaction of the ligand with the receptor can result in a biochemical reaction, or can simply be a physical interaction or association.

By "asymmetric hairpin" as used herein is meant a linear siNA molecule comprising an antisense region, a loop portion that can comprise nucleotides or non-nucleotides, and a sense region that comprises fewer nucleotides than the antisense region to the extent that the sense region has enough complementary nucleotides to base pair with the antisense region and form a duplex with loop. For example, an asymmetric hairpin siNA molecule of the invention can comprise an antisense region having length sufficient to mediate RNAi in a T-cell (e.g. about 19 to about 22 (e.g., about 19, 20, 21, or 22) nucleotides) and a loop region comprising about 4 to about 8 (e.g., about 4, 5, 6, 7, or 8) nucleotides, and a sense region having about 3 to about 18 (e.g., about 3, 4, 5, 6, 7, 8, 9, 10, 11, 12, 13, 14, 15, 16, 17, or 18) nucleotides that are complementary to the antisense region. The asymmetric hairpin siNA molecule can also comprise a 5'-terminal phosphate group that can be chemically modified. The loop portion of the asymmetric hairpin siNA molecule can comprise nucleotides, non-nucleotides, linker molecules, or conjugate molecules as described herein.

By "asymmetric duplex" as used herein is meant a siNA molecule having two separate strands comprising a sense region and an antisense region, wherein the sense region comprises fewer nucleotides than the antisense region to the extent that the sense region has enough complementary nucleotides to base pair with the antisense region and form a duplex. For example, an asymmetric duplex siNA molecule of the invention can comprise an antisense region having length sufficient to mediate RNAi in a T-cell (e.g. about 19 to about 22 (e.g. about 19, 20, 21, or 22) nucleotides) and a sense region having about 3 to about 18 (e.g., about 3, 4, 5, 6, 7, 8, 9, 10, 11, 12, 13, 14, 15, 16, 17, or 18) nucleotides that are complementary to the antisense region.

By "modulate gene expression" is meant that the expression of a target gene is upregulated or downregulated, which can include upregulation or downregulation of mRNA levels present in a cell, or of mRNA translation, or of synthesis of protein or protein subunits, encoded by the target gene. Modulation of gene expression can be determined also be the presence, quantity, or activity of one or more proteins or protein subunits encoded by the target gene that is up regulated or down regulated, such that expression, level, or activity of the subject protein or subunit is greater than or less than that which is observed in the absence of the modulator (e.g., a siRNA). For example, the term "modulate" can mean "inhibit," but the use of the word "modulate" is not limited to this definition.

By "inhibit", "down-regulate", or "reduce" expression, it is meant that the expression of the gene, or level of RNA molecules or equivalent RNA molecules encoding one or more proteins or protein subunits, or level or activity of one or more proteins or protein subunits encoded by a target gene, is reduced below that observed in the absence of the nucleic acid molecules (e.g., siNA) of the invention. In one embodiment, inhibition, down-regulation or reduction with an siNA molecule is below that level observed in the presence of an inactive or attenuated molecule. In another embodiment, inhibition, down-regulation, or reduction with siNA molecules is below that level observed in the presence of, for example, an siNA molecule with scrambled sequence or with mismatches. In another embodiment, inhibition, down-regulation, or reduction of gene expression with a nucleic acid molecule of the instant invention is greater in the presence of the nucleic acid molecule than in its absence.

Gene "silencing" refers to partial or complete loss-of-function through targeted inhibition of gene expression in a cell and may also be referred to as "knock down". Depending on the circumstances and the biological problem to be addressed, it may be preferable to partially reduce gene expression. Alternatively, it might be desirable to reduce gene expression as much as possible. The extent of silencing may be determined by methods known in the art, some of which are summarized in International Publication No. WO 99/32619. Depending on the assay, quantitation of gene expression permits detection of various amounts of inhibition that may be desired in certain embodiments of the invention, including prophylactic and therapeutic methods, which will be capable of knocking down target gene expression, in terms of mRNA levels or protein levels or activity, for example, by equal to or greater than 10%, 30%, 50%, 75% 90%, 95% or 99% of baseline (i.e., normal) or other control levels, including elevated expression levels as may be associated with particular disease states or other conditions targeted for therapy.

The phrase "inhibiting expression of a target gene" refers to the ability of a siNA of the invention to initiate gene silencing of the target gene. To examine the extent of gene silencing, samples or assays of the organism of interest or cells in culture expressing a particular construct are compared to control samples lacking expression of the construct. Control samples (lacking construct expression) are assigned a relative value of 100%. Inhibition of expression of a target gene is achieved when the test value relative to the control is about 90%, often 50%, and in certain embodiments 25-0%. Suitable assays include, e.g., examination of protein or mRNA levels using techniques known to those of skill in the art such as dot blots, northern blots, in situ hybridization, ELISA, immunoprecipitation, enzyme function, as well as phenotypic assays known to those of skill in the art.

By "subject" is meant an organism, tissue, or cell, which may include an organism as the subject or as a donor or recipient of explanted cells or the cells that are themselves subjects for siNA delivery. "Subject" therefore may refers to an organism, organ, tissue, or cell, including in vitro or ex vivo organ, tissue or cellular subjects, to which the nucleic acid molecules of the invention can be administered and enhanced by polynucleotide delivery-enhancing polypeptides described herein. Exemplary subjects include mammalian individuals or cells, for example human patients or cells.

As used herein "cell" is used in its usual biological sense, and does not refer to an entire multicellular organism, e.g., specifically does not refer to a human. The cell can be present in an organism, e.g., birds, plants and mammals such as humans, cows, sheep, apes, monkeys, swine, dogs, and cats. The cell can be prokaryotic (e.g., bacterial cell) or eukaryotic (e.g., mammalian or plant cell). The cell can be of somatic or germ line origin, totipotent or pluripotent, dividing or non-dividing. The cell can also be derived from or can comprise a gamete or embryo, a stem cell, or a fully differentiated cell.

By "vectors" is meant any nucleic acid- and/or viral-based technique used to deliver a desired nucleic acid.

By "comprising" is meant including, but not limited to, whatever follows the word "comprising." Thus, use of the term "comprising" indicates that the listed elements are required or mandatory, but that other elements are optional and may or may not be present. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they affect the activity or action of the listed elements.

By "RNA" is meant a molecule comprising at least one ribonucleotide residue. By "ribonucleotide" is meant a nucleotide with a hydroxyl group at the 2' position of a .beta.-D-ribo-furanose moiety. The terms include double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution and/or alteration of one or more nucleotides. Such alterations can include addition of non-nucleotide material, such as to the end(s) of the siNA or internally, for example at one or more nucleotides of the RNA. Nucleotides in the RNA molecules of the instant invention can also comprise non-standard nucleotides, such as non-naturally occurring nucleotides or chemically synthesized nucleotides or deoxynucleotides. These altered RNAs can be referred to as analogs or analogs of naturally-occurring RNA.

By "highly conserved sequence region" is meant, a nucleotide sequence of one or more regions in a target gene does not vary significantly from one generation to the other or from one biological system to the other.

By "sense region" is meant a nucleotide sequence of a siNA molecule having complementarity to an antisense region of the siNA molecule. In addition, the sense region of a siNA molecule can comprise a nucleic acid sequence having homology with a target nucleic acid sequence.

By "antisense region" is meant a nucleotide sequence of a siNA molecule having complementarity to a target nucleic acid sequence. In addition, the antisense region of a siNA molecule can optionally comprise a nucleic acid sequence having complementarity to a sense region of the siNA molecule.

By "target nucleic acid" is meant any nucleic acid sequence whose expression or activity is to be modulated. The target nucleic acid can be DNA or RNA.

By "complementarity" is meant that a nucleic acid can form hydrogen bond(s) with another nucleic acid sequence by either traditional Watson-Crick or other non-traditional types. In reference to the nucleic molecules of the present invention, the binding free energy for a nucleic acid molecule with its complementary sequence is sufficient to allow the relevant function of the nucleic acid to proceed, e.g., RNAi activity. Determination of binding free energies for nucleic acid molecules is well known in the art (see, e.g., Turner et al., 1987, CSH Symp. Quant. Biol. LII pp. 123-133; Frier et al., 1986, Proc. Nat. Acad. Sci. USA 83:9373-9377; Turner et al., 1987, J. Am. Chem. Soc. 109:3783-3785). A percent complementarity indicates the percentage of contiguous residues in a nucleic acid molecule that can form hydrogen bonds (e.g., Watson-Crick base pairing) with a second nucleic acid sequence (e.g., 5, 6, 7, 8, 9, or 10 nucleotides out of a total of 10 nucleotides in the first oligonucleotide being based paired to a second nucleic acid sequence having 10 nucleotides represents 50%, 60%, 70%, 80%, 90%, and 100% complementary respectively). "Perfectly complementary" means that all the contiguous residues of a nucleic acid sequence will hydrogen bond with the same number of contiguous residues in a second nucleic acid sequence.

The term "universal base" as used herein refers to nucleotide base analogs that form base pairs with each of the natural DNA/RNA bases with little discrimination between them. Non-limiting examples of universal bases include C-phenyl, C-naphthyl and other aromatic derivatives, inosine, azole carboxamides, and nitroazole derivatives such as 3-nitropyrrole, 4-nitroindole, 5-nitroindole, and 6-nitroindole as known in the art (see for example Loakes, 2001, *Nucleic Acids Research*, 29, 2437-2447).

The term "acyclic nucleotide" as used herein refers to any nucleotide having an acyclic ribose sugar, for example where any of the ribose carbons (C1, C2, C3, C4, or C5), are independently or in combination absent from the nucleotide.

The term "biodegradable" as used herein, refers to degradation in a biological system, for example enzymatic degradation or chemical degradation.

The term "biologically active molecule" as used herein, refers to compounds or molecules that are capable of eliciting or modifying a biological response in a system. Non-limiting examples of biologically active siNA molecules either alone or in combination with other molecules contemplated by the instant invention include therapeutically active molecules such as antibodies, cholesterol, hormones, antivirals, peptides, proteins, chemotherapeutics, small molecules, vitamins, co-factors, nucleosides, nucleotides, oligonucleotides, enzymatic nucleic acids, antisense nucleic acids, triplex forming oligonucleotides, 2,5-A chimeras, siNA, dsRNA, allozymes, aptamers, decoys and analogs thereof. Biologically active molecules of the invention also include molecules capable of modulating the pharmacokinetics and/or pharmacodynamics of other biologically active molecules, for example, lipids and polymers such as polyamines, polyamides, polyethylene glycol and other polyethers.

The term "phospholipid" as used herein, refers to a hydrophobic molecule comprising at least one phosphorus group. For example, a phospholipid can comprise a phosphorus-containing group and saturated or unsaturated alkyl group, optionally substituted with OH, COOH, oxo, amine, or substituted or unsubstituted aryl groups.

By "cap structure" is meant chemical modifications, which have been incorporated at either terminus of the oligonucleotide (see, for example, Adamic et al., U.S. Pat. No. 5,998, 203, incorporated by reference herein). These terminal modifications protect the nucleic acid molecule from exonuclease degradation, and may help in delivery and/or localization within a cell. The cap may be present at the 5'-terminus (5'-cap) or at the 3'-terminal (3'-cap) or may be present on both termini. In non-limiting examples, the 5'-cap includes, but is not limited to, glyceryl, inverted deoxy abasic residue (moiety); 4',5'-methylene nucleotide; 1-(beta-D-erythrofuranosyl) nucleotide, 4'-thio nucleotide; carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety.

Non-limiting examples of the 3'-cap include, but are not limited to, glyceryl, inverted deoxy abasic residue (moiety), 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate; 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Iyer, 1993, Tetrahedron 49, 1925; incorporated by reference herein).

By the term "non-nucleotide" is meant any group or compound which can be incorporated into a nucleic acid chain in the place of one or more nucleotide units, including either sugar and/or phosphate substitutions, and allows the remaining bases to exhibit their enzymatic activity. The group or compound is abasic in that it does not contain a commonly recognized nucleotide base, such as adenosine, guanine, cytosine, uracil or thymine and therefore lacks a base at the 1'-position.

By "nucleotide" as used herein is as recognized in the art to include natural bases (standard), and modified bases well known in the art. Such bases are generally located at the 1' position of a nucleotide sugar moiety. Nucleotides generally comprise a base, sugar and a phosphate group. The nucleotides can be unmodified or modified at the sugar, phosphate and/or base moiety, (also referred to interchangeably as nucleotide analogs, modified nucleotides, non-natural nucleotides, non-standard nucleotides and other; see, for example, Usman and McSwiggen, supra; Eckstein et al., International PCT Publication No. WO 92/07065; Usman et al, International PCT Publication No. WO 93/15187; Uhlman & Peyman, supra, all are hereby incorporated by reference herein). There are several examples of modified nucleic acid bases known in the art as summarized by Limbach et al, 1994, Nucleic Acids Res. 22, 2183. Some of the non-limiting examples of base modifications that can be introduced into nucleic acid molecules include, inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), propyne, and others (Burgin et al., 1996, Biochemistry, 35, 14090; Uhlman & Peyman, supra). By "modified bases" in this aspect is meant nucleotide bases other than adenine, guanine, cytosine and uracil at 1' position or their equivalents.

By "target site" is meant a sequence within a target RNA that is "targeted" for cleavage mediated by a siNA construct which contains sequences within its antisense region that are complementary to the target sequence.

By "detectable level of cleavage" is meant cleavage of target RNA (and formation of cleaved product RNAs) to an extent sufficient to discern cleavage products above the background of RNAs produced by random degradation of the target RNA. Production of cleavage products from 1-5% of the target RNA is sufficient to detect above the background for most methods of detection.

By "biological system" is meant, material, in a purified or unpurified form, from biological sources, including but not limited to human, animal, plant, insect, bacterial, viral or other sources, wherein the system comprises the components required for RNAi activity. The term "biological system" includes, for example, a cell, tissue, or organism, or extract thereof. The term biological system also includes reconstituted RNAi systems that can be used in an in vitro setting.

The term "biodegradable linker" as used herein, refers to a nucleic acid or non-nucleic acid linker molecule that is designed as a biodegradable linker to connect one molecule to another molecule, for example, a biologically active molecule to a siNA molecule of the invention or the sense and antisense strands of a siNA molecule of the invention. The biodegradable linker is designed such that its stability can be modulated for a particular purpose, such as delivery to a particular tissue or cell type. The stability of a nucleic acid-based biodegradable linker molecule can be modulated by using various chemistries, for example combinations of ribonucleotides, deoxyribonucleotides, and chemically-modified nucleotides, such as 2'-O-methyl, 2'-fluoro, 2'-amino, 2'-O-amino, 2'-C-allyl, 2'-O-allyl, and other 2'-modified or base modified nucleotides. The biodegradable nucleic acid linker molecule can be a dimer, trimer, tetramer or longer nucleic acid molecule, for example, an oligonucleotide of about 2, 3, 4, 5, 6, 7, 8, 9, 10, 11, 12, 13, 14, 15, 16, 17, 18, 19, or 20 nucleotides in length, or can comprise a single nucleotide with a phosphorus-based linkage, for example, a phosphoramidate or phosphodiester linkage. The biodegradable nucleic acid linker molecule can also comprise nucleic acid backbone, nucleic acid sugar, or nucleic acid base modifications.

By "abasic" is meant sugar moieties lacking a base or having other chemical groups in place of a base at the 1' position, see for example Adamic et al., U.S. Pat. No. 5,998, 203.

By "unmodified nucleoside" is meant one of the bases adenine, cytosine, guanine, thymine, or uracil joined to the 1' carbon of .beta.-D-ribo-furanose.

By "modified nucleoside" is meant any nucleotide base which contains a modification in the chemical structure of an unmodified nucleotide base, sugar and/or phosphate. Non-limiting examples of modified nucleotides are shown by Formulae I-VII and/or other modifications described herein.

In connection with 2'-modified nucleotides as described for the present invention, by "amino" is meant 2'-NH$_2$ or 2'-O—NH$_2$, which can be modified or unmodified. Such modified groups are described, for example, in Eckstein et al., U.S. Pat. No. 5,672,695 and Matulic-Adamic et al., U.S. Pat. No. 6,248,878.

The siNA molecules can be complexed with cationic lipids, packaged within liposomes, or otherwise delivered to target cells or tissues. The nucleic acid or nucleic acid complexes can be locally administered to through injection, infusion pump or stent, with or without their incorporation in biopolymers. In another embodiment, polyethylene glycol (PEG) can be covalently attached to siNA compounds of the present invention, to the polynucleotide delivery-enhancing polypeptide, or both. The attached PEG can be any molecular weight, preferably from about 2,000 to about 50,000 daltons (Da).

The sense region can be connected to the antisense region via a linker molecule, such as a polynucleotide linker or a non-nucleotide linker.

"Inverted repeat" refers to a nucleic acid sequence comprising a sense and an antisense element positioned so that they are able to form a double stranded siRNA when the repeat is transcribed. The inverted repeat may optionally include a linker or a heterologous sequence such as a self-cleaving ribozyme between the two elements of the repeat. The elements of the inverted repeat have a length sufficient to form a double stranded RNA. Typically, each element of the inverted repeat is about 15 to about 100 nucleotides in length, preferably about 20-30 base nucleotides, preferably about 20-25 nucleotides in length, e.g., 20, 21, 22, 23, 24, 25, 26, 27, 28, 29, or 30 nucleotides in length.

"Nucleic acid" refers to deoxyribonucleotides or ribonucleotides and polymers thereof in single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

"Large double-stranded RNA" refers to any double-stranded RNA having a size greater than about 40 base pairs (bp) for example, larger than 100 bp or more particularly larger than 300 bp. The sequence of a large dsRNA may represent a segment of a mRNA or the entire mRNA. The maximum size of the large dsRNA is not limited herein. The double-stranded RNA may include modified bases where the modification may be to the phosphate sugar backbone or to the nucleoside. Such modifications may include a nitrogen or sulfur heteroatom or any other modification known in the art.

The double-stranded structure may be formed by self-complementary RNA strand such as occurs for a hairpin or a micro RNA or by annealing of two distinct complementary RNA strands.

"Overlapping" refers to when two RNA fragments have sequences which overlap by a plurality of nucleotides on one strand, for example, where the plurality of nucleotides (nt) numbers as few as 2-5 nucleotides or by 5-10 nucleotides or more.

"One or more dsRNAs" refers to dsRNAs that differ from each other on the basis of sequence.

"Target gene or mRNA" refers to any gene or mRNA of interest. Indeed any of the genes previously identified by genetics or by sequencing may represent a target. Target genes or mRNA may include developmental genes and regulatory genes as well as metabolic or structural genes or genes encoding enzymes. The target gene may be expressed in those cells in which a phenotype is being investigated or in an organism in a manner that directly or indirectly impacts a phenotypic characteristic. The target gene may be endogenous or exogenous. Such cells include any cell in the body of an adult or embryonic animal or plant including gamete or any isolated cell such as occurs in an immortal cell line or primary cell culture.

In this specification and the appended claims, the singular forms of "a", "an" and "the" include plural reference unless the context clearly dictates otherwise.

Example 1

Production and Characterization of Compositions Comprising a siRNA Complexed with a Polynucleotide Delivery-Enhancing Polypeptide To form complexes between candidate siRNAs and polynucleotide delivery-enhancing polypeptides of the invention, an adequate amount of siRNA is combined with a pre-determined amount of polynucleotide delivery-enhancing polypeptide, for example in Opti-MEM® cell medium (Invitrogen), in defined ratios and incubated at room temperature for about 10-30 min. Subsequently a selected volume, e.g., about 50 µl, of this mixture is brought into contact with target cells and the cells are incubated for a predetermined incubation period, which in the present example was about 2 hr. The siNA/peptide mixture can optionally include cell culture medium or other additives such as fetal bovine serum. For H3, H4 and H2b, a series of experiments was performed to complex these polynucleotide delivery-enhancing polypeptides with siRNA in different ratios. Generally this was initiated with a 1:0.01 to 1:50 of siRNA/histone ratio. To each well in a 96-well microtiter plate, 40 pm siRNA was added. Each well contained beta-gal cells at 50% confluency. Exemplary optimized ratios for transfection efficiency are shown in Table 2 below.

Transfections were performed with either regular siRNA or siRNA complexed with one of the above-identified histone proteins on 9 L/beta-gal cells. The siRNA was designed to specifically knock down beta-galactosidase mRNA, and activities are expressed as percentage of beta-gal activities from control (control cells were transfected using lipofectamine without the polynucleotide delivery-enhancing polypeptide).

Assays for detecting and/or quantifying the efficiency of siRNA delivery are carried out using conventional methods, for example beta-galactosidase assay or flow cytometry methods.

For beta-galactosidase assays, 9 L/LacZ cells, a cell line constitutively expressing beta-galactosidase, were used, and the siRNA against beta-gal mRNA was chemically synthesized and used with delivery reagents to evaluate knock-down efficiency.

Transfection Procedure

On the first day of the procedure, saturated 9 L/LacZ cultures are taken from T75 flasks, and the cells are detached and diluted into 10 ml of complete medium (DMEM, 1×PS, 1×Na Pyruvate, 1×NEAA). The cells are further diluted to 1:15, and 100 µl of this preparation are aliquoted into wells of 96 well plates, which will generally yield about 50% cell confluence by the next day for the transfection. Edges of the wells are left empty and filled with 250 µl water, and the plates are placed un-stacked in the incubator overnight at 37° C. (5% $CO_2$ incubator).

On the second day, the transfection complex is prepared in Opti-MEM, 50 µl each well. The medium is removed from the plates, and the wells are washed once with 200 µl PBS or Opti-MEM. The plates are blotted and dried completely with tissue by inversion. The transfection mixture is then added (50 µl/well) into each well, and 250 µl water is added to the wells on the edge to prevent them from drying. The cells are then incubated for at least 3 hours at 37° C. (5% $CO_2$ incubator). The transfection mixture is removed and replaced with 100 µl of complete medium (DMEM, 1×PS, 1×Na Pyruvate, 1×NEAA). The cells are cultured for a defined length of time, and then harvested for the enzyme assay.

Enzymatic Assay

Reagents for the enzymatic assay were purchased from Invitrogen (β-Gal Assay Kit, Catalog no.), and Fisher (Pierce Micro BCA Protein Assay Reagent Kit, Catalog).

A: Cell Lysis

Remove the medium, wash once with 200 μl PBS, blot the plate dry with inversion.

Add 30 μl lysis buffer from β-Gal Kit into each well.

Freeze-Thaw the cells twice to generate lysate.

B: β-Gal assay

Prepare assay mix (50 μl 1× buffer, 17 μl ONPG each well)

Take new plate, add 65 μl assay mix into each well.

Add 10 μl of cell lysate into each well. There should be blank wells for subtraction of the background activities.

Incubate at 37° C. for about 20 minutes, prevent long incubation which will use up ONPG and biase the high expression.

Add 100 μl of the Stop solution.

Measure the OD at 420 nm.

C: BCA Assay

Prepare BSA standard (150 ul per well), points should be duplicated on each plate.

Put 145 μl of water into each well, add 5 μl of cell lyaste into each well.

Prepare final Assay Reagent according to manufacture's instruction.

Add 150 μl of Assay Reagent into each well.

Incubate at 37° C. for about 20 minutes.

Measure the OD at 562 nm.

D: Calculation of Specific Activity

The specific activity is expressed as nmol of ONPG hydrolyzed/t/mg protein, where t is the time of incubation in minutes at 37° C.; mg protein is the protein assayed which is determined by BCA method.

Flow Cytometry Measurement of FITC/FAM Conjugated siRNA a) After exposure to the complex of siRNA/peptide, cells were incubated for at least 3 hours.

b) Wash cells with 200 μl PBS.

c) Detach cells with 15 μl TE, incubate at 37° C.

d) Resuspend cells in five wells with 30 μl FACS solution (PBS with 0.5% BSA, and 0.1% sodium Azide).

e) Combine all five wells into a tube.

f) Add PI (Propidium iodide) 5 μl into each tube.

g) Analyze the cells with fluorescence activated cell sorting (FCAS) according to manufacturer's instructions.

The siRNA sequence used to silence the beta-galactosidase mRNA was the following:

```
                                               (SEQ ID NO: 32)
C.U.A.C.A.C.A.A.A.U.C.A.G.C.G.A.U.U.U.dT.dT (Sense)

(SEQ ID NO: 33)
A.A.A.U.C.G.C.U.G.A.U.U.U.G.U.G.U.A.G.dT.dT (Antisense)
```

TABLE 2

Efficiency of siRNA delivery mediated by polynucleotide delivery-enhancing polypeptides

| Peptides | Delivery efficiency (% of total cells) | Molar ratio: (siRNA:peptide) |
| --- | --- | --- |
| siRNA (40 pmol/well) | 0.09 | |
| Cationic lipids (Invitrogen) | 84.32 | unknown |
| Histone H2B | 62.03 | 1:10-15 |
| Histone H3 | 85.08 | 1:10-20 |
| Histone H4 | 72.07 | 1:4-8 |
| GEQIAQLIAGYIDIILKKKKSK (SEQ ID NO: 31) | 50.86 | 1:5-20 |
| WWETWKPFQCRICMRNFSTRQARRNHRRRHR (SEQ ID NO: 27) | 98.29 | 1:0.5-4 |
| Poly Lys-Trp, 4:1, MW 20,000-50,000 | 71.92 | 1:2-8 |
| Poly Orn-Trp, 4:1, MW 20,000-50,000 | 74.16 | 1:2-8 | siRNA/Peptide/Lipids

To evaluate the effects of adding a cationic lipid to a siNA/polynucleotide delivery-enhancing polypeptide mixture, complex or conjugate, the above procedures were followed except the lipofectamine (Invitrogen) was added to siNA/polynucleotide delivery formulation in constant concentrations, following manufacturer's instructions (0.2 gμ/100 μl Opti-MEM).

To produce the composition comprised of GKINLKA-LAALAKKIL (SEQ ID NO: 28), siRNA and LIPOFECTIN® (Invitrogen), the siRNA and peptide were mixed together first in Opti-MEM cell culture medium at room temperature, after which LIPOFECTIN® was added at room temperature to the mixture to form the siRNA/peptide/cationic lipid composition.

To produce the composition comprised of RVIRVW-FQNKRCKDKK (SEQ ID NO: 29), siRNA and LIPOFECTIN®, the peptide and the LIPOFECTIN® were mixed together first in Opti-MEM cell culture medium, into this mixture was added the siRNA to form the siRNA/peptide/LIPOFECTIN® composition.

To produce the siRNA/peptide/cationic lipid composition using GRKKRRQRRRPPQGRKKRRQRRRP-PQGRKKRRQRRRPPQ (SEQ ID NO: 30) or GEQIAQLIAGYIDIILKKKKSK (SEQ ID NO: 31) it does not matter in which order the components are added together to produce the siRNA/peptide/cationic lipid composition.

To produce the siRNA/mellitin/LIPOFECTIN®, the siRNA and mellitin were first mixed together in Opti-MEM cell culture medium and then the LIPOFECTIN® was added to the mixture.

To produce the siRNA/histone H1/LIPOFECTIN® composition, the histone H1 and LIPOFECTIN® were first added together in Opti-MEM cell culture medium thoroughly mixed and then the siRNA was added, thoroughly and mixed with the histone LIPOFECTIN® mixture to form the siRNA/histone H1/LIPOFECTIN® composition.

TABLE 3

Efficiency of siRNA delivery mediated by polynucleotide delivery-enhancing polypeptides with and without cationic lipid

| Peptides | Delivery efficiency with lipids (% of total cells) | Delivery efficiency w/o lipids (% of total cells) | siRNA: Peptide ratio added in transfection mixture |
|---|---|---|---|
| siRNA only | 1.72 | 0.11 | |
| Lipofectamine | 83.48 | | |
| GKINLKALAALAKKIL (SEQ ID NO: 28) | 89.67 | 0.26 | 1:5-20 |
| RVIRVWFQNKRCKDKK (SEQ ID NO: 29) | 89 | 0.59 | 1:1-5 |
| GRKKRRQRRRPPQGRKKRRQ RRRPPQGRKKRRQRRRPPQ (SEQ ID NO: 30) | 89.99 | 54.58 | 1:5 |
| GEQIAQLIAGYIDIILKKKKSK (SEQ ID NO: 31) | 90.01 | 50.86 | 1:5-10 |
| Mellitin | 93.1 | 5.15 | 1:20 |
| Histone H1 | 93.39 | 0.14 | 1:10-20 |

Based on the foregoing results, it is apparent that exemplary polynucleotide delivery-enhancing polypeptides of the invention can substantially induce or enhance cellular uptake of siNAs, while the addition of an optional cationic lipid to certain siNA/polypeptide mixtures of the invention may substantially improve siNA delivery efficiency.

Example 2

Production and Characterization of Compositions Comprising a siRNA Conjugated with a TAT-HA Polynucleotide Delivery-Enhancing Polypeptide The present example describes the synthesis and uptake activity of specific peptides covalently conjugated to one strand of a siRNA duplex. These conjugates efficiently deliver siRNA into the cytoplasm and mediate knockdown of desired target genes.

Peptide Synthesis

Peptides were synthesized by solid-phase Fmoc chemistry on CLEAR-amide resin using a Rainin Symphony synthesizer. Coupling steps were performed using 5 equivalents of HCTU and Fmoc amino acid with an excess of N-methylmorpholine for 40 minutes. Fmoc removal was accomplished by treating the peptide resin with 20% piperidine in DMF for two 10 minutes cycles. Upon completion of the entire peptide, the Fmoc group was removed with piperidine and washed extensively with DMF. Maleimido modified peptides were prepared by coupling 3.0 equivalents of 3-maleimidopropionic acid and HCTU in the presence of 6 equivalents of N-methylmorpholine to the N-terminus of the peptide resin. The extent of coupling was monitored by the Kaiser test. The peptides were cleaved from the resin by the addition of 10 mL of TFA containing 2.5% water and 2.5 triisopropyl silane followed by gentle agitation at room temperature for 2 h. The resulting crude peptide was collected by trituration with ether followed by filtration. The crude product was dissolved in Millipore water and lyophilized to dryness. The crude peptide was taken up in 15 mL of water containing 0.05% TFA and 3 mL acetic acid and loaded onto a Zorbax RX-C8 reversed-phase (22 mm ID×250 mm, 5 µm particle size) through a 5 mL injection loop at a flow rate of 5 mL/min. The purification was accomplished by running a linear AB gradient of 0.1% B/min where solvent A is 0.05% TFA in water and solvent B is 0.05% TFA in acetonitrile. The purified peptides were analyzed by HPLC and ESMS.

Synthesis of Conjugates

Both peptides and RNA are prepared using standard solid phase synthesis methods. The peptide and RNA molecules must be functionalized with specific moieties to allow for covalent attachment to each other. For the peptide, the N-terminus is functionalized, for example, with 3-maleimidopropionic acid. However, it is recognized that other functional groups such as bromo or iodoacetyl moieties will work as well. For the RNA molecule the 5' end of the sense strand or 3' end of the antisense strand is functionalized with, for example, a 1-O-dimethoxytrityl-hexyl-disulfide linker according to the following synthetic method.

The 5 modified C6SS-oligonucleotide (GCAAGCUGAC-CCUGAAGUUCAU SEQ ID NO: 34; 3.467 mg; 0.4582 µmol) was reduced to the free thiol group with 0.393 mg (3 eq) of tris(2-cart)oxyethyl)phosphine (TCEP) in 0.3 ml of 0.1 M triethylamine acetate (TEAA) buffer (pH 7.0) at room temperature for 3 h. The reduced oligonucleotide was purified by RP HPLC on XTerra® MS $C_{18}$ 4.6×50 mm column using a linear gradient from 0-30% of $CH_3CN$ in 0.1M TEAA buffer pH 7 within 20 min ($t_r$=5.931 min).

Purified reduced oligonucleotide (1.361 mg, 0.19085 µmol) was dissolved in 0.2 ml of 0.1 µM TEAA buffer pH=7 and then the peptide with the maleimido moiety attached to the peptide N-terminus (0.79 mg, 1.5 eq) was added to the oligonucleotide solution. After addition of peptide a precipitate immediately formed which disappeared upon the addition of 150 µl of 75% $CH_3CN$/0.1M TEAA. After stirring overnight at room temperatures the resulting conjugate was purified by RP HPLC on XTerra® MS $C_{18}$ 4.6×50 mm column using a linear gradient from 0-30% of $CH_3CN$ in 0.1M TEAA buffer pH 7 within 20 min and 100% C within next 5 min ($t_r$=21.007 min). The amount of the conjugate was determined spectrophotometrically based on the calculated molar absorption coefficient at λ=260 nm. MALDI mass spectrometric analysis showed that the peak observed for the conjugate (10 585.3 amu) matches the calculated mass. Yield: 0.509 mg, 004815 µmol, 25.2%.

The peptide conjugate sense strand and complimentary antisense strand were annealed in 50 mM potassium acetate, 1 mM magnesium acetate and 15 mM HEPES pH 7.4 by heating at 90° C. for 2 min followed by incubation at 37° C. for 1 h. The formation of the double stranded RNA conjugate was confirmed by non denaturing (15%) polyacrylamide gel electrophoresis and staining with ethidium bromide.

Structure of the Peptide-siRNA Conjugate (SEQ ID NOS: 34 and 35)

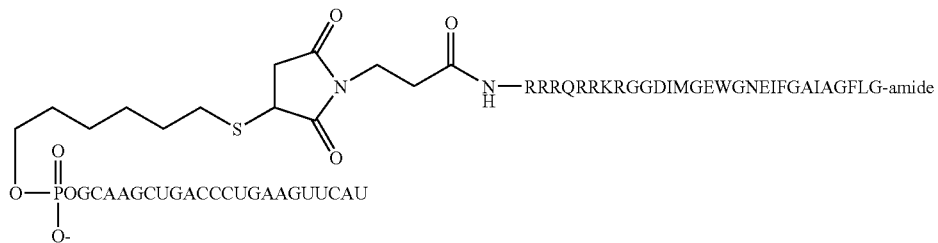

Uptake Experiments

Cells were plated the day before in 24-well plates so that they were ~50-80% confluent at time of transfection. For complexes, siRNA and peptide were diluted in Opti-MEM® media (Invitrogen), then mixed and allowed to complex 5-10 minutes before adding to cells washed with PBS. Final concentration of siRNA was 500 nM at each peptide concentration (2-50 μM). The conjugate, also diluted in Opti-MEM® media, was added to cells at final concentrations ranging from 62.5 nM to 500 nM. At 500 nM concentration, we also combined with 20% FBS just before adding to washed cells. Cells were transfected for 3 hours at 37° C., 5% $CO_2$. Cells were washed with PBS, treated with trypsin and then analyzed by flow cytometry. siRNA uptake was measured by intensity of Cy5 fluorescence and cellular viability assessed by addition of propidium iodide.

Figure 2:
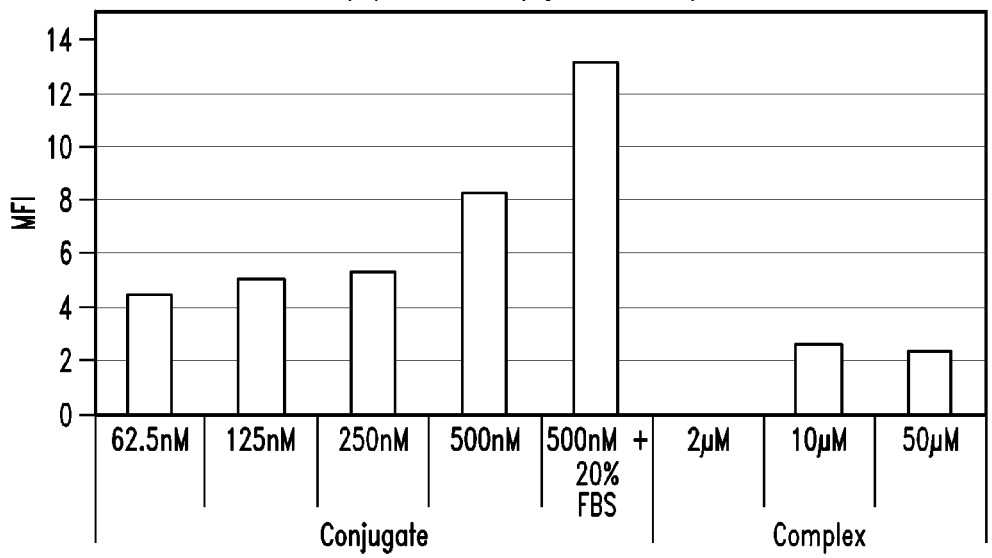
FIG. 2 further illustrates peptide-mediated uptake of siNAs complexed or conjugated to a polynucleotide delivery-enhancing polypeptide of the invention (SEQ ID NO: 35).

As shown in FIGS. 1 and 2, higher uptake and greater mean fluorescence uptake are observed for the conjugate compared to simply complexing the peptide and RNA. This indicates that in certain embodiments it will be desirable to conjugate the polynucleotide delivery-enhancing polypeptide to the siNA molecule.

Example 3

Screening of siRNA/Delivery Peptide Complexes Demonstrates Efficient Induction of siRNA Uptake in 9 L/LacZ Cells by a Diverse Assemblage of Rationally-Designed Polynucleotide Delivery-Enhancing Polypeptides The present example provides additional evidence that a broad and diverse assemblage of rationally-designed polynucleotide delivery-enhancing polypeptides of the invention induce or enhance siRNA uptake when complexed with siRNAs Approximately 10,000 9 L/lacZ cells were plated per well in flat-bottom 96-well plates so that they would be ~50% confluent the next day at the time of transfection. FAM-labeled siRNA and peptides were diluted in Opti-MEM® media (Invitrogen) at 2-fold the final concentration. Equal volumes of siRNA and peptide were mixed and allowed to complex 5-10 minutes at room temperature and then 50 μL added to cells, previously washed with PBS. Cells were transfected for 3 hours at 37° C., 5% $CO_2$. Cells were washed with PBS, treated with trypsin and then analyzed by flow cytometry. siRNA uptake was measured by intensity of FAM fluorescence and cellular viability assessed by addition of propidium iodide. The results of these screening assays are illustrated in Table 4 below.

TABLE 4

Efficiency of siRNA delivery mediated by rationally-designed polynucleotide delivery-enhancing polypeptides

| PN # | Sequence | Peptide Conc. | siRNA Conc. | % Uptake (%PI-/FAM+) |
|---|---|---|---|---|
| PN173 | GRKKRRQRRRPPQC (SEQ ID NO: 36) | 10μM | 400nM | 84.8 |
| PN227 | Maleimide-AAVALLPAVLLALLAPRKKRRQRRRPPQ-amide (SEQ ID NO 37:) | 1μM | 400nM | 31.0 |
| PN27 | AAVALLPAVLLALLAPRKKRRQRRRPPQC (SEQ ID NO: 38) | 1μM | 400nM | 82.6 |
| PN275 | Maleimide-AAVALLPAVLLALLAPRKKRRQRRRPPQ-amide (SEQ ID NO:37) | 4μM | 400nM | 95.3 |
| PN28 | NH2-RKKRRQRRRPPQCAAVALLPAVLLALLAP-amide (SEQ ID NO: 39) | 2μM | 400nM | 79.3 |
| PN69 | BrAc-GRKKRRQRRRPQ-amide (SEQ ID NO: 40) | 80μM | 400nM | 0.0 |
| PN81 | BrAc-RRRQRRKRGGDIMGEWGNEIFGAIAGFLG-amide (SEQ ID NO: 41) | 8μM | 800nM | 97.9 |
| PN250 | NH2-RRRQRRKRGGDIMGEWGNEIFGAIAGFLG-amide (SEQ ID NO: 35) | 15μM | 800nM | 99.5 |

TABLE 4-continued

Efficiency of siRNA delivery mediated by rationally-designed polynucleotide delivery-enhancing polypeptides

| PN # | Sequence | Peptide Conc. | siRNA Conc. | % Uptake (%PI-/FAM+) |
|---|---|---|---|---|
| PN204 | C(YGRKKRRQRRRG)₂ (SEQ ID NO: 42) | 1.4 µM | 800nM | 82.5 |
| PN280 | Maleimide-GRKKRRQRRRPPQ-amide (SEQ ID NO: 43) | 80 µM | 400nM | 7.9 |
| PN350 | NH2-KLWKAWPKLWKKLWKP-amide (SEQ ID NO: 44) | 10 µM | 400nM | 0.0 |
| PN365 | AAVALLPAVLLALLAPRRRRRR-amide (SEQ ID NO: 45) | 10 µM | 400nM | 81.4 |
| PN366 | RLWRALPRVLRRLLRP-amide (SEQ ID NO: 46) | 10 µM | 400nM | 0.0 |
| PN29 | NH2-AAVALLPAVLLALLAPSGASGLDKRDYV-amide (SEQ ID NO: 47) | 80 µM | 400nM | 86.5 |
| PN235 | Maleimide-AAVALLPAVLLALLAPSGASGLDKRDYV-amide (SEQ ID NO: 48) | 80 µM | 400nM | 0.0 |
| PN30 | NH2-SGASGLDKRDYVAAVAALLPAVLLALLAP-amide (SEQ ID NO: 49) | 80 µM | 400nM | 0.0 |
| PN202 | NH2-LLETLLKPFQCRICMRNFSTRQARRNHRRRHRR-amide (SEQ ID NO: 50) | 2 µM | 400nM | 70.8 |
| PN225 | NH2-AAVACRICMRNFSTRQARRNHRRRHRR-amide (SEQ ID NO: 51) | 2 µM | 400nM | 30.9 |
| PN236 | Maleimide-RQIKIWFQNRRMKWKK-amide (SEQ ID NO: 52) | 10 µM | 400nM | 37.7 |
| PN58 | RQIKIWFQNRRMKWKK amide (SEQ ID NO: 53) | 40 µM | 400nM | 75.8 |
| PN251 | NH2-RQIKIWFQNRRMKWKKDIMGEWGNEIFGAIAGFLG-amide (SEQ ID NO: 54) | 4 µM | 400nM | 44.5 |
| PN279 | Maleimide-SGRGKQGGKARAKAKTRSSRAGLQFPVGRVHRLLRKG-amide (SEQ ID NO: 55) | 40 µM | 400nM | 24.7 |
| PN61 | SGRGKQGGKARAKAKTRSSRAGLQFPVGRVHRLLRKGC-amid (SEQ ID NO: 56) | 80µM | 800nM | 86.8 |
| PN360 | KGSKKAVTKAQKKDGKKRKRSRK-amide (SEQ ID NO: 57) | 80µM | 400nM | 0.0 |
| PN361 | NH2-KKDGKKRKRSRKESYSVYVYKVLKQ-amide (SEQ ID NO: 58) | 10 µM | 400nM | 42.0 |
| PN73 | KGSKKAVTKAQKKDGKKRKRSRKESYSVYVYKVLKQ (SEQ ID NO: 59) | 10 µM | 400nM | 99.5 |
| PN64 | BrAc-GWTLNSAGYLLGKINLKALAALAKKILamide (SEQ ID NO: 60) | 10 µM | 400nM | 14.5 |
| PN159 | KLALKLALKALKAALKLAamide (SEQ ID NO: 13) | .08 µM | 80nM | 16.4 |
| PN68 | BrAc-KLALKLALKALKAALKLAamide (SEQ ID NO: 61) | 10 µM | 400nM | 0.0 |
| PN182 | Ac-KETWWETWWTEWSQPKKKRKV-amide (SEQ ID NO: 62) | 1 µM | 400nM | 84.9 |
| PN183 | NH2-KETWWETWWTEWSQPGRKKRRQRRRPPQ-amide (SEQ ID NO: 63) | 20 µM | 400nM | 78.1 |
| PN71 | BrAc-RRRRRRR (SEQ ID NO: 64) | 80 µM | 400nM | 0.0 |

TABLE 4-continued

Efficiency of siRNA delivery mediated by rationally-designed polynucleotide delivery-enhancing polypeptides

| PN # | Sequence | Peptide Conc. | siRNA Conc. | % Uptake (%PI-/FAM+) |
|---|---|---|---|---|
| PN87 | QqQqQqQqQq (SEQ ID NO: 65) | 10µM | 400nM | 0.0 |
| PN249 | NH2-RRRQRRKRGGqQqQqQqQqQ-amide (SEQ ID NO: 66) | 80µM | 400nM | 0.0 |
| PN158 | RVIRWFQNKRCKDKK-amide (SEQ ID NO: 67) | 1µM | 400nM | 94.0 |
| PN86 | Ac-LGLLLRHLRHHSNLLANI-amide (SEQ ID NO: 68) | 80µM | 400nM | 62.2 |
| PN162 | GQMSEIEAKVRTVKLARS-amide (SEQ ID NO: 69) | 80µM | 400nM | 0.0 |
| PN228 | NH2-KLWSAWPSLWSSLWKP-amide (SEQ ID NO: 70) | 80µM | 400nM | 6.8 |
| PN357 | NH2-KKKKKKKKK-amide (SEQ ID NO: 71) | 10µM | 400nM | 0.0 |
| PN358 | NH2-AARLHRFKNKGKDSTEMRRRR-amide (SEQ ID NO: 72) | 40µM | 400nM | 0.0 |
| PN283 | Maleimide-GLGSLLKKAGKKLKQPKSKRKV-amide (SEQ ID NO: 73) | 40µM | 400nM | 36.3 |
| PN284 | Maleimide-Dmt-r-FK-amide | 100µM | 400nM | 0.0 |
| PN285 | Maleimide-Dmt-r-FKQqQqQqQqQq-amide (SEQ ID NO: 74) | 8µM | 800nM | 90.7 |
| PN286 | Maleimide-WRFK-amide (SEQ ID NO: 75) | 80µM | 400nM | 0.0 |
| PN289 | Maleimide-WRFKQqQ + qQqQqQq-amide (SEQ ID NO: 76) | 8µM | 400nM | 91.7 |
| PN267 | Maleimido-YRFK-amide (SEQ ID NO: 77) | 80µM | 400nM | 0.3 |
| PN282 | Maleimide-YRFKYRFKYRFK-amide (SEQ ID NO: 78) | 40µM | 800nM | 22.8 |
| PN286 | Maleimide-WRFK-amide (SEQ ID NO: 75) | 80µM | 400nM | 0.0 |
| PN290 | Maleimide-WRFKKSKRKV-amide (SEQ ID NO: 79) | 80µM | 400nM | 5.3 |
| PN291 | Maleimide-WRFKAAVALLPAVLLALLAP-amide (SEQ ID NO: 80) | 4µM | 800nM | 12.5 |
| PN243 | NH2-DiMeYrFKamide (SEQ ID NO: 81) | 40µM | 400nM | 0.0 |
| PN244 | NH2-YrFKamide (SEQ ID NO: 82) | 80µM | 400nM | 0.0 |
| PN245 | NH2-DiMeYRFKamide (SEQ ID NO: 83) | 80µM | 400nM | 0.0 |
| PN246 | NH2-WrFKamide (SEQ ID NO: 84) | 80µM | 400nM | 0.0 |
| PN247 | NH2-DiMeYrWKamide (SEQ ID NO: 85) | 80µM | 400nM | 0.0 |
| PN248 | NH2-KFrDiMeY-amide (SEQ ID NO: 86) | 80µM | 400nM | 0.0 |

TABLE 4-continued

Efficiency of siRNA delivery mediated by rationally-designed polynucleotide delivery-enhancing polypeptides

| PN # | Sequence | Peptide Conc. | siRNA Conc. | % Uptake (%PI-/FAM+) |
|---|---|---|---|---|
| PN287 | Maleimide-WRFKWRFK-amide (SEQ ID NO: 87) | 10µM | 400nM | 8.8 |
| PN288 | Maleimide-WRFKWRFKWRFK-amide (SEQ ID NO: 88) | 4µM | 400nM | 9.0 |

Example 4 siRNA/Delivery is Enhanced by Polynucleotide Delivery-Enhancing Polypeptides in Murine Cells The present example illustrates induction/enhancement of siRNA uptake by polynucleotide delivery-enhancing polypeptides of the invention in LacZ cells and also in murine primary fibroblasts. The materials and methods used for these experiments are generally the same as described above, except that for the murine experiments 9 L/LacZ cells were replaced with mouse tail fibroblasts. The results of these studies are provided in Tables 5 and 6 below.

TABLE 5

Efficiency of siRNA delivery mediated by rationally-designed polynucleotide delivery-enhancing polypeptides in murine fibroblasts

| Name | Sequence | Status | % Uptake | siRNA |
|---|---|---|---|---|
| PN250 | NH2-RRRQRRKRGGDIMGEWGNEIFGAIAGFLG-amide (SEQ ID NO: 35) | 0.5 µM siRNA/40 µM peptide | 85.9 | Cy5-eGFP |
| PN73 | NH2-KGSKKAVTKAQKKDGKKRKRSRKESYSVYVYKVLKQ-amide (SEQ ID NO: 59) | 0.5 µM siRNA/25 µM peptide | 94.5 | Cy5-eGFP |
| PEG-PN509 | Peg-KGSKKAVTKAQKKDGKKRKRSRKESYSVYVYKVLKQ-amide (SEQ ID NO: 90) | 0.5 µM siRNA/25 µM peptide | 91 | Cy5-eGFP |
| PN404 | NH2-RGSRRAVTRAQRRDGRRRRRSRRESYSVYVYRVLRQ-amide (SEQ ID NO: 91) | 0.5 µM siRNA/25 µM peptide | 50.4 | Cy5-eGFP |
| PN361 | NH2-KKDGKKRKRSRKESYSVYVYKVLKQ-amide (SEQ ID NO: 58) | 0.5 µM siRNA/50 µM peptide | 65 | Cy5-eGFP |
| PN27 | AAVALLPAVLLALLAPRKKRRQRRRPPQC (SEQ ID NO: 38) | 0.5 µM siRNA/5 ∞M peptide | 60.7 | Cy5-eGFP |
| PN58 | NH2-RQIKIWFQNRRMKWKK-amide (SEQ ID NO: 53) | 1 µM siRNA/20 µM peptide | 3.7 | Cy5-eGFP |
| PN158 | NH2-RVIRWFQNKRCKDKK amide (SEQ ID NO: 67) | 0.5 µM siRNA/50 nM peptide | 86.2 | Cy5-eGFP |
| PN316 | Maleimido-RVIRWFQNKRSKDKK-amide (SEQ ID NO: 92) | 0.5 µM siRNA/100 µM peptide | 84.8 | Cy5-eGFP |
| PN289 | Maleimide-WRFKQqQqQqQqQq-amide (SEQ ID NO: 76) | 0.5 µM siRNA/100 µM peptide | 7 | Cy5-eGFP |
| PN28 | NH2-RKKRRQRRRPPQCAAVALLPAVLLALLAP-amide (SEQ ID NO: 39) | 1 µM siRNA/8µM peptide | 80.5 | Cy5-eGFP |
| PN173 | GRKKRRQRRRPPQC (SEQ ID NO: 36) | 0.5 µM siRNA/130 nM peptide | 94.8 | Cy5-eGFP |
| PN159 | KLALKLALKALKAALKLA-amide (SEQ ID NO: 13) | 0.5 µM siRNA/5 µM peptide | 0 | Cy5-eGFP |
| PN161 | NH2-GWTLNSAGYLLGKINLKALAALAKKIL-amide (SEQ ID NO: 93) | 0.5 µM siRNA/10 nM peptide | 0 | Cy5-eGFP |

TABLE 6

Efficiency of siRNA delivery mediated by rationally-designed polynucleotide delivery-enhancing polypeptides in LacZ cells and murine fibroblasts

| Peptide | Sequence | Percent Uptake | |
|---|---|---|---|
| | | LacZ Cells | Primary MTF Cells |
| PN27 | NH2-AAVALLPAVLLALLAPRKKRRQRRRPPQ-amide (SEQ ID NO: 94) | 86 | 61 |
| PN28 | NH2-RKKRRQRRRPPQAAVALLPAVLLALLAP-amide (SEQ ID NO: 89) | 79 | 81 |
| PN29 | NH2-AAVALLPAVLLALLAPSGASGLDKRDYV-amide (SEQ ID NO: 47) | 87 | not tested |
| PN58 | NH2-RQIKIWFQNRRMKWKK-amide (SEQ ID NO: 53) | 76 | 6 |
| PN61 | NH2-SGRGKQGGKARAKAKTRSSRAGLQFPVGRVHRLLRKGC-amide (SEQ ID NO: 56) | 87 | not tested |
| PN73 | NH2-KGSKKAVTKAQKKDGKKRKRSRKESYSVYVYKVLKQ-amide (SEQ ID NO: 59) | 91 | 95 |
| PN158 | NH2-RVIRWFQNKRCKDKK-amide (SEQ ID NO: 67) | 94 | 86 |
| PN173 | NH2-GRKKRRQRRRPPQC-amide (SEQ ID NO: 36) | 85 | 95 |
| PN182 | NH2-KETWWETWWTEWSQPKKKRKV-amide (SEQ ID NO: 95) | 85 | not tested |
| PN202 | NH2-LLETLLKPFQCRICMRNFSTRQARRNHRRRHRR-amide (SEQ ID NO: 50) | 71 | not tested |
| PN204 | NH2-C(YGRKKRRQRRRG)2-amide (SEQ ID NO: 42) | 83 | not tested |
| PN250 | NH2-RRRQRRKRGGDIMGEWGNEIFGAIAGFLG-amide (SEQ ID NO: 35) | 99 | 86 |
| PN361 | NH2-KKDGKKRKRSRKESYSVYVYKVLKQ-amide (SEQ ID NO: 58) | 42 | 65 |
| PN365 | NH2-AAVALLPAVLLALLAPRRRRRR-amide (SEQ ID NO: 45) | 81 | not tested |
| PN404 | NH2-RGSRRAVTRAQRRDGRRRRRSRRESYSVYVYRVLRQ-amide (SEQ ID NO: 91) | not tested | 50 |
| PN453 | NH2-GALFLGFLGAAGSTMGAWSQPKSKRKVC-amide (SEQ ID NO: 96) | not tested | 79 |
| PN509 | Peg-KGSKKAVTKAQKKDGKKRKRSRKESYSVYVYKVLKQ-amide (SEQ ID NO: 90) | not tested | 91 |

Example 5 siRNA/Delivery is Enhanced by Conjugation of the siRNA to Polynucleotide Delivery-Enhancing Polypeptides The present example provides results from screens to evaluate activity of siRNA/polynucleotide delivery-enhancing polypeptide conjugates for inducing or enhancing siRNA uptake in 9 L/LacZ culture cell lines and primary fibroblast from mouse tail. The materials and methods employed for these studies are generally the same as described above, except that no siRNA/peptide mixing is required as needed to produce siRNA/peptide complexes. The results of these studies are provided in Tables 7 and 8 below.

TABLE 7

Efficiency of siRNA delivery mediated by rationally-designed polynucleotide delivery-enhancing polypeptides conjugated to siRNAs in LacZ cells

| Conjugates | Peptide | siRNA | | Uptake % |
|---|---|---|---|---|
| CoP267nfR137-1 | YRFK (SEQ ID NO: 97) | FAM-μ-gal | tested up to 2.0 μM | 0 |
| CoP286nfR138-1 | WRFK (SEQ ID NO: 98) | FAM-μ-gal | 0.8 μM | 0 |
| CoP287nfR138-1 | (WRFK)$_2$ (SEQ ID NO: 99) | FAM-β-gal | 0.8 μM | 0 |
| CoP284nfR164-1 | Dmt-r-FK | FAM-β-gal | tested up to 1.0 μM | 0 |
| CoP282nfR165-1 | (YRFK)$_3$ (SEQ ID NO: 100) | FAM-β-gal | tested up to 1.0 μM | 0 |
| CoP290nfR165-1 | WRFKKSKRKV (SEQ ID NO: 101) | FAM-β-gal | tested up to 1.0 μM | 0 |
| CoP277nfR167-1 | PN73 | FAM-β-gal | 1.0 μM | 42.9 |
| CoP277nfR167-2 | PN73 | FAM-β-gal | 2.0 μM | 55.4 |

TABLE 8

Efficiency of siRNA delivery mediated by rationally-designed polynucleotide delivery-enhancing polypeptides conjugated to siRNAs in murine fibroblasts

| Name | Sequence | siRNA | Status | | % Uptake |
|---|---|---|---|---|---|
| Cy5-dsCoP278nfR270 | Maleimide-RRRQRRKRGGDIMGEWGNEIFGAIAGFLG-amide (SEQ ID NO: 102) | Cy5-eGFP | 0.5 | μM | 96.3 |
| dsCoP277nfR317 | Maleimide-KGSKKAVTKAQKKDGKKRKRSRKESYSVYVYKVLKQ-amide (SEQ ID NO: 103) | Cy5-eGFP | 4 | μM | 83.5 |
| dsCoP275nfR321 | Maleimide-AAVALLPAVLLALLAPRKKRRQRRRPPQ-amide (SEQ ID NO: 37) | Cy5-eGFP | 4 | μM | 52.1 |
| dsCoP285nfR322-1 | Maleimide-Dmt-r-FKQqQqQqQqQqQq-amide (SEQ ID NO: 74) | Cy5-eGFP | 4 | μM | 41.3 |
| dsCoP236nfR332 | Maleimide-RQIKIWFQNRRMKWKK-amide (SEQ ID NO: 52) | Cy5-eGFP | 4 | μM | 36.3 |
| dsCoP317nfR320 | Maleimido-KETWWWETWWTEWSQPKKKRKV-amide (SEQ ID NO: 104) | Cy5-eGFP | 2 | μM | 29.6 |
| dsCoP316nfR347 | Maleimido-RVIRWFQNKRSKDKK-amide (SEQ ID NO: 92) | Cy5-eGFP | 2 | μM | 17.1 |
| dsCoP289nfR268 | Maleimide-WRFKQqQqQqQqQq-amide (SEQ ID NO: 76) | Cy5-eGFP | 4 | μM | 3.2 |
| dsCoP276nfR319 | Maleimide-RKKRRQRRRPPQCAAVALLPAVLLALLAP-amide (SEQ ID NO: 105) | Cy5-eGFP | 2 | μM | 3.6 |
| dsCoP298cfR248 | NH2-WRFKC-amide (SEQ ID NO: 106) | Cy5-eGFP | 4 | μM | 4.1 |
| dsCoP280nfR362-1 | Maleimide-GRKKRRQRRRPPQ-amide (SEQ ID NO: 43) | Cy5-eGFP | 4 | μM | 1.8 |
| dsCoP458nfR363-1 | Maleimido-KLALKLALKALKAALKLA-amide (SEQ ID NO: 107) | Cy5-eGFP | 4 | μM | 10.8 |
| dsCoP459nfR364-1 | Maleimido-GWTLNSAGYLLGKThJLKALAALAKKIL-amide (SEQ ID NO: 108) | Cy5-eGFP | 4 | μM | 54.5 |

The foregoing data evince that a diverse assemblage of siRNA/peptide conjugates of the invention mediate delivery of siRNAs into different cell types at high efficiency.

Example 6 siRNA Gene Expression Knock Down is Enhanced by Polynucleotide Delivery-Enhancing Polypeptides Conjugated to siRNA The instant example demonstrates effective knockdown of target gene expression by siRNA/polynucleotide delivery-enhancing polypeptide complexes of the invention. In the current studies, the ability of peptide/siRNA complex to modulate expression of a human tumor necrosis factor-α (hTNF-α) gene, implicated as mediating the occurrence or progression of RA when overexpressed in human and other mammalian subjects, was tested.

Healthy human blood was purchased from Golden West Biologicals (CA), the peripheral blood mononuclear cells (PBMC) were purified from the blood using Ficoll-Pague plus (Amersham) gradient. Human monocytes were then purified from the PBMCs fraction using magnetic microbeads from Miltenyi Biotech. Isolated human monocytes were resuspended in IMDM supplemented with 4 mM glutamine, 10% FBS, 1× non-essential amino acid and 1× pen-strep, and stored at 4 C until use.

In a 96 well flat bottom plate, human monocytes were seeded at 100K/well/100 μl in OptiMEM medium (Invitrogen). Transfection reagent was mixed with siRNA at desired concentration in OptiMEM medium at room temperature for 20 min (for Lipofectamine 200; Invitrogen), or 5 min (for peptide). At the end of incubation, FBS was added to the mixture (final 3%), and 50 μl of the mixture was added to the cells. The cells were incubated at 37 C for 3 hours. After transfection, cells were transferred to V-bottom plate, and the cells were pelleted at 1500 rpm/5 min. The cells were resuspended in growth medium (IMDM with glutamine, non-essential amino acid, and pen-strep). After overnight incubation, the cells were stimulated with LPS (Sigma) at 1 ng/ml for 3 hours. After induction, cells were collected as above for mRNA quantitation, and supernatant was saved for protein quantitation.

For mRNA measurement, branch DNA technology from Genospectra (CA) was used according to manufacturer's specification. To quantitate mRNA level in the cells, both house keeping gene (cypB) and target gene (TNF-α) mRNA were measured, and the reading for TNF-α was normalized with cypB to obtain relative luminescence unit. To quantify protein level, the TNF-α ELISA from BD Bioscience was used according to manufacturer's specification.

siRNAs for these studies were directed to target different regions of the TNF-α mRNA as illustrated in Table 9 below.

TABLE 9

Nomenclature and target sequence for siRNAs targeting TNF-α

| Name | Alternate Name | position | Target sequence | SEQ ID NO: |
|---|---|---|---|---|
| N125 | TNF-α-1 | 516-534 | GCGTGGAGCTGAGAGATAA | 109 |
| N115 | TNF-α-2 | 430-448 | GCCTGTAGCCCATGTTGTA | 110 |
| N132 | TNF-α-3 | 738-756 | GGTATGAGCCCATCTATCT | 111 |
| N108 | TNF-α-4 | 360-378 | CCAGGGACCTCTCTCTAAT | 112 |
| N138 | TNF-α-5 | 811-829 | GCCCGACTATCTCGACTTT | 113 |
| N113 | TNF-α-6 | 424-442 | TGACAAGCCTGTAGCCCAT | 114 |
| N143 | TNF-α-7 | 844-862 | GGTCTACTTTGGGATCATT | 115 |
| N107 | TNF-α-8 | 359-377 | CCCAGGGACCTCTCTCTAA | 116 |
| N137 | LC1 | 806-828 | AATCGGCCCGACTATCTCGACTT | 117 |
| N122 | LC2 | 514-532 | AAUGGCGUGGAGCUGAGAGAU | 118 |
| N130 | LC3 | 673-691 | AACCUCCUCUCUGCCAUCAAG | 119 |
| N101 | LC4 | 177-195 | AACUGAAAGCAUGAUCCGGGA | 120 |
| N140 | LC5 | 820-838 | AAUCUCGACUUUGCCGAGUCU | 121 |
| N135 | LC6 | 781-799 | AAGGGUGACCGACUCAGCGCU | 122 |
| N128 | LC7 | 636-654 | AAUCAGCCGCAUCGCCGUCUC | 123 |
| N127 | LC8 | 612-630 | AACCCAUGUGCUCCUCACCCA | 124 |
| N118 | LC9 | 472-490 | AAGCUCCAGUGGCUGAACCGC | 125 |
| N111 | LC10 | 398-416 | AAGUCAGAUCAUCUUCUCGAA | 126 |
| N110 | LC11 | 363-381 | AAGGGACCUCUCUCUAAUCAG | 127 |
| N105 | LC12 | 265-287 | CCTCAGCCTCTTCTCCTTCCTGA | 128 |
| N104 | LC13 | 264-282 | AAUCCUCAGCCUCUUCUCCUU | 129 |
| N120 | LC14 | 495-513 | AACCAAUGCCCUCCUGGCCAA | 130 |
| N153 | LC16 | 1535-1555 | CTGATTAAGTTGTCTAAACAA | 131 |
| N136 | LC17 | 787-807 | CCGACTCAGCGCTGAGATCAA | 132 |
| N152 | LC18 | 1327-1347 | CTTGTGATTATTTATTATTTA | 133 |
| N114 | LC19 | 428-448 | AAGCCTGTAGCCCATGTTGTA | 134 |
| N145 | LC20 | 982-1002 | TAGGGTCGGAACCCAAGCTTA | 135 |
| N101 | YC-1 | 177-195 | CUGAAAGCAUGAUCCGGGA | 136 |
| N103 | YC-2 | 251-269 | AGGCGGUGCUUGUUCCUCA | 137 |
| N106 | YC-3 | 300-318 | CCACCACGCUCUUCUGCCU | 138 |
| N109 | YC-4 | 362-380 | AGGGACCUCUCUCUAAUCA | 139 |
| N113 | YC-5 | 424-442 | UGACAAGCCUGUAGCCCAU | 140 |
| N115 | YC-6 | 430-448 | GCCUGUAGCCCAUGUUGUA | 141 |
| N117 | YC-7 | 435-453 | UAGCCCAUGUUGUAGCAAA | 142 |
| N120 | YC-8 | 495-513 | CCAAUGCCCUCCUGGCCAA | 143 |
| N121 | YC-9 | 510-528 | CCAAUGGCGUGGAGCUGAG | 144 |
| N123 | YC-10 | 515-533 | GGCGUGGAGCUGAGAGAUA | 145 |
| N125 | YC-11 | 516-534 | GCGUGGAGCUGAGAGAUAA | 146 |

TABLE 9-continued

Nomenclature and target sequence for siRNAs targeting TNF-α

| Name | Alternate Name | position | Target sequence | SEQ ID NO: |
|---|---|---|---|---|
| N126 | YC-12 | 558-576 | GCCUGUACCUCAUCUACUC | 147 |
| N130 | YC-13 | 673-691 | CCUCCUCUCUGCCAUCAAG | 148 |
| N132 | YC-14 | 738-756 | GGUAUGAGCCCAUCUAUCU | 149 |
| N133 | YC-15 | 772-790 | GCUGGAGAAGGGUGACCGA | 150 |
| N134 | YC-16 | 776-794 | GAGAAGGGUGACCGACUCA | 151 |
| N136 | YC-17 | 787-807 | GCCCGACUAUCUCGACUUU | 152 |
| N141 | YC-18 | 841-859 | GCAGGUCUACUUUGGGAUC | 153 |
| N143 | YC-19 | 844-862 | GGUCUACUUUGGGAUCAUU | 154 |
| N144 | YC-20 | 853-871 | UGGGAUCAUUGCCCUGUGA | 155 |
| N146 | YC-21 | 985-1003 | GGTCGGAACCCAAGCTTAG | 156 |
| N147 | YC-22 | 1179-1197 | CCAGAATGCTGCAGGACTT | 157 |
| N148 | YC-23 | 1198-1216 | GAGAAGACCTCACCTAGAA | 158 |
| N149 | YC-24 | 1200-1218 | GAAGACCTCACCTAGAAAT | 159 |
| N150 | YC-25 | 1250-1268 | CCAGATGTTTCCAGACTTC | 160 |
| N151 | YC-26 | 1312-1330 | CTATTTATGTTTGCACTTG | 161 |
| N154 | YC-27 | 1547-1565 | TCTAAACAATGCTGATTTG | 162 |
| N155 | YC-28 | 1568-1585 | GACCAACTGTCACTCATT | 163 |

The foregoing studies demonstrate that siRNAs targeting TNF-α expression are effectively delivered in an active state by polynucleotide delivery-enhancing polypeptides of the invention to mediate knockdown of TNF-α expression in monocytes.

TABLE 10

TNF-α knockdown mediated by a PN73/siRNA complex

| Target Gene | Complex siRNA | Peptide | KD (%) |
|---|---|---|---|
| TNF-α | 4 nM | 1.6 µM | |
| TNF-α | LC1 | PN73 | 20.08 |
| TNF-α | LC2 | | 19.06 |
| TNF-α | LC3 | | 23.17 |
| TNF-α | LC4 | | 26.67 |
| TNF-α | LC5 | | 46.78 |
| TNF-α | LC6 | | 44.10 |
| TNF-α | LC7 | | 42.76 |
| TNF-α | LC8 | | 41.24 |
| TNF-α | LC9 | | 40.32 |
| TNF-α | LC10 | | 13.52 |
| TNF-α | LC11 | | 7.89 |
| TNF-α | LC12 | | 40.61 |
| TNF-α | LC13 | | 48.29 |
| TNF-α | LC14 | | 50.76 |
| TNF-α | LC16 | | 55.91 |
| TNF-α | LC17 | | 50.78 |
| TNF-α | LC18 | | 63.44 |
| TNF-α | LC19 | | 61.83 |
| TNF-α | LC20 | | 42.68 |
| TNF-α | YC12 | | 43.60 |

TABLE 11

TNF-α knockdown mediated by a PN509/siRNA complex

| Target Gene | Complex siRNA | Peptide | KD (%) |
|---|---|---|---|
| TNF-α | 4 nM | 1.6 µM | |
| TNF-α | LC1 | PN509 | 31.13 |
| TNF-α | LC2 | | 37.04 |
| TNF-α | LC3 | | 30.14 |
| TNF-α | LC4 | | 22.71 |
| TNF-α | LC5 | | 34.93 |
| TNF-α | LC6 | | 50.19 |
| TNF-α | LC7 | | 56.11 |
| TNF-α | LC8 | | 47.35 |
| TNF-α | LC9 | | 58.20 |
| TNF-α | LC10 | | 25.62 |
| TNF-α | LC11 | | 25.65 |
| TNF-α | LC12 | | 17.03 |
| TNF-α | LC13 | | 25.04 |
| TNF-α | LC14 | | 42.78 |
| TNF-α | LC16 | | 40.06 |
| TNF-α | LC17 | | 48.94 |
| TNF-α | LC18 | | 58.13 |
| TNF-α | LC19 | | 56.38 |
| TNF-α | LC20 | | 71.12 |
| TNF-α | YC12 | | 64.37 |

TABLE 12

TNF-α knockdown mediated by a PN250/siRNA complex

| Target Gene | Complex siRNA | Peptide | KD (%) |
|---|---|---|---|
| TNF-α | 20 nM | PN250 | |
| TNF-α | YC11 | 0.5 µM | 13.70 |
| TNF-α | YC12 | | 17.06 |
| TNF-α | YC17 | | 17.30 |
| TNF-α | YC18 | | 20.72 |
| TNF-α | LC13 | | 20.65 |
| TNF-α | LC20 | | -3.80 |
| TNF-α | TNF-4 | | 0.90 |
| TNF-α | YC11 | 0.75 µM | 21.09 |
| TNF-α | YC12 | | 21.66 |
| TNF-α | YC17 | | 29.82 |
| TNF-α | YC18 | | 17.82 |
| TNF-α | LC13 | | 18.04 |
| TNF-α | LC20 | | 10.72 |
| TNF-α | TNF-4 | | 14.39 |
| TNF-α | YC11 | 1 µM | 33.10 |

TABLE 12-continued

TNF-α knockdown mediated by a PN250/siRNA complex

| Target Gene | Complex siRNA | Peptide | KD (%) |
|---|---|---|---|
| TNF-α | YC12 | | 15.91 |
| TNF-α | YC17 | | 24.68 |
| TNF-α | YC18 | | 24.66 |
| TNF-α | LC13 | | 31.35 |
| TNF-α | LC20 | | 26.53 |
| TNF-α | TNF-4 | | 26.47 |

The foregoing data evince that effective levels of TNF-α gene expression knock down can be achieved in mammalian cells using the novel siNA/polynucleotide delivery-enhancing polypeptide compositions of the invention.

Screening and Characterization

FIG. 1 characterizes an exemplary assay system for screening siRNA candidate sequences for TNF-α knockdown activity. Human monocytes (CD 14+) treated with LPS induce TNF-α-specific mRNA within approximately 2 hrs, followed by peak levels of TNF-α protein 2 hrs later. siRNAs were screened for knockdown activity by transfecting monocytes with siRNA candidate sequences using Lipofectamine 2000, treating infected cells with LPS, and measuring TNF-α mRNA levels approximately 16 hrs later. Fifty six siRNA sequences were designed and screened for their ability to knockdown TNF-α mRNA and protein levels in activated human primary monocytes. Activities for a representative set of 27 siRNA sequences ranged from 80% mRNA knockdown to no detectable activity. In general, TNF-α protein levels were reduced more than mRNA levels, e.g., a 50% knockdown in TNF-α mRNA (TNF-α-1) resulted in a 75% reduction in TNF-α protein level. Dose response curves for selected siRNAs that exhibited knockdown levels from 30 to 60% were obtained. Calculated $IC_{50}$ values were in the 10-200 pMolar range. While the siRNA sequences evaluated were distributed throughout the TNF-α transcript, the most potent siRNAs identified were located in two areas: the middle of the coding region and the 3'-UTR.

Example 7 siRNA Gene Expression Knock Down is Enhanced by Polynucleotide Delivery-Enhancing Polypeptides Complexed with siRNA The present example demonstrates knockdown of target gene expression by peptide-siRNA conjugates of the invention. The materials and methods for these studies are the same as those described above, with the exception that no mixing of the siRNA and peptide is required. In the present series of studies, the knockdown experiments included comparison of siRNA/peptide-mediated knockdown with and without lipofectamine.

TABLE 13 siRNA/peptide-mediated knockdown of TNF-α expression with and without lipofectamine

| | Peptide | siRNA | Cells in Assay | with Lipofectamine conc. (uM) | KD (%) | without Lipofectamine conc. (uM) | KD (%) |
|---|---|---|---|---|---|---|---|
| CoP456 | cIBR | LC20 | CD14 | 0.4 | no KD | 0.4 | no KD |
| | | | | 1.3 | no KD | 1.3 | no KD |
| | | | | 4 | no KD | 4 | no KD |
| CoP457 | Peptide T | LC20 | | 0.4 | no KD | 0.4 | no KD |
| | | | | 1.3 | no KD | 1.3 | no KD |
| | | | | 4 | no KD | 4 | no KD |
| CoP278 | TAT + HA | YC12 | | 0.4 | no KD | 0.4 | no KD |
| | | | | 1.3 | no KD | 1.3 | no KD |
| | | | | 4 | no KD | 4 | no KD |
| CoP277 | PN73 | LC13 | MTF | 0.19 | 31.95 | 0.19 | 61.61 |
| | | | | 0.38 | 32.83 | 0.38 | 76.31 |
| | | | | 0.75 | 39.29 | 0.75 | 73.94 |
| | | | | 1.50 | 41.42 | 1.50 | 73.14 |
| | | | | 3.00 | 39.88 | 3.00 | 58.14 |
| | | | | 6.00 | 20.23 | 6.00 | 50.71 |
| CoP277 | PN73 | LC13 | CD14 | | | 0.000 | 93.06 |
| | | | | | | 0.002 | 83.63 |
| | | | | | | 0.011 | 72.58 |
| | | | | | | 0.053 | 73.52 |
| | | | | | | 0.266 | 85.01 |
| CoP277 | PN73 | LC20 | CD14 | | | 0.000 | 75.15 |
| | | | | | | 0.002 | 60.72 |
| | | | | | | 0.011 | 57.09 |
| | | | | | | 0.053 | 58.70 |
| | | | | | | 0.266 | 62.79 |

The foregoing data evince that a diverse assemblage of polynucleotide delivery-enhancing polypeptides of the invention complexed with siRNAs function to enhance siRNA-mediated knockdown of TNF-gene expression in mammalian subjects.

Example 8

Time Course of siRNA Gene Expression Knock Down

The instant example presents studies relating to the time course of siRNA-mediated gene expression knockdown. To test the duration of the siRNA effect, the siRNA transfection procedures as noted above were employed, except that fibroblasts derived from eGFP expressing mice were used. The transfection reagent used here was lipofectamine. The cells were replated on the 18$^{th}$ day due to overgrowth. The second transfection was performed on the 19$^{th}$ day post first transfection. On the 19$^{th}$ day the eGFP levels were measured after the transfection. Scramble or nonsense siRNA (Qiagen) was used as a control, along with a GFPI siRNA (GFPI) and a hairpin siRNA (D#21). The knockdown activities were calibrated with scramble siRNA (Qiagen control).

TABLE 14

Time Course of siRNA Gene Expression Knock Down

| | Days post first transfection | | | | | | | | | | | | | |
|---|---|---|---|---|---|---|---|---|---|---|---|---|---|---|
| | 1 | 3 | 5 | 7 | 9 | 11 | 13 | 15 | 17 | 19 | 20 | 21 | 25 | 27 |
| Qiagen | 0.00 | 0.00 | 0.00 | 0.00 | 0.00 | 0.00 | 0.00 | 0.00 | 0.00 | 0.00 | 0.00 | 0.00 | 0.00 | 0.00 |
| GFPI | 27.61 | 60.87 | 64.75 | 58.40 | 56.72 | 40.46 | 35.56 | 16.59 | 15.50 | 59.60 | 37.10 | 57.38 | 66.94 | 59.63 |
| D#21 | 28.22 | 61.11 | 66.91 | 62.86 | 57.36 | 54.71 | 42.96 | 24.66 | 9.88 | 46.36 | 35.89 | 65.25 | 74.15 | 58.39 |

The foregoing studies demonstrate that siRNA knockdown activity became apparent around day 3, and was sustained through day 9, whereafter target gene expression returned to baseline levels around day 17. After the second transfection on day 18, another reduction of eGFP expression occurred indicating that the reagent can be repeatedly administered to cells to yield repeated or enduring gene expression knockdown.

Example 9

Dosage Dependence of TNF Gene Expression Knock Down Mediated by siRNA Complexed with Polynucleotide Delivery-Enhancing Polypeptide The present example demonstrates that knockdown activity mediated by siRNA complexed with an exemplary polynucleotide delivery-enhancing polypeptide, PN73, in activated human monocytes is dosage dependent.

The siRNA/PN73 complex was provided in a constant ratio between PN73 and siRNA of about PN73:siRNA=82:1. 400 nM siRNA was complexed with 33 µM PN73 for 5 min in OptiMEM medium. After complexation, the complex were serial diluted (1:2 ratio) with OptiMEM. The complex was added to human monocytes for transfection. The following induction and mRNA quantification was performed according to the description above.

TABLE 15

Peptide Dosage Dependence of TNF Gene Expression Knock Down PN73:siRNA ratio = 82:1

| PN73 (µM) | siRNA (nM) | Control | TNF-2 | TNF-4 | LC8 |
|---|---|---|---|---|---|
| | 0 | 100 | 100 | 100 | 100 |
| 1.2 | 14.81 | 99.99 | 80.28 | 70.22 | 73.44 |
| 3.6 | 44.44 | 100.11 | 69.33 | 62.97 | 63.04 |
| 11 | 133.33 | 99.99 | 57.82 | 62.71 | 59.57 |
| 33 | 400.00 | 99.99 | 64.51 | 78.48 | 51.30 |

In a related series of experiments, siRNA was serially diluted and combined with a fixed amount of PN73 (1.67 µM). Alternatively stated, the PN73 polynucleotide delivery-enhancing polypeptide was complexed with titration amounts of siRNA. PN73 (1.67 µM) was complexed with each titration amount of siRNA for 5 min at RT in OptiMEM medium. After complexation, the complex was added to human monocytes for transfection. The induction and mRNA quantification data provided in Table 16, below, were obtained by methods described above.

TABLE 16 siRNA Dosage Dependence of TNF-α Gene Expression Knock Down 1.67 µM PN73 complexed with titration amount of siRNA

| siRNA conc. (nM) | Control | LC20 |
|---|---|---|
| 0.8 | 100.0 | 84.7 |
| 4 | 100.0 | 59.4 |
| 20 | 100.0 | 65.2 |
| 100 | 100.0 | 54.7 |

Example 10

Multiple Dosing Protocol to Extend siRNA Knockdown Effect in Mammalian Cells

The instant example demonstrates that multiple dosing schedules will effectively extend gene expression knockdown effects in mammalian cells mediated by siNA/polynucleotide delivery-enhancing polypeptide compositions of the invention. The materials and methods employed for these studies are the same as described above, with the exception that repeated transfections were conducted at the times indicated. The scramble siRNA (Qiagen) was utilized for side by side controls.

TABLE 17

Repeated siRNA TNF-α Gene Expression Knock Down

| | Days post 1st transfection | | | | | | | | |
|---|---|---|---|---|---|---|---|---|---|
| | 4 | 5 | 6 | 7 | 8 | 9 | 10 | 11 | 12 |
| Single | 74.69 | 61.87 | 62.57 | 55.47 | 41.41 | 39.42 | 27.21 | | |
| 2nd on 5th | | | 66.69 | 69.78 | 68.27 | 64.18 | 63.86 | 64.37 | 56.52 |
| $2^{nd}$ on 6th | | | | 64.21 | 65.78 | 67.74 | 64.12 | 58.64 | 53.96 |
| $2^{nd}$ on 7th | | | | | 63.03 | 62.50 | 69.94 | 62.63 | 58.07 |

The foregoing studies demonstrate that when multiple transfections are performed timely (in this case between about the $5^{th}$-$7^{th}$ day post first transfection), gene expression knockdown effects in mammalian cells can be prolonged or re-induced.

Example 11

In Vivo siRNA/Peptide-Mediated TNF-α Gene Expression Knock Down

The present example provides In Vivo studies demonstrating the efficacy of siRNA/polynucleotide delivery-enhancing polypeptide compositions of the invention to mediate systemic delivery and therapeutic gene knockdown by siRNA, effective to modulate target gene expression and modify phenotype of cells in a therapeutic manner.

Human NF-α expressing mice were purchase from the Hellenic Pasture Institute, Greece) at 5 weeks old. Mice were administered through i.v. with 300 μl saline twice a week (4 mice), with the RA drug Ramicade (5 mg/kg) once a week (2 mice), or with N145 siRNA (2 mg/kg) mixed with PN73 at 1:5 molar ratio twice a week (2 mice). During the injection periods, plasma samples were collected for ELISA testing (R&D Systems, Cat#SSTA00C), and paw scores were taken twice a week as an accepted index of RA disease progression and therapeutic efficacy.

TABLE 18 hTNF-α ELISA

| Age(week) | 7 | 8 | 9 |
|---|---|---|---|
| Ramicade | 102.24 | 39.27 | 25.80 |
| N145/PN73 | 25.96 | 21.89 | 14.21 |
| Saline | 33.78 | 34.29 | 24.48 |

*These data represent the average of the mice in the experiment in pg/ml.

The foregoing data demonstrate effective reduction of hTNF-α levels in siRNA/peptide-treated mice in the circulating blood as compared to levels in Ramicade or saline (control) treated mice.

Additional evidence of in vivo efficacy of the siNA/polynucleotide delivery-enhancing polypeptide compositions and methods of the invention were obtained from the above murine subjects using paw scores, an accepted phenotypic index for RA disease status and treatment efficacy. Due to the difference in the starting point (some animals present with scores at earlier points), the scores have been adjusted to 0 for all animals in the experiments. Each paw is given a score between 0 and 3, with the highest score of 12, according to the following scoring index.
  0: Normal
  1: edema or distortion of paw or ankle joints
  2: distortion of paw and ankle joints
  3: ankylosis of wrist or ankle joints.

Figure 3:
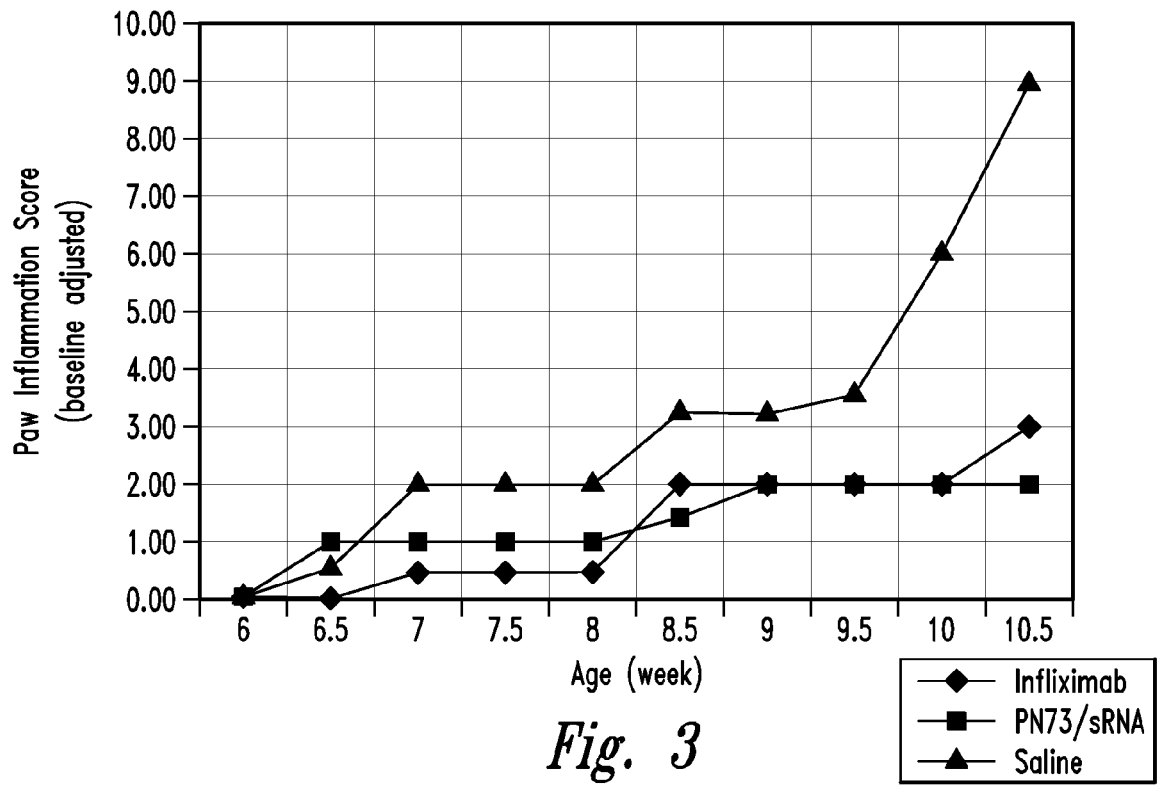
FIG. 3 shows paw data for siRNA/peptide injected mice which demonstrate delayed RA progression in the treated mice comparable to that exhibited by Ramicade-treated subjects.

The results of these paw score evaluations are presented graphically in FIG. 3. The data demonstrate that the siRNA/peptide injected animals showed a delayed RA progression which was comparable to that exhibited by the Ramicade-treated mice. The results from the foregoing studies demonstrate that small interfering nucleic acid and polynucleotide delivery-enhancing polypeptide compositions of the invention provide promising new therapeutic tools for regulating gene expression and treating and managing disease. siNAs of the invention, for example siNAs targeting human hTNF-α-specific mRNAs for degradation, offer higher specificity, lower immunogenicity and greater disease modification than current small molecule, soluble receptor, or antibody therapies for RA. More than 50 candidate siRNA sequences were screened that targeted hTNF-α and yielded single administration knockdowns of 30-85%. Over 20 in silico designed peptide complex and/or covalent molecules were compared for fluorescent RNA uptake by monocytes and a number were found to have significantly better uptake than Lipofectamine or cholesterol-conjugated siRNA and with <10 μM $IC_{50}$ values. The peptide-siRNA formulations efficiently knockdown TNF-α mRNA and protein levels in activated human monocytes in vitro.

One exemplary candidate siRNA/delivery peptide formulation was evaluated in two transgenic mouse models of rheumatoid arthritis (RA) constitutively expressing human TNF-α. Animals treated with 2 mg/kg siRNA by IV injection or infliximab twice weekly beginning at age 6 weeks showed RA score stabilization (paw and joint inflammation) beginning at age 7 weeks, compared to controls where these disease conditions persisted through week 10. At age 9 weeks, siRNA treated animals showed comparable reductions in RA scores, but significantly lower plasma TNF-α protein levels than infliximab treated animals.

Based on the disclosure herein, the use of siRNA to inhibit the expression of target genes, for example cytokines such as TNF-α, that play important roles in pathological states, such as inflammation, provides effective treatments to alleviate or prevent symptoms of disease, as exemplified by RA, in mammalian subjects. Exemplary siRNA/peptide compositions employed within the methods and compositions of the invention provide advantages relating to their ability to reduce or eliminate target gene expression, e.g., TNF-α expression, rather than by complexing with the product of the target gene, e.g., TNF-α, as in the case of antibodies or soluble receptors.

Improving systemic delivery of nucleic acids according to the teachings of the invention provides yet additional advantages for development of siNAs as drugs. Specific challenges in this context include delivery through tissue barriers to a target cell or tissue, maintaining the stability of the siNA, and intracellular delivery—getting siNAs across cell membranes into cells in sufficient quantities to be effective. The present disclosure demonstrates for the first time an effective in vivo delivery system comprising novel peptide-siRNA compositions targeting specific gene expression, such as expression of human TNF-α, which attenuate disease activity in transgenic animal models predictive of target diseases, as exemplified by studies using murine models of RA. In related studies, the compositions and methods of the invention effectively inhibit TNF-α expression in activated monocytes derived from patients with RA. These results indicate that the RNAi pathway effectively mediates alteration of cellular phenotype and disease progression through intracellular effects on TNF-pathways, and avoids toxicity effects due to circulating antibody/TNF-α complexes with residual immunoreactivity that characterize current antibody therapies for RA. Notably, all of the tests herein were implemented with associated toxicity effects minimized, such that the dosages of siNAs and polynucleotide delivery-enhancing polypeptides shown in these examples always correlated with cell viability levels of at least 80-90% or greater.

Example 12

Optimizing Rational Design of Polynucleotide Delivery-Enhancing Polypeptides

The instant example provides exemplary study design and data for optimizing rational design of polynucleotide delivery-enhancing polypeptides of the invention. The subject rational design manipulations were conducted for a histone H2B-derived polynucleotide delivery-enhancing polypeptide.

TABLE 19

Deletion and modification of PN73

| PN73 | |
| PN360 | |
| PN361 | |
| PN404 | |
| PN509 | |

The above Table 19 provides a diagram of the primary structure of PN73 and its derivatives generated for optimizing rational design of PN73-based polynucleotide delivery-enhancing polypeptides. The parent peptide PN73 was demonstrated above to be an excellent example of polynucleotide delivery-enhancing polypeptides for inducing or enhancing siRNA delivery to cells. In order to better understand the function-structural activity relationships of this and other polynucleotide delivery-enhancing polypeptides, primary structural studies were performed by characterizing C- and N-terminal function, and activity of conjugates between PN73 and other chemical moieties.

As noted above, PN73 is a peptide from histone 2B, residues 12-48 aa. PN360 is C-terminal deleted version of PN73 (12-35) and PN361 id N-terminal deleted version of PN73 (23-48). PN404 is a version of PN73 in which all of lysines are replaced with arginines as shown below:

(SEQ ID NO: 91)
NH2-RGSRRAVTRAQRRDGRRRRRSRRESYSVYVYRVLRQ-amide

PN509 is a pegylated PN73 (PEG molecular weight 1 k Dalton) derivative that is pegylated at the N-terminus.

Figure 4:
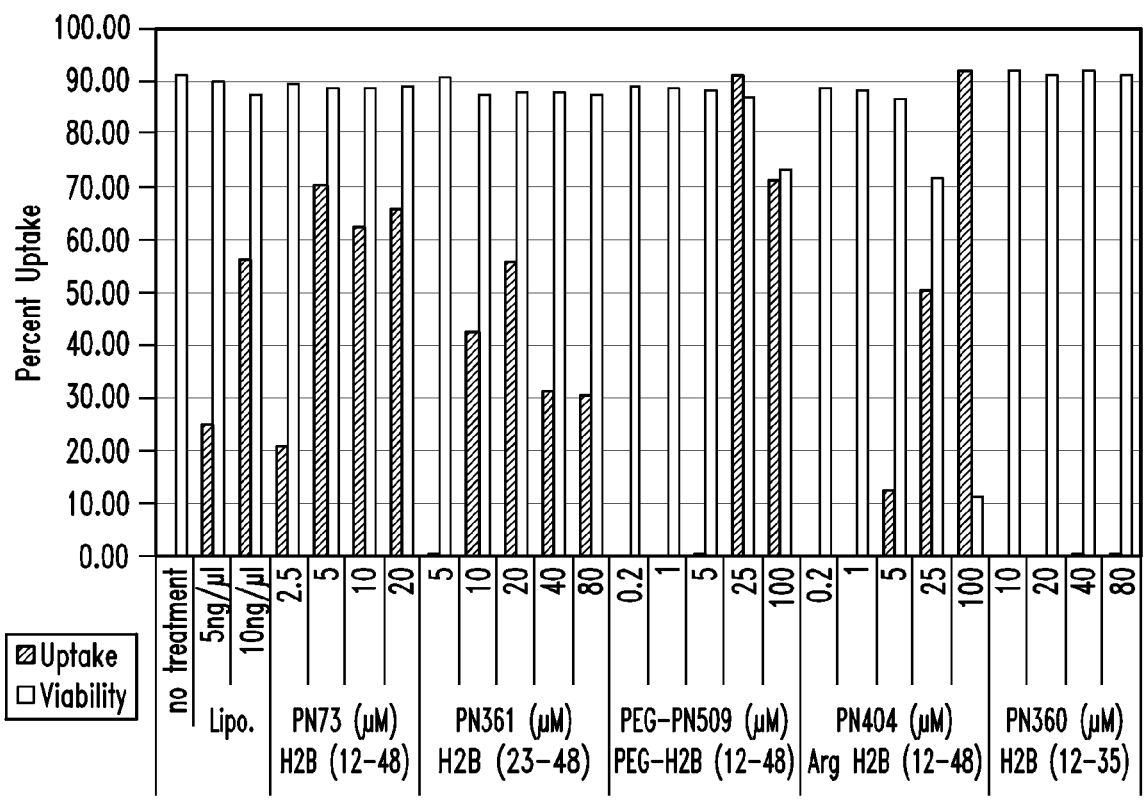
FIG. 4 provides results of uptake efficacy and viability studies in mouse fibroblasts for PN73 rationally-designed derivative polynucleotide delivery-enhancing polypeptides of the invention.

FIG. 4 provides the results of uptake efficacy and viability studies in mouse fibroblasts for the foregoing PN73 rationally-designed derivative polynucleotide delivery-enhancing polypeptides. The activity changes of modified PN73 in mouse tail fibroblast cells are illustrated. Unlike PN404, PN509 increases uptake without increasing toxicity. While deleting part of the N-terminus of PN73 reduces activity, removal of C-terminal residues abolishes the activity. Both PN73 and PN509 show higher activity in primary cells than Lipofectamine (Invitrogen, CA). The uptake measurements were performed using mouse tail fibroblast cells.

Although the foregoing invention has been described in detail by way of example for purposes of clarity of understanding, it will be apparent to the artisan that certain changes and modifications may be practiced within the scope of the appended claims which are presented by way of illustration not limitation. In this context, various publications and other references have been cited within the foregoing disclosure for economy of description. Each of these references is incorporated herein by reference in its entirety for all purposes. It is noted, however, that the various publications discussed herein are incorporated solely for their disclosure prior to the filing date of the present application, and the inventors reserve the right to antedate such disclosure by virtue of prior invention.

What is claimed is:

1. A composition comprising a double-stranded ribonucleic acid (dsRNA) active for RNA interference and a polynucleotide delivery-enhancing polypeptide comprising SEQ ID NO:63.

2. The composition of claim 1, wherein the dsRNA has a double-stranded region from about 10 to about 49 base pairs.

3. The composition of claim 1, wherein the dsRNA has a double-stranded region from about 15 to about 35 base pairs.

4. The composition of claim 1, wherein the dsRNA has at least one 3'-overhang.

5. The composition of claim 1, wherein the dsRNA has at least one blunt end.

6. The composition of claim 1, wherein the N-terminus of the polynucleotide delivery-enhancing polypeptide is acetylated.

7. The composition of claim 1, wherein the N-terminus of the polynucleotide delivery-enhancing polypeptide has a maleimido moiety.

8. The composition of claim 1, wherein the N-terminus of the polynucleotide delivery-enhancing polypeptide is pegylated.

9. A method of delivering a dsRNA to a cell, comprising contacting the cell with the composition of claim 1.

10. A method of reducing the expression of a target gene, comprising administering the composition of claim 1 to a cell expressing the target gene, wherein the dsRNA of the composition reduces expression of the target gene in the cell.

11. The composition of claim 1, wherein the polynucleotide delivery-enhancing polypeptide and the dsRNA are admixed.

12. The composition of claim 1, wherein the polynucleotide delivery-enhancing polypeptide and the dsRNA are complexed.

13. The composition of claim 1, wherein the polynucleotide delivery-enhancing polypeptide and the dsRNA are conjugated.

* * * * *

SEQUENCE LISTING

<160> NUMBER OF SEQ ID NOS: 163

<210> SEQ ID NO 1
<211> LENGTH: 7
<212> TYPE: PRT
<213> ORGANISM: Human immunodeficiency virus type 1

<400> SEQUENCE: 1

Lys Arg Arg Gln Arg Arg Arg
 1               5

<210> SEQ ID NO 2
<211> LENGTH: 16
<212> TYPE: PRT
<213> ORGANISM: Artificial Sequence

```
<220> FEATURE:
<223> OTHER INFORMATION: Description of Artificial Sequence: Synthetic
      penetratin PTD peptide

<400> SEQUENCE: 2

Arg Gln Ile Lys Ile Trp Phe Gln Asn Arg Arg Met Lys Trp Lys Lys
1               5                   10                  15

<210> SEQ ID NO 3
<211> LENGTH: 34
<212> TYPE: PRT
<213> ORGANISM: Human herpesvirus 1

<400> SEQUENCE: 3

Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Asp

<210> SEQ ID NO 4
<211> LENGTH: 16
<212> TYPE: PRT
<213> ORGANISM: Homo sapiens

<400> SEQUENCE: 4

Ala Ala Val Ala Leu Leu Pro Ala Val Leu Leu Ala Leu Leu Ala Pro
1               5                   10                  15

<210> SEQ ID NO 5
<211> LENGTH: 16
<212> TYPE: PRT
<213> ORGANISM: Homo sapiens

<400> SEQUENCE: 5

Ala Ala Val Leu Leu Pro Val Leu Leu Pro Val Leu Leu Ala Ala Pro
1               5                   10                  15

<210> SEQ ID NO 6
<211> LENGTH: 15
<212> TYPE: PRT
<213> ORGANISM: Homo sapiens

<400> SEQUENCE: 6

Val Thr Val Leu Ala Leu Gly Ala Leu Ala Gly Val Gly Val Gly
1               5                   10                  15

<210> SEQ ID NO 7
<211> LENGTH: 17
<212> TYPE: PRT
<213> ORGANISM: Human immunodeficiency virus type 1

<400> SEQUENCE: 7

Gly Ala Leu Phe Leu Gly Trp Leu Gly Ala Ala Gly Ser Thr Met Gly
1               5                   10                  15

Ala

<210> SEQ ID NO 8
<211> LENGTH: 17
<212> TYPE: PRT
<213> ORGANISM: Caiman crocodilus

<400> SEQUENCE: 8

Met Gly Leu Gly Leu His Leu Leu Val Leu Ala Ala Ala Leu Gln Gly
```

Ala

<210> SEQ ID NO 9
<211> LENGTH: 24
<212> TYPE: PRT
<213> ORGANISM: Artificial Sequence
<220> FEATURE:
<223> OTHER INFORMATION: Description of Artificial Sequence: Synthetic
      hCT-derived peptide

<400> SEQUENCE: 9

```
Leu Gly Thr Tyr Thr Gln Asp Phe Asn Lys Phe His Thr Phe Pro Gln
 1               5                  10                  15
Thr Ala Ile Gly Val Gly Ala Pro
            20
```

<210> SEQ ID NO 10
<211> LENGTH: 26
<212> TYPE: PRT
<213> ORGANISM: Artificial Sequence
<220> FEATURE:
<223> OTHER INFORMATION: Description of Artificial Sequence: Synthetic
      chimeric peptide

<400> SEQUENCE: 10

```
Gly Trp Thr Leu Asn Ser Ala Gly Tyr Leu Leu Lys Ile Asn Leu Lys
 1               5                  10                  15
Ala Leu Ala Ala Leu Ala Lys Lys Ile Leu
            20                  25
```

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

```
Thr Pro Pro Lys Lys Lys Arg Lys Val Glu Asp Pro Lys Lys Lys Lys
 1               5                  10                  15
```

<210> SEQ ID NO 12
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

```
Arg Arg Arg Arg Arg Arg Arg
 1               5
```

<210> SEQ ID NO 13
<211> LENGTH: 18
<212> TYPE: PRT
<213> ORGANISM: Artificial Sequence
<220> FEATURE:
<223> OTHER INFORMATION: Description of Artificial Sequence: Synthetic
      amphiphilic model peptide

<400> SEQUENCE: 13

```
Lys Leu Ala Leu Lys Leu Ala Leu Lys Ala Leu Lys Ala Ala Leu Lys
 1               5                  10                  15
```

Leu Ala

<210> SEQ ID NO 14
<211> LENGTH: 16
<212> TYPE: PRT
<213> ORGANISM: Influenza A virus

<400> SEQUENCE: 14

Gly Leu Phe Gly Ala Ile Ala Gly Phe Ile Glu Asn Gly Trp Glu Gly
 1               5                  10                  15

<210> SEQ ID NO 15
<211> LENGTH: 16
<212> TYPE: PRT
<213> ORGANISM: Human parainfluenza virus 1

<400> SEQUENCE: 15

Phe Phe Gly Ala Val Ile Gly Thr Ile Ala Leu Gly Val Ala Thr Ala
 1               5                  10                  15

<210> SEQ ID NO 16
<211> LENGTH: 16
<212> TYPE: PRT
<213> ORGANISM: Respiratory syncytial virus

<400> SEQUENCE: 16

Phe Leu Gly Phe Leu Leu Gly Val Gly Ser Ala Ile Ala Ser Gly Val
 1               5                  10                  15

<210> SEQ ID NO 17
<211> LENGTH: 16
<212> TYPE: PRT
<213> ORGANISM: Human immunodeficiency virus type 1

<400> SEQUENCE: 17

Gly Val Phe Val Leu Gly Phe Leu Gly Phe Leu Ala Thr Ala Gly Ser
 1               5                  10                  15

<210> SEQ ID NO 18
<211> LENGTH: 16
<212> TYPE: PRT
<213> ORGANISM: Ebola virus

<400> SEQUENCE: 18

Gly Ala Ala Ile Gly Leu Ala Trp Ile Pro Tyr Phe Gly Pro Ala Ala
 1               5                  10                  15

<210> SEQ ID NO 19
<211> LENGTH: 56
<212> TYPE: PRT
<213> ORGANISM: Homo sapiens

<400> SEQUENCE: 19

Ala Cys Thr Cys Pro Tyr Cys Lys Asp Ser Glu Gly Arg Gly Ser Gly
 1               5                  10                  15

Asp Pro Gly Lys Lys Lys Gln His Ile Cys His Ile Gln Gly Cys Gly
                20                  25                  30

Lys Val Tyr Gly Lys Thr Ser His Leu Arg Ala His Leu Arg Trp His
            35                  40                  45

Thr Gly Glu Arg Pro Phe Met Cys
        50                  55

<210> SEQ ID NO 20
<211> LENGTH: 54

```
<212> TYPE: PRT
<213> ORGANISM: Homo sapiens

<400> SEQUENCE: 20

Ala Cys Thr Cys Pro Asn Cys Lys Asp Gly Glu Lys Arg Ser Gly Glu
 1               5                  10                  15

Gln Gly Lys Lys His Val Cys His Ile Pro Asp Cys Gly Lys Thr
            20                  25                  30

Phe Arg Lys Thr Ser Leu Leu Arg Ala His Val Arg Leu His Thr Gly
         35                  40                  45

Glu Arg Pro Phe Val Cys
     50

<210> SEQ ID NO 21
<211> LENGTH: 55
<212> TYPE: PRT
<213> ORGANISM: Homo sapiens

<400> SEQUENCE: 21

Ala Cys Thr Cys Pro Asn Cys Lys Glu Gly Gly Gly Arg Gly Thr Asn
 1               5                  10                  15

Leu Gly Lys Lys Lys Gln His Ile Cys His Ile Pro Gly Cys Gly Lys
            20                  25                  30

Val Tyr Gly Lys Thr Ser His Leu Arg Ala His Leu Arg Trp His Ser
         35                  40                  45

Gly Glu Arg Pro Phe Val Cys
     50                  55

<210> SEQ ID NO 22
<211> LENGTH: 56
<212> TYPE: PRT
<213> ORGANISM: Homo sapiens

<400> SEQUENCE: 22

Ala Cys Ser Cys Pro Asn Cys Arg Glu Gly Glu Gly Arg Gly Ser Asn
 1               5                  10                  15

Glu Pro Gly Lys Lys Gln His Ile Cys His Ile Glu Gly Cys Gly
            20                  25                  30

Lys Val Tyr Gly Lys Thr Ser His Leu Arg Ala His Leu Arg Trp His
         35                  40                  45

Thr Gly Glu Arg Pro Phe Ile Cys
     50                  55

<210> SEQ ID NO 23
<211> LENGTH: 60
<212> TYPE: PRT
<213> ORGANISM: Drosophila sp.

<400> SEQUENCE: 23

Arg Cys Thr Cys Pro Asn Cys Thr Asn Glu Met Ser Gly Leu Pro Pro
 1               5                  10                  15

Ile Val Gly Pro Asp Glu Arg Gly Arg Lys Gln His Ile Cys His Ile
            20                  25                  30

Pro Gly Cys Glu Arg Leu Tyr Gly Lys Ala Ser His Leu Lys Thr His
         35                  40                  45

Leu Arg Trp His Thr Gly Glu Arg Pro Phe Leu Cys
     50                  55                  60

<210> SEQ ID NO 24
<211> LENGTH: 58
```

<212> TYPE: PRT
<213> ORGANISM: Drosophila sp.

<400> SEQUENCE: 24

Thr Cys Asp Cys Pro Asn Cys Gln Glu Ala Glu Arg Leu Gly Pro Ala
 1               5                  10                  15

Gly Val His Leu Arg Lys Lys Asn Ile His Ser Cys His Ile Pro Gly
                20                  25                  30

Cys Gly Lys Val Tyr Gly Lys Thr Ser His Leu Lys Ala His Leu Arg
            35                  40                  45

Trp His Thr Gly Glu Arg Pro Phe Val Cys
        50                  55

<210> SEQ ID NO 25
<211> LENGTH: 53
<212> TYPE: PRT
<213> ORGANISM: Caenorhabditis elegans

<400> SEQUENCE: 25

Arg Cys Thr Cys Pro Asn Cys Lys Ala Ile Lys His Gly Asp Arg Gly
 1               5                  10                  15

Ser Gln His Thr His Leu Cys Ser Val Pro Gly Cys Gly Lys Thr Tyr
                20                  25                  30

Lys Lys Thr Ser His Leu Arg Ala His Leu Arg Lys His Thr Gly Asp
            35                  40                  45

Arg Pro Phe Val Cys
        50

<210> SEQ ID NO 26
<211> LENGTH: 56
<212> TYPE: PRT
<213> ORGANISM: Caenorhabditis elegans

<400> SEQUENCE: 26

Pro Gln Ile Ser Leu Lys Lys Ile Phe Phe Ile Phe Ser Asn
 1               5                  10                  15

Phe Arg Gly Asp Gly Lys Ser Arg Ile His Ile Cys His Leu Cys Asn
                20                  25                  30

Lys Thr Tyr Gly Lys Thr Ser His Leu Arg Ala His Leu Arg Gly His
            35                  40                  45

Ala Gly Asn Lys Pro Phe Ala Cys
        50                  55

<210> SEQ ID NO 27
<211> LENGTH: 31
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

Trp Trp Glu Thr Trp Lys Pro Phe Gln Cys Arg Ile Cys Met Arg Asn
 1               5                  10                  15

Phe Ser Thr Arg Gln Ala Arg Arg Asn His Arg Arg Arg His Arg
                20                  25                  30

<210> SEQ ID NO 28
<211> LENGTH: 16
<212> TYPE: PRT
<213> ORGANISM: Artificial Sequence
<220> FEATURE:

```
<223> OTHER INFORMATION: Description of Artificial Sequence: Synthetic
      peptide

<400> SEQUENCE: 28

Gly Lys Ile Asn Leu Lys Ala Leu Ala Ala Leu Ala Lys Lys Ile Leu
 1               5                  10                  15

<210> SEQ ID NO 29
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Arg Val Ile Arg Val Trp Phe Gln Asn Lys Arg Cys Lys Asp Lys Lys
 1               5                  10                  15

<210> SEQ ID NO 30
<211> LENGTH: 39
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Arg Lys Lys Arg Arg Gln Arg Arg Pro Pro Gln Gly Arg Lys
 1               5                  10                  15

Lys Arg Arg Gln Arg Arg Pro Pro Gln Gly Arg Lys Arg Arg
             20                  25                  30

Gln Arg Arg Arg Pro Pro Gln
             35

<210> SEQ ID NO 31
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 31

Gly Glu Gln Ile Ala Gln Leu Ile Ala Gly Tyr Ile Asp Ile Ile Leu
 1               5                  10                  15

Lys Lys Lys Lys Ser Lys
             20

<210> SEQ ID NO 32
<211> LENGTH: 21
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 32
cuacacaaau cagcgauuut t                                           21

<210> SEQ ID NO 33
<211> LENGTH: 21
<212> TYPE: DNA
<213> ORGANISM: Artificial Sequence
```

```
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 33
aaaucgcuga uuuguguagt t                                             21

<210> SEQ ID NO 34
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 34
gcaagcugac ccugaaguuc au                                            22

<210> SEQ ID NO 35
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Arg Arg Arg Gln Arg Arg Lys Arg Gly Gly Asp Ile Met Gly Glu Trp
 1               5                  10                  15

Gly Asn Glu Ile Phe Gly Ala Ile Ala Gly Phe Leu Gly
            20                  25

<210> SEQ ID NO 36
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

Gly Arg Lys Lys Arg Arg Gln Arg Arg Arg Pro Pro Gln Cys
 1               5                  10

<210> SEQ ID NO 37
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Maleimide-Ala

<400> SEQUENCE: 37

Ala Ala Val Ala Leu Leu Pro Ala Val Leu Leu Ala Leu Leu Ala Pro
 1               5                  10                  15

Arg Lys Lys Arg Arg Gln Arg Arg Arg Pro Pro Gln
            20                  25

<210> SEQ ID NO 38
<211> LENGTH: 29
<212> TYPE: PRT
```

<213> ORGANISM: Artificial Sequence
<220> FEATURE:
<223> OTHER INFORMATION: Description of Artificial Sequence: Synthetic
      peptide

<400> SEQUENCE: 38

Ala Ala Val Ala Leu Leu Pro Ala Val Leu Leu Ala Leu Leu Ala Pro
 1               5                  10                  15
Arg Lys Lys Arg Arg Gln Arg Arg Pro Pro Gln Cys
            20                  25

<210> SEQ ID NO 39
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

Arg Lys Lys Arg Arg Gln Arg Arg Pro Pro Gln Cys Ala Ala Val
 1               5                  10                  15
Ala Leu Leu Pro Ala Val Leu Leu Ala Leu Leu Ala Pro
            20                  25

<210> SEQ ID NO 40
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: BrAc-Gly

<400> SEQUENCE: 40

Gly Arg Lys Lys Arg Arg Gln Arg Arg Arg Pro Gln
 1               5                  10

<210> SEQ ID NO 41
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: BrAc-Arg

<400> SEQUENCE: 41

Arg Arg Arg Gln Arg Arg Lys Arg Gly Gly Asp Ile Met Gly Glu Trp
 1               5                  10                  15
Gly Asn Glu Ile Phe Gly Ala Ile Ala Gly Phe Leu Gly
            20                  25

<210> SEQ ID NO 42
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

Cys Tyr Gly Arg Lys Lys Arg Arg Gln Arg Arg Gly Tyr Gly Arg
1               5                   10                  15

Lys Lys Arg Arg Gln Arg Arg Gly
            20                  25

<210> SEQ ID NO 43
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Maleimide-Gly

<400> SEQUENCE: 43

Gly Arg Lys Lys Arg Arg Gln Arg Arg Arg Pro Pro Gln
1               5                   10

<210> SEQ ID NO 44
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 44

Lys Leu Trp Lys Ala Trp Pro Lys Leu Trp Lys Lys Leu Trp Lys Pro
1               5                   10                  15

<210> SEQ ID NO 45
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Ala Ala Val Ala Leu Leu Pro Ala Val Leu Leu Ala Leu Leu Ala Pro
1               5                   10                  15

Arg Arg Arg Arg Arg Arg
            20

<210> SEQ ID NO 46
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Arg Leu Trp Arg Ala Leu Pro Arg Val Leu Arg Arg Leu Leu Arg Pro
1               5                   10                  15

<210> SEQ ID NO 47
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

```
Ala Ala Val Ala Leu Leu Pro Ala Val Leu Leu Ala Leu Leu Ala Pro
 1               5                  10                  15

Ser Gly Ala Ser Gly Leu Asp Lys Arg Asp Tyr Val
            20                  25
```

<210> SEQ ID NO 48
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Maleimide-Ala

<400> SEQUENCE: 48

```
Ala Ala Val Ala Leu Leu Pro Ala Val Leu Leu Ala Leu Leu Ala Pro
 1               5                  10                  15

Ser Gly Ala Ser Gly Leu Asp Lys Arg Asp Tyr Val
            20                  25
```

<210> SEQ ID NO 49
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

```
Ser Gly Ala Ser Gly Leu Asp Lys Arg Asp Tyr Val Ala Ala Val Ala
 1               5                  10                  15

Ala Leu Leu Pro Ala Val Leu Leu Ala Leu Leu Ala Pro
            20                  25
```

<210> SEQ ID NO 50
<211> LENGTH: 33
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

```
Leu Leu Glu Thr Leu Leu Lys Pro Phe Gln Cys Arg Ile Cys Met Arg
 1               5                  10                  15

Asn Phe Ser Thr Arg Gln Ala Arg Arg Asn His Arg Arg Arg His Arg
            20                  25                  30

Arg
```

<210> SEQ ID NO 51
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

```
Ala Ala Val Ala Cys Arg Ile Cys Met Arg Asn Phe Ser Thr Arg Gln
 1               5                  10                  15

Ala Arg Arg Asn His Arg Arg Arg His Arg Arg
            20                  25
```

```
<210> SEQ ID NO 52
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Maleimide-Arg

<400> SEQUENCE: 52

Arg Gln Ile Lys Ile Trp Phe Gln Asn Arg Arg Met Lys Trp Lys Lys
 1               5                  10                  15

<210> SEQ ID NO 53
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Arg Gln Ile Lys Ile Trp Phe Gln Asn Arg Arg Met Lys Trp Lys Lys
 1               5                  10                  15

<210> SEQ ID NO 54
<211> LENGTH: 35
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Arg Gln Ile Lys Ile Trp Phe Gln Asn Arg Arg Met Lys Trp Lys Lys
 1               5                  10                  15

Asp Ile Met Gly Glu Trp Gly Asn Glu Ile Phe Gly Ala Ile Ala Gly
             20                  25                  30

Phe Leu Gly
         35

<210> SEQ ID NO 55
<211> LENGTH: 37
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Maleimide-Ser

<400> SEQUENCE: 55

Ser Gly Arg Gly Lys Gln Gly Gly Lys Ala Arg Ala Lys Ala Lys Thr
 1               5                  10                  15

Arg Ser Ser Arg Ala Gly Leu Gln Phe Pro Val Gly Arg Val His Arg
             20                  25                  30

Leu Leu Arg Lys Gly
         35

<210> SEQ ID NO 56
<211> LENGTH: 38
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 56

Ser Gly Arg Gly Lys Gln Gly Gly Lys Ala Arg Ala Lys Ala Lys Thr
1               5                   10                  15

Arg Ser Ser Arg Ala Gly Leu Gln Phe Pro Val Gly Arg Val His Arg
            20                  25                  30

Leu Leu Arg Lys Gly Cys
        35

<210> SEQ ID NO 57
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Lys Gly Ser Lys Lys Ala Val Thr Lys Ala Gln Lys Lys Asp Gly Lys
1               5                   10                  15

Lys Arg Lys Arg Ser Arg Lys
            20

<210> SEQ ID NO 58
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Lys Lys Asp Gly Lys Lys Arg Lys Arg Ser Arg Lys Glu Ser Tyr Ser
1               5                   10                  15

Val Tyr Val Tyr Lys Val Leu Lys Gln
            20                  25

<210> SEQ ID NO 59
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 59

Lys Gly Ser Lys Lys Ala Val Thr Lys Ala Gln Lys Lys Asp Gly Lys
1               5                   10                  15

Lys Arg Lys Arg Ser Arg Lys Glu Ser Tyr Ser Val Tyr Val Tyr Lys
            20                  25                  30

Val Leu Lys Gln
        35

<210> SEQ ID NO 60
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
```

```
<222> LOCATION: (1)
<223> OTHER INFORMATION: BrAc-Gly

<400> SEQUENCE: 60

Gly Trp Thr Leu Asn Ser Ala Gly Tyr Leu Leu Gly Lys Ile Asn Leu
 1               5                  10                  15

Lys Ala Leu Ala Ala Leu Ala Lys Lys Ile Leu
            20                  25

<210> SEQ ID NO 61
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: BrAc-Lys

<400> SEQUENCE: 61

Lys Leu Ala Leu Lys Leu Ala Leu Lys Ala Leu Lys Ala Ala Leu Lys
 1               5                  10                  15

Leu Ala

<210> SEQ ID NO 62
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Ac-Lys

<400> SEQUENCE: 62

Lys Glu Thr Trp Trp Glu Thr Trp Trp Thr Glu Trp Ser Gln Pro Lys
 1               5                  10                  15

Lys Lys Arg Lys Val
            20

<210> SEQ ID NO 63
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 63

Lys Glu Thr Trp Trp Glu Thr Trp Trp Thr Glu Trp Ser Gln Pro Gly
 1               5                  10                  15

Arg Lys Lys Arg Arg Gln Arg Arg Pro Pro Gln
            20                  25

<210> SEQ ID NO 64
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
```

<223> OTHER INFORMATION: BrAc-Arg

<400> SEQUENCE: 64

Arg Arg Arg Arg Arg Arg Arg
 1               5

<210> SEQ ID NO 65
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Gln
<220> FEATURE:
<221> NAME/KEY: MOD_RES
<222> LOCATION: (4)
<223> OTHER INFORMATION: D-Gln
<220> FEATURE:
<221> NAME/KEY: MOD_RES
<222> LOCATION: (6)
<223> OTHER INFORMATION: D-Gln
<220> FEATURE:
<221> NAME/KEY: MOD_RES
<222> LOCATION: (8)
<223> OTHER INFORMATION: D-Gln
<220> FEATURE:
<221> NAME/KEY: MOD_RES
<222> LOCATION: (10)
<223> OTHER INFORMATION: D-Gln

<400> SEQUENCE: 65

Gln Gln Gln Gln Gln Gln Gln Gln Gln Gln
 1               5                  10

<210> SEQ ID NO 66
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (11)
<223> OTHER INFORMATION: D-Gln
<220> FEATURE:
<221> NAME/KEY: MOD_RES
<222> LOCATION: (13)
<223> OTHER INFORMATION: D-Gln
<220> FEATURE:
<221> NAME/KEY: MOD_RES
<222> LOCATION: (15)
<223> OTHER INFORMATION: D-Gln
<220> FEATURE:
<221> NAME/KEY: MOD_RES
<222> LOCATION: (17)
<223> OTHER INFORMATION: D-Gln
<220> FEATURE:
<221> NAME/KEY: MOD_RES
<222> LOCATION: (19)
<223> OTHER INFORMATION: D-Gln

<400> SEQUENCE: 66

Arg Arg Arg Gln Arg Arg Lys Arg Gly Gly Gln Gln Gln Gln Gln
 1               5                  10                  15

Gln Gln Gln Gln
            20

<210> SEQ ID NO 67

```
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Arg Val Ile Arg Trp Phe Gln Asn Lys Arg Cys Lys Asp Lys Lys
 1               5                  10                  15

<210> SEQ ID NO 68
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Ac-Leu

<400> SEQUENCE: 68

Leu Gly Leu Leu Leu Arg His Leu Arg His His Ser Asn Leu Leu Ala
 1               5                  10                  15

Asn Ile

<210> SEQ ID NO 69
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Gly Gln Met Ser Glu Ile Glu Ala Lys Val Arg Thr Val Lys Leu Ala
 1               5                  10                  15

Arg Ser

<210> SEQ ID NO 70
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Lys Leu Trp Ser Ala Trp Pro Ser Leu Trp Ser Ser Leu Trp Lys Pro
 1               5                  10                  15

<210> SEQ ID NO 71
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Lys Lys Lys Lys Lys Lys Lys Lys Lys
 1               5

<210> SEQ ID NO 72
<211> LENGTH: 21
<212> TYPE: PRT
```

```
<213> ORGANISM: Artificial Sequence
<220> FEATURE:
<223> OTHER INFORMATION: Description of Artificial Sequence: Synthetic
      peptide

<400> SEQUENCE: 72

Ala Ala Arg Leu His Arg Phe Lys Asn Lys Gly Lys Asp Ser Thr Glu
 1               5                  10                  15

Met Arg Arg Arg Arg
            20

<210> SEQ ID NO 73
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Maleimide-Gly

<400> SEQUENCE: 73

Gly Leu Gly Ser Leu Leu Lys Lys Ala Gly Lys Lys Leu Lys Gln Pro
 1               5                  10                  15

Lys Ser Lys Arg Lys Val
            20

<210> SEQ ID NO 74
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Maleimide-Dmt-r-Phe
<220> FEATURE:
<221> NAME/KEY: MOD_RES
<222> LOCATION: (4)
<223> OTHER INFORMATION: D-Gln
<220> FEATURE:
<221> NAME/KEY: MOD_RES
<222> LOCATION: (6)
<223> OTHER INFORMATION: D-Gln
<220> FEATURE:
<221> NAME/KEY: MOD_RES
<222> LOCATION: (8)
<223> OTHER INFORMATION: D-Gln
<220> FEATURE:
<221> NAME/KEY: MOD_RES
<222> LOCATION: (10)
<223> OTHER INFORMATION: D-Gln
<220> FEATURE:
<221> NAME/KEY: MOD_RES
<222> LOCATION: (12)
<223> OTHER INFORMATION: D-Gln

<400> SEQUENCE: 74

Phe Lys Gln Gln Gln Gln Gln Gln Gln Gln Gln Gln
 1               5                  10

<210> SEQ ID NO 75
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<221> NAME/KEY: MOD_RES
<222> LOCATION: (1)
<223> OTHER INFORMATION: Maleimide-Trp

<400> SEQUENCE: 75

Trp Arg Phe Lys
  1

<210> SEQ ID NO 76
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Maleimide-Trp
<220> FEATURE:
<221> NAME/KEY: MOD_RES
<222> LOCATION: (6)
<223> OTHER INFORMATION: D-Gln
<220> FEATURE:
<221> NAME/KEY: MOD_RES
<222> LOCATION: (8)
<223> OTHER INFORMATION: D-Gln
<220> FEATURE:
<221> NAME/KEY: MOD_RES
<222> LOCATION: (10)
<223> OTHER INFORMATION: D-Gln
<220> FEATURE:
<221> NAME/KEY: MOD_RES
<222> LOCATION: (12)
<223> OTHER INFORMATION: D-Gln
<220> FEATURE:
<221> NAME/KEY: MOD_RES
<222> LOCATION: (14)
<223> OTHER INFORMATION: D-Gln

<400> SEQUENCE: 76

Trp Arg Phe Lys Gln Gln Gln Gln Gln Gln Gln Gln Gln Gln
  1               5                  10

<210> SEQ ID NO 77
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Maleimido-Tyr

<400> SEQUENCE: 77

Tyr Arg Phe Lys
  1

<210> SEQ ID NO 78
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Maleimide-Tyr

<400> SEQUENCE: 78
```

```
Tyr Arg Phe Lys Tyr Arg Phe Lys Tyr Arg Phe Lys
 1               5                   10

<210> SEQ ID NO 79
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Maleimide-Trp

<400> SEQUENCE: 79

Trp Arg Phe Lys Lys Ser Lys Arg Lys Val
 1               5                   10

<210> SEQ ID NO 80
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Maleimide-Trp

<400> SEQUENCE: 80

Trp Arg Phe Lys Ala Ala Val Ala Leu Leu Pro Ala Val Leu Leu Ala
 1               5                   10                  15

Leu Leu Ala Pro
            20

<210> SEQ ID NO 81
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Dimethylated-Tyr
<220> FEATURE:
<221> NAME/KEY: MOD_RES
<222> LOCATION: (2)
<223> OTHER INFORMATION: D-Arg

<400> SEQUENCE: 81

Tyr Arg Phe Lys
 1

<210> SEQ ID NO 82
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Arg

<400> SEQUENCE: 82
```

Tyr Arg Phe Lys
1

<210> SEQ ID NO 83
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Dimethylated-Tyr

<400> SEQUENCE: 83

Tyr Arg Phe Lys
1

<210> SEQ ID NO 84
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: D-Arg

<400> SEQUENCE: 84

Trp Arg Phe Lys
1

<210> SEQ ID NO 85
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Dimethylated-Tyr
<220> FEATURE:
<221> NAME/KEY: MOD_RES
<222> LOCATION: (2)
<223> OTHER INFORMATION: D-Arg

<400> SEQUENCE: 85

Tyr Arg Trp Lys
1

<210> SEQ ID NO 86
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)
<223> OTHER INFORMATION: D-Arg
<220> FEATURE:
<221> NAME/KEY: MOD_RES
<222> LOCATION: (4)
<223> OTHER INFORMATION: Dimethylated-Tyr

<400> SEQUENCE: 86

Lys Phe Arg Tyr
 1

<210> SEQ ID NO 87
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Maleimide-Trp

<400> SEQUENCE: 87

Trp Arg Phe Lys Trp Arg Phe Lys
 1               5

<210> SEQ ID NO 88
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Maleimide-Trp

<400> SEQUENCE: 88

Trp Arg Phe Lys Trp Arg Phe Lys Trp Arg Phe Lys
 1               5                  10

<210> SEQ ID NO 89
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 89

Arg Lys Lys Arg Arg Gln Arg Arg Pro Pro Gln Ala Ala Val Ala
 1               5                  10                  15

Leu Leu Pro Ala Val Leu Leu Ala Leu Leu Ala Pro
             20                  25

<210> SEQ ID NO 90
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Peg-Lys

<400> SEQUENCE: 90

Lys Gly Ser Lys Lys Ala Val Thr Lys Ala Gln Lys Lys Asp Gly Lys
 1               5                  10                  15

Lys Arg Lys Arg Ser Arg Lys Glu Ser Tyr Ser Val Tyr Val Tyr Lys
                 20                  25                  30

Val Leu Lys Gln
             35

<210> SEQ ID NO 91
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 91

Arg Gly Ser Arg Arg Ala Val Thr Arg Ala Gln Arg Arg Asp Gly Arg
 1               5                  10                  15

Arg Arg Arg Arg Ser Arg Arg Glu Ser Tyr Ser Val Tyr Val Tyr Arg
                20                  25                  30

Val Leu Arg Gln
            35

<210> SEQ ID NO 92
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Maleimido-Arg

<400> SEQUENCE: 92

Arg Val Ile Arg Trp Phe Gln Asn Lys Arg Ser Lys Asp Lys Lys
 1               5                  10                  15

<210> SEQ ID NO 93
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 93

Gly Trp Thr Leu Asn Ser Ala Gly Tyr Leu Leu Gly Lys Ile Asn Leu
 1               5                  10                  15

Lys Ala Leu Ala Ala Leu Ala Lys Lys Ile Leu
                20                  25

<210> SEQ ID NO 94
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 94

Ala Ala Val Ala Leu Leu Pro Ala Val Leu Leu Ala Leu Leu Ala Pro
 1               5                  10                  15

Arg Lys Lys Arg Arg Gln Arg Arg Arg Pro Pro Gln
                20                  25

<210> SEQ ID NO 95
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 95

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 96
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gly Ala Leu Phe Leu Gly Phe Leu Gly Ala Ala Gly Ser Thr Met Gly
1               5                   10                  15

Ala Trp Ser Gln Pro Lys Ser Lys Arg Lys Val Cys
            20                  25

<210> SEQ ID NO 97
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Tyr Arg Phe Lys
1

<210> SEQ ID NO 98
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Trp Arg Phe Lys
1

<210> SEQ ID NO 99
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Trp Arg Phe Lys Trp Arg Phe Lys
1               5

<210> SEQ ID NO 100
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Tyr Arg Phe Lys Tyr Arg Phe Lys Tyr Arg Phe Lys
```

```
<210> SEQ ID NO 101
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Trp Arg Phe Lys Lys Ser Lys Arg Lys Val
 1               5                  10

<210> SEQ ID NO 102
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Maleimide-Arg

<400> SEQUENCE: 102

Arg Arg Arg Gln Arg Arg Lys Arg Gly Gly Asp Ile Met Gly Glu Trp
 1               5                  10                  15

Gly Asn Glu Ile Phe Gly Ala Ile Ala Gly Phe Leu Gly
            20                  25

<210> SEQ ID NO 103
<211> LENGTH: 36
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Maleimide-Lys

<400> SEQUENCE: 103

Lys Gly Ser Lys Lys Ala Val Thr Lys Ala Gln Lys Lys Asp Gly Lys
 1               5                  10                  15

Lys Arg Lys Arg Ser Arg Lys Glu Ser Tyr Ser Val Tyr Val Tyr Lys
            20                  25                  30

Val Leu Lys Gln
        35

<210> SEQ ID NO 104
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Maleimido-Lys

<400> SEQUENCE: 104

Lys Glu Thr Trp Trp Glu Thr Trp Trp Thr Glu Trp Ser Gln Pro Lys
 1               5                  10                  15

Lys Lys Arg Lys Val
```

-continued

```
<210> SEQ ID NO 105
<211> LENGTH: 29
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Maleimide-Arg

<400> SEQUENCE: 105

Arg Lys Lys Arg Arg Gln Arg Arg Pro Pro Gln Cys Ala Ala Val
 1               5                  10                  15

Ala Leu Leu Pro Ala Val Leu Leu Ala Leu Leu Ala Pro
             20                  25

<210> SEQ ID NO 106
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Trp Arg Phe Lys Cys
 1               5

<210> SEQ ID NO 107
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Maleimido-Lys

<400> SEQUENCE: 107

Lys Leu Ala Leu Lys Leu Ala Leu Lys Ala Leu Lys Ala Ala Leu Lys
 1               5                  10                  15

Leu Ala

<210> SEQ ID NO 108
<211> LENGTH: 27
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)
<223> OTHER INFORMATION: Maleimido-Gly

<400> SEQUENCE: 108

Gly Trp Thr Leu Asn Ser Ala Gly Tyr Leu Leu Gly Lys Ile Asn Leu
 1               5                  10                  15

Lys Ala Leu Ala Ala Leu Ala Lys Lys Ile Leu
             20                  25

<210> SEQ ID NO 109
```

```
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 109
gcgtggagct gagagataa                                                   19

<210> SEQ ID NO 110
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 110
gcctgtagcc catgttgta                                                   19

<210> SEQ ID NO 111
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 111
ggtatgagcc catctatct                                                   19

<210> SEQ ID NO 112
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 112
ccagggacct ctctctaat                                                   19

<210> SEQ ID NO 113
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113
gcccgactat ctcgacttt                                                   19

<210> SEQ ID NO 114
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
tgacaagcct gtagcccat                                                   19

<210> SEQ ID NO 115
<211> LENGTH: 19
<212> TYPE: DNA
```

```
<213> ORGANISM: Artificial Sequence
<220> FEATURE:
<223> OTHER INFORMATION: Description of Artificial Sequence: Synthetic
      oligonucleotide

<400> SEQUENCE: 115
ggtctacttt gggatcatt                                                    19

<210> SEQ ID NO 116
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 116
cccagggacc tctctctaa                                                    19

<210> SEQ ID NO 117
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 117
aatcggcccg actatctcga ctt                                               23

<210> SEQ ID NO 118
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 118
aauggcgugg agcugagaga u                                                 21

<210> SEQ ID NO 119
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 119
aaccuccucu cugccaucaa g                                                 21

<210> SEQ ID NO 120
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 120
aacugaaagc augauccggg a                                                 21

<210> SEQ ID NO 121
<211> LENGTH: 21
<212> TYPE: RNA
<213> ORGANISM: Artificial Sequence
<220> FEATURE:
```

<223> OTHER INFORMATION: Description of Artificial Sequence: Synthetic
      oligonucleotide

<400> SEQUENCE: 121
aaucucgacu uugccgaguc u                                              21

<210> SEQ ID NO 122
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 122
aagggugacc gacucagcgc u                                              21

<210> SEQ ID NO 123
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 123
aaucagccgc aucgccgucu c                                              21

<210> SEQ ID NO 124
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 124
aacccaugug cuccucaccc a                                              21

<210> SEQ ID NO 125
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 125
aagcuccagu ggcugaaccg c                                              21

<210> SEQ ID NO 126
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 126
aagucagauc aucuucucga a                                              21

<210> SEQ ID NO 127
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<210> SEQ ID NO 127

<400> SEQUENCE: 127
aagggaccuc ucucuaauca g                                    21

<210> SEQ ID NO 128
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 128
cctcagcctc ttctccttcc tga                                  23

<210> SEQ ID NO 129
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 129
aauccucagc cucuucuccu u                                    21

<210> SEQ ID NO 130
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 130
aaccaaugcc cuccuggcca a                                    21

<210> SEQ ID NO 131
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 131
ctgattaagt tgtctaaaca a                                    21

<210> SEQ ID NO 132
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 132
ccgactcagc gctgagatca a                                    21

<210> SEQ ID NO 133
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 133
cttgtgatta tttattattt a                                           21

<210> SEQ ID NO 134
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 134
aagcctgtag cccatgttgt a                                           21

<210> SEQ ID NO 135
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 135
tagggtcgga acccaagctt a                                           21

<210> SEQ ID NO 136
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 136
cugaaagcau gauccggga                                              19

<210> SEQ ID NO 137
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 137
aggcggugcu uguuccuca                                              19

<210> SEQ ID NO 138
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 138
ccaccacgcu cuucugccu                                              19

<210> SEQ ID NO 139
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 139
agggaccucu cucuaauca                                              19

```
<210> SEQ ID NO 140
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 140
ugacaagccu guagcccau                                                      19

<210> SEQ ID NO 141
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 141
gccuguagcc cauguugua                                                      19

<210> SEQ ID NO 142
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 142
uagcccaugu uguagcaaa                                                      19

<210> SEQ ID NO 143
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 143
ccaaugcccu ccuggccaa                                                      19

<210> SEQ ID NO 144
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 144
ccaauggcgu ggagcugag                                                      19

<210> SEQ ID NO 145
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 145
ggcguggagc ugagagaua                                                      19
```

<210> SEQ ID NO 146
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 146
gcguggagcu gagagauaa                                                    19

<210> SEQ ID NO 147
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 147
gccuguaccu caucuacuc                                                    19

<210> SEQ ID NO 148
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 148
ccuccucucu gccaucaag                                                    19

<210> SEQ ID NO 149
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 149
gguaugagcc caucuaucu                                                    19

<210> SEQ ID NO 150
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 150
gcuggagaag ggugaccga                                                    19

<210> SEQ ID NO 151
<211> LENGTH: 19
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 151
gagaagggug accgacuca                                                    19

<210> SEQ ID NO 152
<211> LENGTH: 19

```
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 152
gcccgacuau cucgacuuu                                                  19

<210> SEQ ID NO 153
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 153
gcaggucuac uuugggauc                                                  19

<210> SEQ ID NO 154
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 154
ggucuacuuu gggaucauu                                                  19

<210> SEQ ID NO 155
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 155
ugggaucauu gcccuguga                                                  19

<210> SEQ ID NO 156
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 156
ggtcggaacc caagcttag                                                  19

<210> SEQ ID NO 157
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 157
ccagaatgct gcaggactt                                                  19

<210> SEQ ID NO 158
<211> LENGTH: 19
<212> TYPE: DNA
<213> ORGANISM: Artificial Sequence
```

```
<220> FEATURE:
<223> OTHER INFORMATION: Description of Artificial Sequence: Synthetic
      oligonucleotide

<400> SEQUENCE: 158
gagaagacct caccctagaa                                                    19

<210> SEQ ID NO 159
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 159
gaagacctca cctagaaat                                                     19

<210> SEQ ID NO 160
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 160
ccagatgttt ccagacttc                                                     19

<210> SEQ ID NO 161
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 161
ctatttatgt ttgcacttg                                                     19

<210> SEQ ID NO 162
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 162
tctaaacaat gctgatttg                                                     19

<210> SEQ ID NO 163
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 163
gaccaactgt cactcatt                                                      18
```